US012404516B2

(12) United States Patent
Schulze Gronover et al.

(10) Patent No.: US 12,404,516 B2
(45) Date of Patent: Sep. 2, 2025

(54) METHOD TO OBTAIN LOW TRITERPENE/TRITERPENOID-CONTAINING NATURAL RUBBER LATEX

(71) Applicant: Fraunhofer-Gesellschaft zur Foerderung der Angewandten Forschung E.V., Munich (DE)

(72) Inventors: Christian Schulze Gronover, Muenster (DE); Kristina Unland, Muenster (DE)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 561 days.

(21) Appl. No.: 17/291,990

(22) PCT Filed: Nov. 8, 2019

(86) PCT No.: PCT/EP2019/080668

§ 371 (c)(1),
(2) Date: May 6, 2021

(87) PCT Pub. No.: WO2020/094838

PCT Pub. Date: May 14, 2020

(65) Prior Publication Data

US 2022/0010323 A1 Jan. 13, 2022

(30) Foreign Application Priority Data

Nov. 8, 2018 (EP) .................................... 18205121

(51) Int. Cl.

| | |
|---|---|
| ***C12N 15/82*** | (2006.01) |
| ***C12N 9/90*** | (2006.01) |
| ***C12N 15/11*** | (2006.01) |
| ***C12N 15/113*** | (2010.01) |

(52) U.S. Cl.
CPC ........... *C12N 15/8243* (2013.01); *C12N 9/90* (2013.01); *C12N 15/1137* (2013.01); *C12Y 504/99007* (2013.01); *C12N 2310/14* (2013.01)

(58) Field of Classification Search
CPC .................................................. C12N 15/8243
See application file for complete search history.

(56) References Cited

U.S. PATENT DOCUMENTS

2004/0010818 A1* 1/2004 McGonigle ........ C12N 15/8243 435/193

FOREIGN PATENT DOCUMENTS

| | | | |
|---|---|---|---|
| WO | 01/66773 | A2 | 9/2001 |
| WO | 03/095615 | A2 | 11/2003 |
| WO | 2005/089198 | A2 | 9/2005 |
| WO | 2007/056347 | A1 | 5/2007 |

OTHER PUBLICATIONS

Hagel et al.,2008, Got milk? The secret life of laticifers. Trends in plant science, 13(12), 631-639. (Year: 2008).*

Van Deenen et al., 2019, Oxidosqualene cyclase knock-down in latex of Taraxacum koksaghyz reduces triterpenes in roots and separated natural rubber. Molecules, 24(15), 2703. (Year: 2019).*

Thimmappa et al., 2014, Triterpene biosynthesis in plants. Annual review of plant biology, 65, 225-257. (Year: 2014).*

Diemer et al., 2006, Artemisia annua; the plant, production and processing and medicinal applications. The World Health Organization: Geneva. (Year: 2006).*

Moses et al.,2015, OSC2 and CYP716A14v2 catalyze the biosynthesis of triterpenoids for the cuticle of aerial organs of Artemisia annua. The Plant Cell, 27(1), 286-301. (Year: 2015).*

Shibuya et al.,1999, Two branches of the lupeol synthase gene in the molecular evolution of plant oxidosqualene cyclases. European Journal of Biochemistry, 266(1), 302-307. (Year: 1999).*

NCBI Nucleotide Database; Lupeol synthase [Taraxacum officinale]; GenBank: BAA86932.1. Submitted: Mar. 26, 1999; Masaaki Shibuya, The University of Tokyo, Faculty of Pharmaceutical Sciences; 7-3-1 Hongo, Bunkyo-ku, Tokyo 113-0033, Japan (E-mail: shibuyam@mol.f.u-tokyo.ac.jp. (Year: 1999).*

Chen et al., 2021, Off-target effects of RNAi correlate with the mismatch rate between dsRNA and non-target mRNA. RNA biology, 18(11), 1747-1759. (Year: 2021).*

Putter et al., 2019, The enzymes OSC1 and CYP716A263 produce a high variety of triterpenoids in the latex of Taraxacum koksaghyz. Scientific Reports, 9(1), 5942. (Year: 2019).*

Abe, I., "Enzymatic synthesis of cyclic triterpenes," Natural Product Reports, 24:1311-1331; Aug. 2007.

Akashi, T., et al., "Biosynthesis of triterpenoids in cultured cells, and regenerated and wild plant organs of Taraxacum officinale," Phytochemistry, 36:303-308; May 1994.

Augustin, J.M., et al., "Molecular activities, biosynthesis and evolution of triterpenoid saponins," Phytochemistry, 72:435-457; Apr. 2011.

Clouse, S.D., "Arabidopsis Mutants Reveal Multiple Roles for Sterols in Plant Development," The Plant Cell, 14:1995-2000, Sep. 2002.

(Continued)

*Primary Examiner* — Amjad Abraham
*Assistant Examiner* — Santosh Sharma
(74) *Attorney, Agent, or Firm* — Kagan Binder, PLLC

(57) ABSTRACT

The invention provides a method of reducing or eliminating the content of triterpenes and/or triterpenoids of latex or rubber from a laticiferous plant or part thereof, comprising genetically modifying the laticiferous plant or part thereof, such that the activity of at least one oxidosqualene cyclase is reduced or eliminated, compared to the respective wild-type or untreated laticiferous plant or part thereof. The invention further provides a laticiferous plant or part thereof being genetically modified such that the activity of at least one oxidosqualene cyclase is reduced or eliminated, compared to the respective wild-type or untreated laticiferous plant or part thereof, and an RNAi being specifically directed against a mRNA transcript of at least one oxidosqualene cyclase, for use in a method of reducing or eliminating the content of triterpenes and/or triterpenoids of latex or rubber from a laticiferous plant or part thereof.

15 Claims, 10 Drawing Sheets

Specification includes a Sequence Listing.

(56) References Cited

OTHER PUBLICATIONS

Davis et al., "The Rubber Industry's Biological Nightmare," CNN Money, Aug. 1997, retrieved from https://money.cnn.com/magazines/fortune/fortune_archive/1997/08//04/229714/index.htm, 4 pp.
Epping, J., et al., "A rubber transferase activator is necessary for natural rubber biosynthesis in dandelion," Nature Plants, Art. No. 15048, Apr. 2015, 9 pages.
Furuno, T., et al., "Triterpenold Constituents of Tissue Cultures and Regenerated Organs of Taraxacum officinale," Plant Tissue Culture Letters, 10:275-280; 1993.
Gronover, C.S., et al., "Chapter 4—Natural Rubber Biosynthesis and Physic-Chemical Studies on Plant Derived Latex," from Biotechnology of Biopolymers, edited by Magdy Elnashar, Jun. 2011, pp. 75-88.
Hagel, J.M., et al., "Got milk? The secret life of laticifers, " Trends in Plant Sciences, 13:631-639; Oct. 2008.
Hartmann, M-A., "Plant sterols and the membrane environment," Trends in Plant Science, 3:170-175; May 1998.
Krotkov, G., "A Review of Literature on Taraxacum Kok-Saghyz Rod," The Botanical Review, 11:417-461; Oct. 1945.
Mooibroek, H., and Cornish, K., "Alternative sources of natural rubber," Applied Microbiology and Biotechnology, 53:355-365, Apr. 2000.
Moses, T. et al., "Metabolic and functional diversity of saponins, biosynthetic intermediates and semi-synthetic derivatives," Critical Review in Biochemistry and Molecular Biology, 49:439-462; Oct. 2014.
Nor, H.M., and Ebdon, J.R., "Telechelic liquid natural rubber: A review," Progress in Polymer Science, 23:143-177; 1998.
Osbourn, A., et al., "The saponins-polar isoprenoids with important and diverse biological activities," Natural Products Report, 28:1261-1268; May 2011.
Putter, K.M., et al., "Isoprenoid biosynthesis in dandelion latex is enhanced by the overexpression of three key enzymes involved in the mevalonate pathway," BMC Plant Biology, 17:p. 13, May 2017.
Sakdapipanich, J.T., "Structural Characterization of Natural Rubber Based on Recent Evidence from Selective Enzymatic Treatments," Journal of Bioscience and Bioengineering, 103:287-292; Apr. 2007.
Schmidt, T., et al., "Characterization of rubber particles and rubber chain elongation in Taraxacum koksaghyz," BMC Biochemistry, 11: p. 11, Feb. 2010.
Stolze, A., et al., "Development of rubber-enriched dandelion varieties by metabolic engineering of the inulin pathway," Plant Biotechnology Journal, 15:740-753; Feb. 2017.
Thimmappa, R., et al., "Triterpene Biosynthesis in Plants," Annual Review of Plant Biology, 65:225-257; Jan. 2014.
Unland, K., et al., "Functional characterization of squalene synthase and squalene epoxidase in Taraxacum koksaghyz," Plant Direct, 2:1-15 (e00063), Jun. 2018.
Xu, R., et al., "On the origins of triterpenoid skeletal diversity," Phytochemistry, 65:261-291, Feb. 2004.
GenBank Accession No. MG646376.1, "Taraxacum kok-saghyz oxidosqualene cyclase 1 (OSC1) mRNA, complete cds," 2313 bp, Sep. 11, 2018, 2 pp.
Salehi, M., et al. (2021) "Natural rubber-producing sources, systems, and perspectives for breeding and biotechnology studies of Taraxacum kok-saghyz", Industrial Crops & Products, 170:1-12.

* cited by examiner

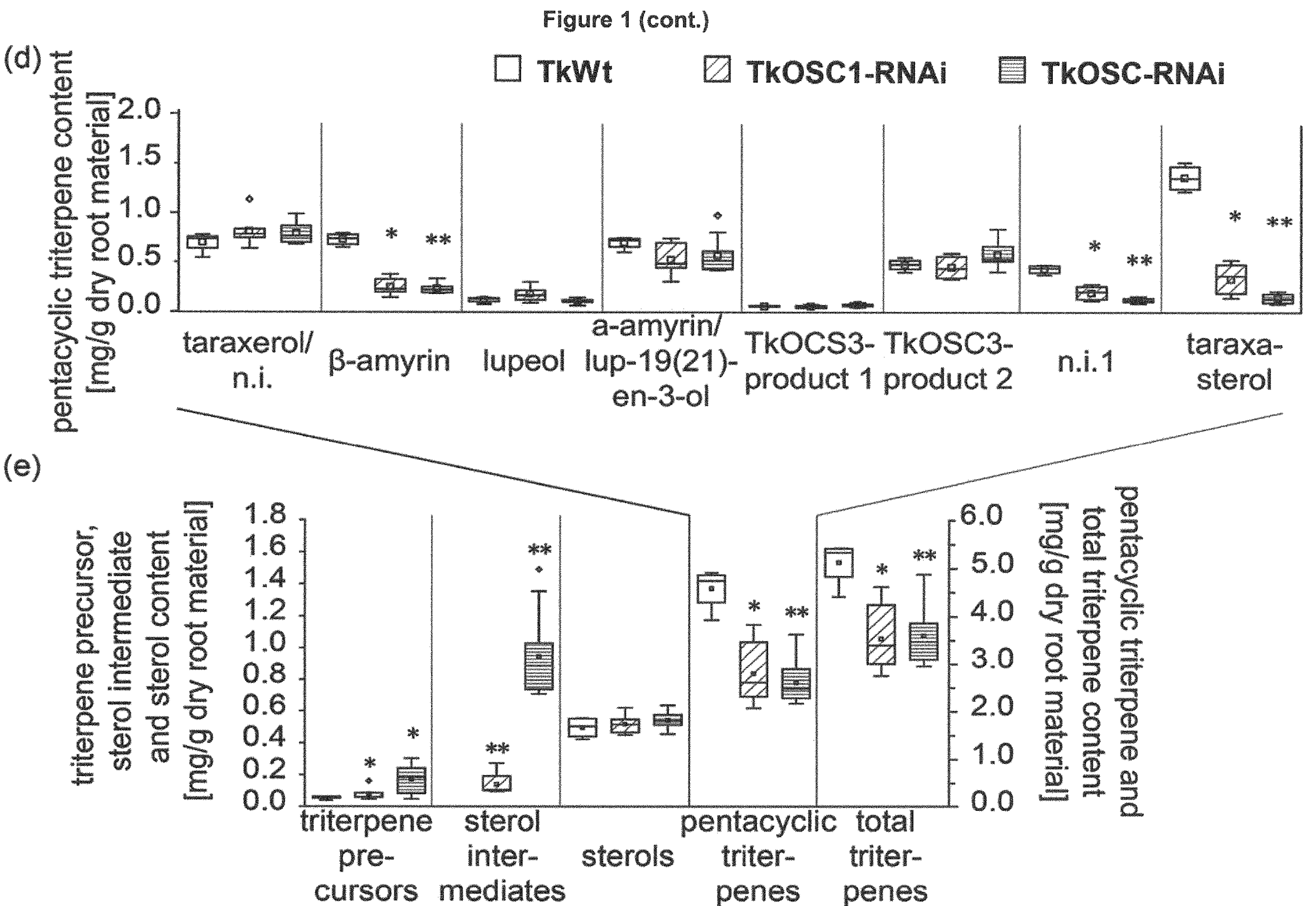

Figure 1 (cont.)
TkWt
TkOSC1-RNAi
TkOSC-RNAi
(d)
pentacyclic triterpene content
[mg/g dry root material]
2.0
1.5
1.0
0.5
0.0
taraxerol/
n.i.
β-amyrin
lupeol
a-amyrin/
lup-19(21)-
en-3-ol
TkOCS3-
product 1
TkOSC3-
product 2
n.i.1
taraxa-
sterol
(e)
triterpene precursor,
sterol intermediate
and sterol content
[mg/g dry root material]
1.8
1.6
1.4
1.2
1.0
0.8
0.6
0.4
0.2
0.0
triterpene
pre-
cursors
sterol
inter-
mediates
sterols
pentacyclic
triter-
penes
total
triter-
penes
pentacyclic triterpene and
total triterpene content
[mg/g dry root material]
6.0
5.0
4.0
3.0
2.0
1.0
0.0

Figure 3

```
TKOSC1    MWKLRIGEKNGKFNIGDGNGDDYLHSTNNFVGRQTWEFDPDA-GTQKERDEIERLREQFL    59
TKOSC2    MWKLRIGEKNGKFNIGDGNGDEYLYSTNNFVGRQTWEFDPDA-GTQEERDEVERLREQFL    59
TkOSC8    MWKLKIAEGN----------DPYLFSTNNFVGRQIWEFDPDA-GTPEERQEVENARQNFL    49
TKOSC3    MWELKIAEGD----------GPYLYSTNNFVGRQFWEFNPDA-GTPEEKEEIEKVRQKFK    49
TkOSC7    MWKLKIAQGN----------DPYLFSTNNFVGRQIWEFDPDA-GTPAERQEVEDARQYFR    49
TkLUP     MWKLKIAEGS---------DDEWLTTTNNHVGRQHWQFDPDA-GTEEERAQIEKIRLNFK    50
TKOSC4    MWRLRIGQGN--------KDDPYLFSTNNFVGRQIWEYDENYKATPEELEEVKQARSSFW    52
TKOSC5    MWKLKIAEGG---------NDPYLHSTNNFIGRQIWEFDSNH-GTPEDRAEAEHARINFW    50
TKOSC6    MWKLKIAEGG---------NDPYLHSTNNFIGRQIWEFDPNH-GTTEDRAEVEQARLDFW    50
          **.*:*.: .          . :* :***.:*** *::: :  .*  :  : :  *  *

TKOSC1    INKKKLDIRCCADLLMRNQLIKESGIDLISVPPVRLGDDEDVNYEAVTTAVRKAVRLNRA    119
TKOSC2    INKKKLDISCCADLLMRNQLIKESGIDLISEAPVKLGHDEDVNYKAVTTAVRKAVRLNRA    119
TkOSC8    N-RQKEGFQTCGDLLMRIQLIRENGIDLLSIPPARLGEKEDVDYEAVTTSIRKAVRYSCA    108
TKOSC3    DNRKKGGFHACGDLLMRMQLMKENAIDLTSILPVRISEGEQVNYEATTIAVRKAVRLHRG    109
TkOSC7    NNRR-EGVHPCGDLLMRAQLIKESGIDVSSIPPTRLEENEEVNYDALTTAVKKALRLNRA    108
TkLUP     LNRF--QFKQSADLLMRTQLRKENPINK-IPDAIKLNETEEVTNDAVSTTLKRAISFYST    107
TKOSC4    NNRH--KQRPCDDRLWRFQFLREKNFKQ-TIPREIIVDESEIKYETVDNALKRAVRYWTA    109
TKOSC5    NLRH--RVKPSSDVLWRMQFLKEKQFKQ-TIAQVKIEEFEEISYEKATVTLKRCVNLFAA    107
TKOSC6    NHRH--QVKPSSDVLWRMQFLKEKEFKQ-TIAQVKIEDSEEISYEKTTTTLRRCVSFFAA    107
            :       . * * * *: :*. :.        : . .::  .    ::::.:
```

Figure 3 (cont.)

```
TKOSC1     IQAWDGHWPAENAGPLFFTPPLIIALYISGTLDTILTQEHKREMIRYMYIHQNEDGGWGF    179
TKOSC2     IQAWDGHWPAENAGPLFFTPPLIIVLYISGTLDNVLTQDHKKEMIRYMYIHQNEDGGWGF    179
TkOSC8     IQAKDGHWATEHGGPLFFTPPLIIILYISGAIDTHLTKEHKKEMKRFIHNHQNEDGGWGF    168
TKOSC3     IQAKDGHWPAENAGPLFFTPPLVIALYISGTINTVLSEEHKKEMIRYFYNHQNEDGGWGF    169
TkOSC7     IQAKDGHWPAENAGPMFFTPPLLIAMYISGAIDTHLTKEHKTEMIRYIYNHQNEDGGWGF    168
TkLUP      IQAHDGHWPAESAGPLFFLPPLVIALYVTGAMNDILTPAHQLEIKRYIYNHQNEDGGWGL    167
TKOSC4     LQASDGHWPSANNGCHYFTPPIVMCLYITGHLDTFFSTQDKEEMLRYIYCHQNEDGGWGF    169
TKOSC5     LQADDGHWPAENAGPLYFMQPLVICLYITGHLDIVFPEEHRKEILHYMYCHQNEDGGWGF    167
TKOSC6     LQASDGHWPAENAGPLYFMQPLVICLYITGHLNIVFPEEYRKEILRYLYCHQNEDGGWGF    167
           :** **** :   *  :*  *::: :*::* ::  :    : *: :::: *********:

TKOSC1     YISGRSTMIGTALNYVGLRLLGEDDN-----DAIAKGRKWILDHGGATSIPSWGKVYLSV    234
TKOSC2     YISGRSTMIGTALNYVGLRLLGEDDN-----DAIAKGRKWILDHGGATSIPSWGKVYLSV    234
TkOSC8     HIEGHSTMFVTVLSYVSLRLLGEEKHDT--NVALIRARKWILDHGGATNVPSWGKLYLSV    226
TKOSC3     YIEGHSTMIGSVLSYVALRLLGEGEDDG--DGAIARARKWILDHGGAASIPSWGKVYLSV    227
TkOSC7     YIEGHSTMIGSALSYVALRLLGEGPNDG--NGAVTQAREWILQHGGATSIPSWGKTYLSV    226
TkLUP      HIEGHSTIFGSVLSYITLRLLGEEADSVAEDMALVKGRKWILDHGGAVGIPSWGKFWLTI    227
TKOSC4     HLEGHSIMFCTAVNYICMRMLGEGPDGGL-DGACSRARKWILDHGSVTAIPSWGKTWLSA    228
TKOSC5     HIEGHSSMFCTTLSYICMRLLGEGVDGGL-NGACTKARKWILDHGSVTAIASWGKTWLSI    226
TKOSC6     HIEGHSTMFGTTLSYICMRLLGEGPDGGL-NGACTKARKWILDHGSVTAIPSWGKTWLSI    226
           ::.*:* :: :.:.*: :*:***  .      *  :.*:***:**... : **** :*:
```

Figure 3 (cont.)

```
TKOSC1    LGVYEWAGCNPLPPEFWLFPSFLPYHPAKMWCYCRTTYMPMSYLYGTGFQGPITDLVKSL    294
TKOSC2    LGVYEWAGCNPLPPEFWLFPSFFPYHPAKMWCYCRTTYMPMSYLYGRGIQGPITDLVKSL    294
TkOSC8    LGVYEWEGCNPIPPEFWIFPEFLPFHPAKMWCYCRTAYMPMSYLYGRKFQGPITDLVLQL    286
TKOSC3    LGVYEWEGCNPLPPEFWLFPSTFPFHPAEMWCYCRTTYMPMSYLYGKRIQGPLTPLVSSL    287
TkOSC7    LGVYEWEGCNPLPPEFWLFPESLPYHPAKMWCYCRTTYMPMSYLYGKKYHGPITDLVLQL    286
TkLUP     LGVYEWGGCNPMPPEFWLMPKFFPIHPGKMLCYCRLVYMPMSYLYGKRFVGKITELVRDL    287
TKOSC4    LGLYEWSGSNPMPPEFWLLPSFLPISPGKIWCYCRMIYMPMSYLYGKRFIGPITPLILQL    288
TKOSC5    LGVCEWAGTNPMPPEFWILPSFLPMYPAKLWCYCRLVYMPMSYLYGKRFVGPITPLILQL    286
TKOSC6    LGVCEWAGTNPMPPEFWLLPSFLPMCPAKMWCYCRLVYMPMSYLYGKRFVGPITPLVLQL    286
          **: ** * **:*****::*. :*  *.:: ****  *********    * :* *: .*

TKOSC1    RKEIHVIPYHQIDWNKQRHNCCKEDLYYPHTYIQDLLWDGLHYFSEPLVSKWPLKK-LRE    353
TKOSC2    RKEIHVIPYHQIDWNKQRHNCCKEDLYYPHTYIQDLLWDGLHYFSEPLITKWPFEK-LRA    353
TkOSC8    RKEIYLTPYNEINWNEHRHKCCKEDLYYPHTIVQDLLWDGLYYLSEPLFKFWPFTK-LRE    345
TKOSC3    RKEIHLTPFEDINWNKQRNNCCKKDFYYPHSFLQDALWHSLHYLTEPVLKYWPFSK-LRG    346
TkOSC7    RKEIHPIPYHKIDWNKQRHNCCKDDLYYPHSTLQDLLWDGLNYFSEPLLKYWPFTK-LRE    345
TkLUP     RQELYTDPYDEINWNKARNTCAKEDLYYPHPFVQDMVWGVLHNVFEPVLTSRPLST-LRE    346
TKOSC4    RKELYSIPYHEVNWRKVRHLCAKEDIYYPHPWLQDLSWDTLHLAVEPILTRWPFKSMIRE    348
TKOSC5    RDELYLQPYNEINWKSIRHLCAKEDLYYPHPLLQDLMWDSLYICIEPLLNRWPLNK-LRQ    345
TKOSC6    RDELYAQPYDEINWKSIRHLCAKEDLYYPHPFLQDLMWDSLYICTEPLLNRWPLNK-LRQ    345
          *.*::  *:..::*.. *: *.*.*:****  :**  *  *    **:..  *: . :*
```

Figure 3 (cont.)

```
TKOSC1     KGLKRVLDLMQYNAEEGRYITLGCVEKSLQMMCFSALDPNGIDFKRHLARVPDYLWVAED     413
TKOSC2     KGLKRVLDLMQYNAEEGRYITLGSVEKSLQMMCFYALDPNGIDFKRHLARVPDYLWVAED     413
TkOSC8     KALKRTLELTRYNAEESRYITMASIEKGFQMMCWWAANPNGDEFKHHLARLPDYLWLAED     405
TKOSC3     RSLDRVVELMRYESEETRYMTIGCVEKSLQMMCWWAENPNGDEFKYHLARVPDYLWIAED     406
TkOSC7     KGLKRAVELMRYSAEESRYITIGCVEKSLQMMCWWAENPNGDEFKHHLARVPDYLWLAED     405
TkLUP      KALKVAMDHVHYEDKSSRYLCIGCVEKVLCLIATWVEDPNGDAYKRHLARIPDYFWVAED     406
TKOSC4     KALKTTMRHIHYEDENSRYITIGCVEKALCMLACWVEDPHGDYFKKHLSRIRDMIWVQED     408
TKOSC5     KALETTMKHIHYEDENSRYITIGSVVKVLCMLACWVEEPNGVCFKKHLARIPDYIWIAED     405
TKOSC6     KALDTTMKHIHYEDENSRYITIGSVVKPLCMLACWVEDPNGVCFKKHIARIPDYIWVAED     405
           :.*. .:   :*. :. **: :..: * : ::.   . :*:*  :* *::*: * :*: **

TKOSC1     GMKMQSFGSQLWDCTLVTQAIIASDMVEEYGDSLKKANFYLKESQIKQNPKGDFENMCRQ     473
TKOSC2     GMKMQSFGSQLWDCTLVTQAIIASDMVEEYGDSLKKANFYLKESQIKENPKGDFENMCRQ     473
TkOSC8     GMKSQTFGSQLWCSAFATQAIIASNMPEEYGDSLKKAHFFLKESQVKQNPKGDFTKMCRQ     465
TKOSC3     GMTMHSFGSQVWDCSLATQAIIASNMVEEYDDCLEKAHFYLRESQVKENPSGDFTRMCRQ     466
TkOSC7     GMKMQSFGSQIWDCTLATQAIISTDMVEEYGDSLKKAHFYIQESQIKENPSGDFSKMCRQ     465
TkLUP      GMKMQSFGCQMWDAAFAIQAILSSNLAEEYGPTLKKAHEFVKASQVRDNPPGDFSKMYRH     466
TKOSC4     GMTVQSFGSQQWDSSLSVLALIDCNMIDETGSTLKKGHEFIKNSQVRDNPSGDFKSMYRH     468
TKOSC5     GMKMQSFGSQGWDASLAIQALLATDLTDEIGSTLMKGHKFVKASQVKDNPSGYFKNMHRH     465
TKOSC6     GMKMQSFGSQKWDAGFAIQALLAADLTEENGSTLMKGHEFIKASQVKDNPSGDFKSMHRH     465
           **. ::**.* *  . :    *::  :: :* .   * *.: ::: **:::** * *  * *:
```

Figure 3 (cont.)

```
TKOSC1    FTKGAWTFSDQDQGWVVSDCTAEAVKCLLALSQMPQEISGEKVDVERLYDAINVLLYLQS   533
TKOSC2    FTKGAWTFTDQDQGWVVSDCTAEAVKCLLAMSQMPQEIAGEKVEVERLYDAINVLLYLQS   533
TkOSC8    FSKGSWTFTDQDHGWPVSDCTGEALKCLLLLSQMPEEISGEKVDNQRLYDAVNFLLHVQS   525
TKOSC3    FTKGSWTFSDQDHGWTVSDCTAEALKCLLLLSNMPKNIAGEKDDTARLYEAVNVLLYMQS   526
TkOSC7    FTKGAWTFSDQDQGWVVSDCTAEALKCLLLLSQMPEEISGEKADNERLYEAVNVLLYLQS   525
TkLUP     TSKGAWTFSIQDHGWQVSDCTAEGLKVALLYSQMSPELVGEKLETEHLYDAVNVILSLQS   526
TKOSC4    ISKGGWTYSDQDHGWQVSDCTAHGLMSCLLLSKMPLEIVGEKMETERLFDCINLLLSLQY   528
TKOSC5    ISKGSWSFSDQDHGWQGSDTTAEALKCCLLFSTMPPEIVGEKMKPEQLNDAVNVILSLQS   525
TKOSC6    ISKGSWTFSDQDHGWQISDCTAEGLKCCLLFLTMPAEIVGEHMKPEQFNDAVNVILSLQS   525
           :**.*::: **:**  ** *...:   *    *  :: **: .  :: :.:*.:* :*

TKOSC1    PETGGFAIWEAPVPKPYLEKLNPSELFADIVVEREHVECTGSIIQTLQTFKTLHPGHRQK   593
TKOSC2    PETGGFAVWEVPVPKPYLEKLNPSELFADITVEREHVECTGSIIQALQTFKTLHPGHREK   593
TkOSC8    PTTGGFAVWEKPIPHPYLQTLNPSEMFADIVVEREHVECTTSVMQALIAFQHFHSGHREK   585
TKOSC3    PVSGGFAVWEPPIPKPFLQLLNPSEIFADIVVEKEHVETTSSIIGALIEFKRVHPNHRKE   586
TkOSC7    PISGGFAIWEPPVPQPYLQMLNPSEIFADIVVEKEHVECTSSIIQALLAFKRLHPGHREK   585
TkLUP     E-NGGFPAWEPQRAYAWLEKFNPTEFFEDVLIEREYVECTSSAIQGLTLFKKLHPGHRTK   585
TKOSC4    K-NGGFSGWEPAGAPKWLEMLNPSEMFADIMIEIQYVECTSSALQALILFKKLYPEHRSQ   587
TKOSC5    K-NGGLASWEPAGSSEWLEIFNPTEFFADIVIEHEYVECTSSAIQAIVLFNKLYPQHRKK   584
TKOSC6    K-NGGLAAWEPAGSSEWLEVLNPTEFFADIVIEHEYVECTSSASQALVLFKKLYPGHRRK   584
            .**:  **      :*: :**:*:* *: :* ::** * *    :  *: .:  ** :
```

Figure 3 (cont.)

```
TKOSC1    EIEVAIEKGIRFLENRQQENGSWYGYWGICYLYGTYFVLQGLVACGQTYENSEAVRKAVK   653
TKOSC2    EIEVAIEKGIHFLENRQQENGSWYGFWGICYIYGTYFVLQGLVACGKTYENCEAVRKAVK   653
TkOSC8    EIENAIANAVRYLEEIQREDGSWYGYWGICFIYGTFFSLGGLESAGKTYNDCEAIRKGAK   645
TKOSC3    EIEYSISNGIRYLEETQWHDGSWYGYWGVCFIYGTFFALRALSTAGKTYKNNEAACKGVK   646
TkOSC7    EIEISVSKAVSFLEEKQWHDGSWYGYWGICFIYGTFFTLGGLISAGKTYNNSEAVRRAVN   645
TkLUP     EIEHCISRAIKYVEDTQESDGSWYGCWGICYTYGTWFAVDALVACGKNYHNSPALQKACK   645
TKOSC4    EVANCISNAIRFLEDTQWPDGSWYGEWGVCFTYATWFATKGLAAAGKTYEQSPTIRKATE   647
TKOSC5    EIETFLTGASGYLEKLQTKDGSWYGNWGVCFTYGTWFGIGGLTAVGKTFENCQAIQKAVK   644
TKOSC6    EIESFLTGASGYLEKIQMEDGSWYGNWGVCFTYGTWFALGGLTAVGKTFENCLAIRKAVK   644
          *:    :   .   ::*. *   :***** **:*: *.*:*    .* : *:.:.:  :  :. :

TKOSC1    FFLSTQNSEGGWGENFESCPQEKFIPLEGNRTNFVQTSWAMLGLLCGGQAERDPTPLHKA   713
TKOSC2    FFLSTQNSEGGWGEHFESCPQEKFIPLEGNRTHFVHTSWAMLGLLYGGQVERDPTPLHKA   713
TkOSC8    FLLSTQNEEGGWGESYKSCPSEVYTPLDGNKTNIVQTSWAMLGLMSSGQAERDPTPLHKA   705
TKOSC3    FLLSIQNEEGGWGESLLSCPTEVYTPLDGNQTNLVQTSWAMLGLLFGGQVDRDPTPLHRA   706
TkOSC7    FFLSTQNEEGGWGESIKSCPSEVYTPLDENRTNLVQTSWAMLGLMLGGQAERDPTPLHKA   705
TkLUP     FLLSKQLPDGGWGESYLSSSNKVYTNLEGNRSNLVHTSWALISLIKAGQAEIDPTPISNG   705
TKOSC4    FLLKHQQEDGGWGESYLSCPNLEFTSLEESRSNVVQTSWCLMSLIQCGQAERDLTPIHRG   707
TKOSC5    FLLETQLEDGGWGESYKSCPEKIYIPLEGGRSNLVHTSWAMIGLIQSQWMERDSTPIHKA   704
TKOSC6    FLLETQLEDGGWGESYKSCPEKRYVPLEEGRSNLVHTAWGMMGLIHSQQMERDPMPLHKA   704
          *:*. *   :*****    *.     :   *: .:::.*:*:* ::.*:      : *  *: ..
```

Figure 3 (cont.)

```
TKOSC1
AKLLINGQMDNGDFPQQEITGVYMKNCMLHYAEYRNTFPLWALGEYRKRVWLAKQET-
-      770
TKOSC2
SKLLINGQTDNGDFPQQEITGVYNKNCMLHYAEYRNTFPLWALGEYRKRVWLAKQET-
-      770
TkOSC8
ARILINAQMDNGDFPQQEMTGAAMRNCMLHYPLYSNIFPLLALSKYRQQFWDK-----
-      758
TKOSC3
AKLLINAQMDNGDFPQQEITGVYMKNCLLLYAQYRNIFPLWALGEYRKRVWSIKKGIQ
N      765
TkOSC7
AKILINSQMDNGDFPQQEITGVYMKNCMLHYAEYRNIFPLWALGEYRKRVWVN-----
-      758
TkLUP
VRLLINSQMEEGDFPQQEITGVFMKNCNLNYSSYRNIFPIWALGEYRRIVQNI-----
-      758
TKOSC4
AKFLINSQMEDGDFPQKEITGSFRKNCMLHYACHRNIFPMWALAEYKNRVSKII----
-      761
TKOSC5
ARLLINSQLENGDFPQQEITGVFMKNCMLHYALYRNIYPMWALADYRKKVLSTCKK--
-      760
TKOSC6
AKLLINSQLENGDFPQQKIAGVFKMNCMLHYALYRNIFPMWALADYRKHVLKGI----
-      758
              ::***.*  ::*****::::*      **  *  *    :  *  :*:
**..*:. .
```

METHOD TO OBTAIN LOW TRITERPENE/TRITERPENOID-CONTAINING NATURAL RUBBER LATEX

PRIORITY CLAIM

This application claims priority to International Application No. PCT/EP2019/080668, filed Nov. 8, 2019, which claims priority to European Application No. 18205121.9, filed Nov. 8, 2018, wherein the contents of said applications are incorporated herein by reference in their entireties. Also, the entire contents of the ASCII text file entitled "IPM0119US Sequence Listing.txt" created on May 2, 2021, and having a size of 107 kilobytes, is incorporated herein by reference.

TECHNICAL FIELD OF THE INVENTION

The present invention provides a method of reducing or eliminating the content of triterpenes and/or triterpenoids of latex or rubber from a laticiferous plant or part thereof, comprising genetically modifying the laticiferous plant or part thereof, such that the activity of at least one oxidosqualene cyclase is reduced or eliminated. Further, the present invention provides a laticiferous plant or part thereof being genetically modified such that the activity of at least one oxidosqualene cyclase is reduced or eliminated, compared to the respective wild-type or untreated laticiferous plant or part thereof. Additionally, the present invention also includes an RNAi being specifically directed against a mRNA transcript of at least one oxidosqualene cyclase, for use in said method of reducing or eliminating the content of triterpenes and/or triterpenoids of latex or rubber from a laticiferous plant or part thereof.

BACKGROUND ART

Supplied by the mevalonic acid (MVA) pathway oxidosqualene cyclases (OSCs) catalyse the cyclisation of 2,3-oxidosqualene (Abe, 2007; Thimmappa et al., 2014). This leads to the production of triterpenes, 30-carbon compounds, which comprise nearly 200 different scaffolds in plants (Xu et al., 2004). Tailoring enzymes can further modify triterpenes via acetylation, oxidation or by adding sugar chains, resulting in a huge diversity with more than 20,000 known triterpenoids (Xu et al., 2004; Thimmappa et al., 2014).

Due to the cyclisation reaction type, a differentiation between two classes of triterpenoids exist: In the first class chair-boat-chair conformation occurs and results initially in the production of cycloartenol, which is a phytosterol intermediate (Abe, 2007; Thimmappa et al., 2014). The resulting sterols function e.g. as membrane compounds or signalling molecules. Therefore, they are important for plant development and growth (Hartmann, 1998; Clouse, 2002). In the second class chair-chair-chair conformation results among others in the formation of pentacyclic triterpenes such as lupeol and β-amyrin (Thimmappa et al., 2014). A large number of pentacyclic triterpenes show antimicrobial and antifungal characteristics and play a role in plant defence.

Due to this characteristics, they are interesting for broad applications in food, cosmetics and pharmaceutical industries (Augustin et al., 2011; Osbourn et al., 2011; Moses et al., 2014). In dandelion, a high amount of pentacyclic triterpenes mainly occurs in roots, more precisely in laticifers, a specialised cell type, which produces a milky sap containing high concentrations of secondary metabolites (Furuno et al., 1993; Akashi et al., 1994). This cell type is also the place for poly(cis-1,4-isoprene) biosynthesis, the main component of natural rubber (NR) (Hagel et al., 2008). NR is an important biopolymer that is used for the production of more than 40,000 consumables, including e.g. tyres and medical devices (Davis, 1997; Mooibroek and Cornish, 2000; Hagel et al., 2008). High quality NR for commercial use usually derives from the rubber tree *Hevea brasiliensis*; however, it can also be extracted from the roots of the Russian dandelion, *T. koksaghyz*. NR derived from dandelion incorporates small amounts of additives like fatty acids, proteins and triterpenes, which have impact on the properties of NR (Nor and Ebdon, 1998; Sakdapipanich, 2007; Schulze Gronover et al., 2011).

Since *T. koksaghyz* is a self-incompatible, sexually reproductive plant, it produces heterogenic offspring (Krotkov, 1945; Schulze Gronover et al., 2011). Consequently, the amount of pentacyclic triterpenes varies between single plants, which is not desirable for industrial applications.

Moreover, Jungkong et al. and Ikeda et al. have shown that substances such as triterpenes generally have an important influence on the properties of natural rubber or latex.

Accordingly, there is not only the need for a consistent level of triterpenes and/or triterpenoids, but also for a reduced content of triterpenes and/or triterpenoids of latex or rubber from laticiferous plants. The present invention aims to solve this problem.

SUMMARY OF THE INVENTION

The problem is solved by the subject-matter as defined in the claims and as defined herein.

In one embodiment, the present invention provides a method of reducing or eliminating the content of triterpenes and/or triterpenoids of latex or rubber from a laticiferous plant or part thereof, comprising genetically modifying the laticiferous plant or part thereof, such that the activity of at least one oxidosqualene cyclase is reduced or eliminated, compared to the respective wild-type or untreated laticiferous plant or part thereof. The laticiferous plant or part thereof can also be a progeny of the respective laticiferous plant.

In a preferred embodiment thereof, the laticiferous plant or part thereof is genetically modified by at least one heterologous nucleotide sequence that is capable of reducing or eliminating the activity of the at least one oxidosqualene cyclase, and/or wherein the laticiferous plant or part thereof is genetically modified by subjecting it to and/or incubating it with agents, which are capable of reducing or eliminating the activity of the at least one oxidosqualene cyclase. The term "is/are capable of reducing or eliminating" is also to be considered compared to the respective wild-type or untreated laticiferous plant, progeny thereof or part thereof.

In a further embodiment, the at least one heterologous nucleotide sequence encodes at least one RNAi that interferes with the mRNA encoding the at least one oxidosqualene cyclase, with the proviso that the at least one RNAi is capable of reducing or eliminating the activity of the at least one oxidosqualene cyclase. The term "is/are capable of reducing or eliminating" is also to be considered compared to the respective wild-type or untreated laticiferous plant, progeny thereof or part thereof.

In one embodiment of the method of the present invention, the at least one RNAi is specifically directed against the mRNA transcript of the at least one oxidosqualene cyclase, preferably wherein the at least one RNAi comprises or consists of a nucleotide sequence according to SEQ ID NO:

1 and/or comprises or consists of a nucleotide sequence according to SEQ ID NO: 2 and/or comprises or consists of a nucleotide sequence being at least 60%, 70%, 80%, 90%, 95% or 99% identical to SEQ ID NO: 1 or SEQ ID NO: 2.

In a further embodiment of the method of the present invention, the laticiferous plant or part thereof is selected from the group of plant families consisting of Apocynaceae, Asteraceae, Euphorbiaceae and Moraceae. The laticiferous plant or part thereof can also be the progeny of the respective laticiferous plant in this embodiment.

In a specific embodiment of the method of the present invention, the at least one oxidosqualene cyclase is selected from the group consisting of oxidosqualene cyclase 1 according to SEQ ID NO: 4, the oxidosqualene cyclase 2 according to SEQ ID NO: 6, the oxidosqualene cyclase 3 according to SEQ ID NO: 8, the oxidosqualene cyclase 4 according to SEQ ID NO: 10, the oxidosqualene cyclase 5 according to SEQ ID NO: 12, the oxidosqualene cyclase 6 according to SEQ ID NO: 14, the oxidosqualene cyclase 7 according to SEQ ID NO: 16, the oxidosqualene cyclase 8 according to SEQ ID NO: 18, the lupeol synthase according to SEQ ID NO: 20 and an amino acid sequence being at least 60%, 70%, 80%, 90%, 95% or 99% identical to SEQ ID NOs: 4, 6, 8, 10, 12, 14, 16, 18 or 20.

In one embodiment of the method of the present invention, the part of the laticiferous plant is selected from the group consisting of cells, tissues, organs, roots, stems, branches, leaves, exudates, latex, and mixtures thereof.

The present invention also includes a laticiferous plant or part thereof being genetically modified such that the activity of at least one oxidosqualene cyclase is reduced or eliminated, compared to the respective wild-type or untreated laticiferous plant or part thereof. The term "is/are capable of reducing or eliminating" is also to be considered compared to the respective wild-type or untreated laticiferous plant, progeny thereof or part thereof.

In one embodiment, such a laticiferous plant or part thereof is genetically modified by at least one heterologous nucleotide sequence that is capable of reducing or eliminating the activity of the at least one oxidosqualene cyclase, or wherein the laticiferous plant or part thereof is genetically modified by subjecting it to and/or incubating it with agents, which are capable of reducing or eliminating the activity of the at least one oxidosqualene cyclase. The term "is/are capable of reducing or eliminating" is also to be considered compared to the respective wild-type or untreated laticiferous plant, progeny thereof or part thereof.

In another embodiment, in the laticiferous plant or part thereof of the present invention, the at least one heterologous nucleotide sequence encodes at least one RNAi that interferes with the mRNA encoding the at least one oxidosqualene cyclase with the proviso that the at least one RNAi is capable of reducing or eliminating the activity of the at least one oxidosqualene cyclase. The laticiferous plant or part thereof can also be the progeny of the respective laticiferous plant. The term "is/are capable of reducing or eliminating" is also to be considered compared to the respective wild-type or untreated laticiferous plant, progeny thereof or part thereof.

In a further embodiment, in the laticiferous plant or part thereof of the present invention, the at least one RNAi is specifically directed against the mRNA transcript of the at least one oxidosqualene cyclase, preferably wherein the at least one RNAi comprises or consists of a nucleotide sequence according to SEQ ID NO: 1 and/or comprises or consists of a nucleotide sequence according to SEQ ID NO: 2 and/or comprises or consists of a nucleotide sequence being at least 60%, 70%, 80%, 90%, 95% or 99% identical to SEQ ID NO: 1 or SEQ ID NO: 2.

In a further embodiment, the laticiferous plant or part thereof is selected from the group of plant families consisting of Apocynaceae, Asteraceae, Euphorbiaceae, Moraceae and crossings thereof, preferably wherein the laticiferous plant or part thereof is selected from the group consisting of *Agoseris glauca, Apocynum venetum, Chrysothamnus graveolens, Chrysothamnus nauseosus, Chrysothamnus viscidiflorus, Funtumia elastica, Parthenium argentatum, Scorzonera acanthoclada, Scorzonera albicaulis, Scorzonera divaricate, Scorzonera hissaricata, Scorzonera racemosa, Scorzonera tau-saghyz, Scorzonera tragapogonoides, Scorzonera turkestania, Scorzonera virgate, Solidago canadensis scabra, Solidago fistulosa, Solidago leavenworthii, Solidago rigida, Sonchus oleraceus, Taraxacum brevicomiculaturn, Taraxacum hybernum, Taraxacum koksaghyz, Taraxacum megalorrhizon, Taraxacum officinale* and crossings thereof. In a further embodiment, the laticiferous plant or part thereof is selected from the group of plant families consisting of Apocynaceae, Asteraceae, Euphorbiaceae, Moraceae and crossings thereof, preferably wherein the laticiferous plant or part thereof is selected from the group consisting of *Agoseris glauca, Apocynum venetum, Chrysothamnus graveolens, Chrysothamnus nauseosus, Chrysothamnus viscidiflorus, Cichorium intybus L., Funtumia elastica, Parthenium argentatum, Scorzonera acanthoclada, Scorzonera albicaulis, Scorzonera divaricate, Scorzonera hissaricata, Scorzonera racemosa, Scorzonera tau-saghyz, Scorzonera tragapogonoides, Scorzonera turkestania, Scorzonera virgate, Solidago canadensis scabra, Solidago fistulosa, Solidago leavenworthii, Solidago rigida, Sonchus oleraceus, Taraxacum brevicomiculaturn, Taraxacum hybernum, Taraxacum koksaghyz, Taraxacum megalorrhizon, Taraxacum officinale* and crossings thereof. In a more preferred embodiment, the laticiferous plant or part thereof is *Cichorium intybus* L.

In a further embodiment of the present invention, in the laticiferous plant or part thereof the at least one oxidosqualene cyclase is selected from the group consisting of oxidosqualene cyclase 1 according to SEQ ID NO: 4, the oxidosqualene cyclase 2 according to SEQ ID NO: 6, the oxidosqualene cyclase 3 according to SEQ ID NO: 8, the oxidosqualene cyclase 4 according to SEQ ID NO: 10, the oxidosqualene cyclase 5 according to SEQ ID NO: 12, the oxidosqualene cyclase 6 according to SEQ ID NO: 14, the oxidosqualene cyclase 7 according to SEQ ID NO: 16, the oxidosqualene cyclase 8 according to SEQ ID NO: 18, the lupeol synthase according to SEQ ID NO: 20 and an amino acid sequence being at least 60%, 70%, 80%, 90%, 95% or 99% identical to SEQ ID NOs: 4, 6, 8, 10, 12, 14, 16, 18 or 20.

The present invention is also directed to a RNAi being specifically directed against a mRNA transcript of at least one oxidosqualene cyclase, preferably wherein the RNAi comprises or consists of a nucleotide sequence according to SEQ ID NO: 1 and/or comprises or consists of a nucleotide sequence according to SEQ ID NO: 2 and/or comprises or consists of a nucleotide sequence being at least 60%, 70%, 80%, 90%, 95% or 99% identical to SEQ ID NO: 1 or SEQ ID NO: 2, for use in a method of reducing or eliminating the content of triterpenes and/or triterpenoids of latex or rubber from a laticiferous plant or part thereof.

The invention will be better understood with reference to the detailed description when considered in conjunction with the drawings, the non-limiting examples and the accompanying claims.

BRIEF DESCRIPTION OF THE DRAWINGS

FIG. 1(*a*) shows normalised TkOSC1 expression of 9 to 16 weeks old wild-type (empty boxes, n=4), TkOSC1-RNAi (diagonally striped boxes, n=7) and TkOSC-RNAi plants (horizontally striped boxes, n=12) was determined by qRT-PCR using the constitutively expressed genes elongation factor 1a (TkEF1a) and ribosomal protein L27 (TkRP) from *T. koksaghyz*. FIG. 1(*b*) shows the expression analysis of TkOSC2-3, TkOSC5-6 and TkLUP, and FIG. 1(*c*) shows the one of TkSQS1 and TkSQE2. Therefore, three plants of each group were analysed. Quantification by GC/MS of single pentacyclic triterpenes shown in FIG. 1(*d*) and triterpene subclasses shown in FIG. 1(*e*) was performed on triterpene extracts from freeze-dried root material harvested from 5- to 7-month-old plants. Precursors=squalene and 2,3-oxidosqualene; sterol intermediates=cycloartenol and 24-methylene cycloartanol; pentacyclic triterpenes=taraxerol/n.i. (not identified pentacyclic triterpene), β-amyrin, lupeol, α-amyrin/lup-19(21)-en-3-ol, TkOSC3-product 1, TkOSC3-product 2, n.i.1 and taraxasterol; sterols=campesterol, stigmasterol and sitosterol; bar charts with appropriate standard deviations; boxplots: boxes=25%-75%, bar=median, square=average, hash=outlier, whisker=1.5 interquartile range; asterisks=statistical significance compared to *T. koksaghyz* wild-type (two-tailed t-test was applied for n=3, Mann-Whitney U test was applied for n>3, *=p<0.05, **=p<0.01).

FIG. 3: Alignment of TkOSC1-8 and TkLUP amino acid sequences. The alignment was created with Clustal Omega (ebi.ac.uk/Tools/msa/clustalo/). Dashes represent gaps in aligned sequences. Conserved sites include a domain for product determination (M (W/Y) CY (C/S) R-motif, dashed box; e.g., SEQ ID NO: 6, amino acids 264-269), a region involved in substrate binding and cyclization (DCTAE-motif, solid box; e.g., SEQ ID NO: 8, amino acids 485-489) and repeated QW-motifs (underlined) involved in stabilization of carbocationic intermediates, which are localized near the 5' and 3'-end of the proteins. TkOSC1 relates to SEQ ID NO: 4, TKOSC2 relates to SEQ ID NO: 6, TKOSC3 relates to SEQ ID NO: 8, TkOSC4 relates to SEQ ID NO: 10, TkOSC5 relates to SEQ ID NO: 12, TKOSC6 relates to SEQ ID NO: 14, TkOSC7 relates to SEQ ID NO: 16, TKOSC8 relates to SEQ ID NO: 18 and TkLUP relates to SEQ ID NO: 20.

DETAILED DESCRIPTION OF THE INVENTION

The invention is based on the surprising finding that the triterpene and/or triterpenoid content of latex or rubber can be reduced or even completely eliminated by the method according to the present invention. This allows the provision of a laticiferous plant, progeny thereof or part thereof, which is characterized by a low or even absent triterpene and/or triterpenoid content. This provides advantages for the products or materials, which are produced with rubber or latex received from these laticiferous plants, progeny thereof or parts thereof according to the present invention, for example with regard to durability, robustness and longevity.

Example 2 shows that a knockdown of oxidosqualene cyclases (OSC) is possible by RNAi (RNA interference)-mediated knockdown. Example 3 shows that the knockdown of OSCs results in the reduction of the pentacyclic triterpenoid content (triterpenes and triterpenoids) in root and rubber of a laticiferous plant such as *Taraxacum koksaghyz*. For example, with regard to the root, the following observations were made: The pentacyclic triterpenoids were strongly affected in the transgenic lines (FIG. 1(*d*) and FIG. 1(*e*)). As a result, the total amount was reduced from 4.6 mg/g dry root weight in wild-type plants to 2.8 mg/g dry root weight in TkOSC1-RNAi plants comprising a nucleotide sequence of SEQ ID NO: 2 and to 2.6 mg/g in TkOSC-RNAi plants comprising a nucleotide sequence of SEQ ID NO: 1. Especially, the most abundant triterpenes, taraxasterol, β-amyrin and one unidentified triterpene (n.i.1), were remarkably reduced with a higher level of significance in TkOSC-RNAi plants. Besides the pentacyclic triterpenes, further compounds were measured via GC/MS (FIG. 1(*e*), Table 3). It was found that precursors like squalene and 2,3-oxidosqualene accumulated significantly in the transgenic lines, with a higher level of significance in TkOSC-RNAi plants. Additionally, cycloartenol and 24-methylene cycloartanol, two sterol intermediates, were detected in both transgenic lines, with an average of 0.1 mg/g dry root weight in TkOSC1-RNAi plants and 0.9 mg/g dry root weight in TkOSC-RNAi plants. Sterols including campesterol, stigmasterol and sitosterol were detected to equal amounts of about 0.5 mg/g dry root weight in all plants and were not affected by the knock-down. In sum, the total triterpene content including precursors, sterol intermediates, sterols and pentacyclic triterpenes was significantly reduced in transgenic RNAi lines to about two-thirds with a higher level of significance in TkOSC-RNAi plants (FIG. 1(*e*)). In conclusion, it can be claimed that an OSC knockdown strongly reduces triterpenes in dandelion root and NR. For example, it could be observed that in dandelion root the total content of triterpenes could be reduced to a total content of 70%, while in dandelion NR the total content of triterpenes could be reduced to a total content of 44%.

Figure 2:
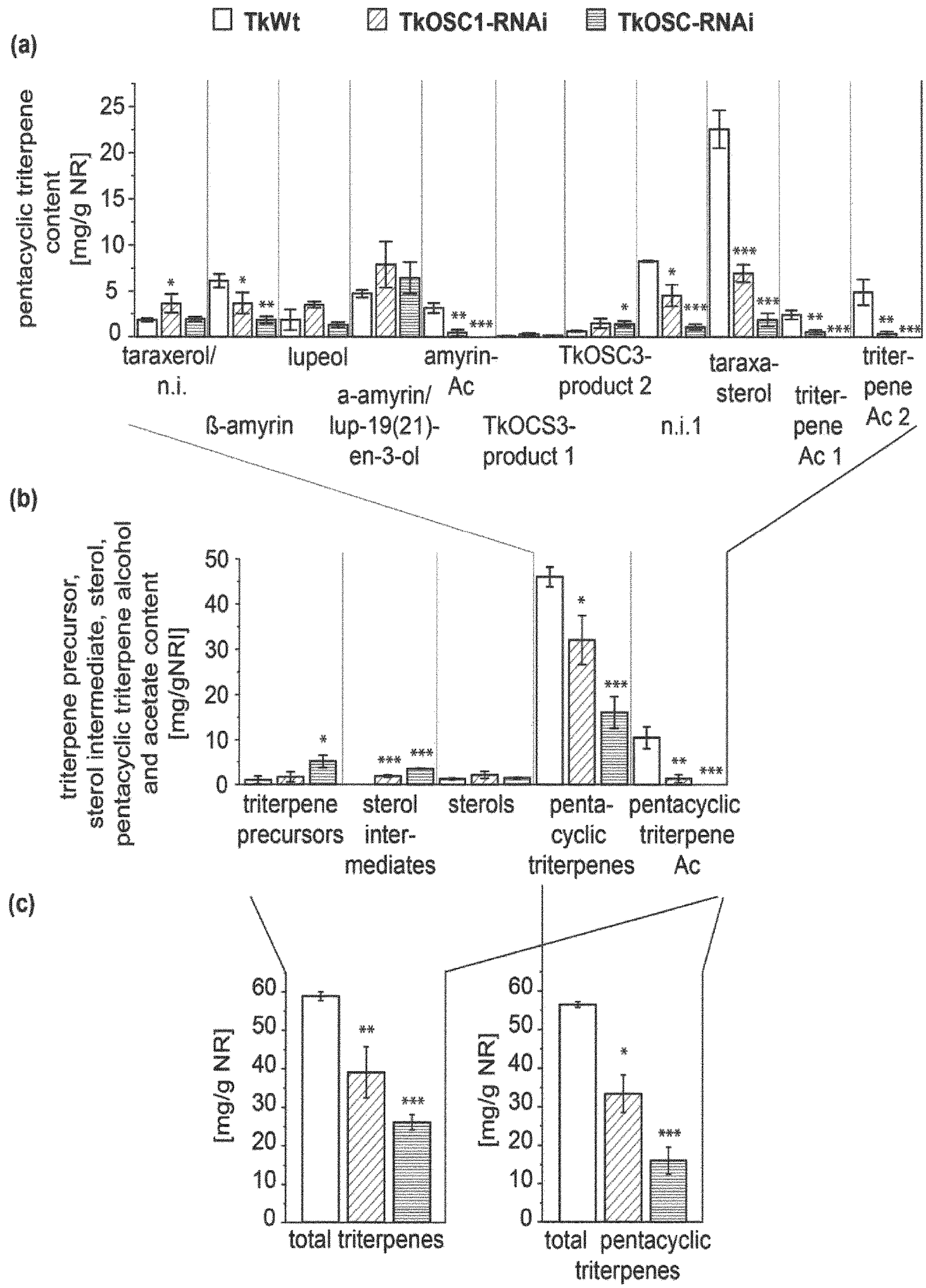
FIG. 2: Analysis of triterpenes in NR extracts from TkOSC1- and TkOSC-RNAi lines. NR was extracted from independent wild-type (empty boxes, n=3), TkOSC1-RNAi (diagonally striped boxes, n=3) and TkOSC-RNAi plants (horizontally striped boxes, n=3), the corresponding triterpene extracts were measured via GC/MS. Pentacyclic triterpenes (shown in FIG. 2(*a*)), triterpene subclasses (shown in FIG. 2(*b*)), total triterpenoids and total pentacyclic triterpenes (shown in FIG. 2(*c*)) were depicted in bar charts with appropriate standard deviations; asterisks indicate statistical significant differences between root and NR (two-tailed t-test, *=p<0.05, =p<0.01, *=p<0.001). Precursors=squalene and 2,3-oxidosqualene; sterol intermediates=cycloartenol and 24-methylene cycloartanol; pentacyclic triterpenes=taraxerol, β-amyrin, lupeol, α-amyrin, lup-19(21)-en-3-ol, taraxasterol, OSC3-products and not identified (n.i.) triterpenes; sterols=campesterol, stigmasterol and sitosterol; acetate=Ac.

For example, with regard to the NR, the following observations were made: After rubber extraction from root material of wild-type, TkOSC1-RNAi and TkOSC-RNAi plants, the triterpenes in NR extracts were isolated by acetone extraction and quantified in relation to NR weight (FIG. 2, Table 4). The crude acetone extracts contained acetate derivatives of different triterpenes. Those acetates as well as the predominant triterpenes in latex (taraxasterol, β-amyrin and n.i.1) were strongly reduced compared to wild-type plants with a higher level of significance in TkOSC-RNAi plants compared to TkOSC1-RNAi plants (FIGS. 2(*a*) and 2(*b*)). The average amount of total pentacyclic triterpenes in wild-type plants with 56.6 mg/g NR was reduced to 33.4 mg/g NR in TkOSC1-RNAi lines or even to 16.1 mg/g NR in TkOSC-RNAi lines (FIG. 2(*c*)). In contrast to the reduced pentacyclic triterpene content, increasing amounts of triterpene precursors as well as sterol intermediates were again detected in RNAi-lines compared to wild-type, while equal amounts of sterols were measured in all three groups. However, total triterpenoid amount was still significantly decreased to two thirds in TkOSC1-RNAi NR and to less than the half in TkOSC-RNAi NR (FIG. 2(*b*)). In conclusion, it can be stated that an OSC knockdown strongly reduces triterpenes/triterpenoids in dandelion root and NR.

The present invention provides a method of reducing or eliminating the content of triterpenes and/or triterpenoids of latex or rubber from a laticiferous plant or part thereof, comprising genetically modifying the laticiferous plant or part thereof, such that the activity of at least one oxidosqualene cyclase is reduced or eliminated, compared to the respective wild-type or untreated laticiferous plant or part thereof.

In another embodiment, the present invention provides a method of reducing the content of triterpenes and/or triterpenoids of latex or rubber from a laticiferous plant or part thereof, comprising genetically modifying the laticiferous plant or part thereof, such that the activity of at least one oxidosqualene cyclase is reduced, compared to the respective wild-type or untreated laticiferous plant or part thereof.

In a further embodiment, the present invention provides a method of eliminating the content of triterpenes and/or triterpenoids of latex or rubber from a laticiferous plant or part thereof, comprising genetically modifying the laticiferous plant or part thereof, such that the activity of at least one oxidosqualene cyclase is eliminated, compared to the respective wild-type or untreated laticiferous plant or part thereof.

In another embodiment, the present invention provides a method of reducing or eliminating the content of triterpenes and/or triterpenoids of rubber from a laticiferous plant or part thereof, comprising genetically modifying the laticiferous plant or part thereof, such that the activity of at least one oxidosqualene cyclase is reduced or eliminated, compared to the respective wild-type or untreated laticiferous plant or part thereof.

In a further embodiment, the present invention provides a method of reducing or eliminating the content of triterpenes and/or triterpenoids of latex from a laticiferous plant or part thereof, comprising genetically modifying the laticiferous plant or part thereof, such that the activity of at least one oxidosqualene cyclase is reduced or eliminated, compared to the respective wild-type or untreated laticiferous plant or part thereof.

In another embodiment, the present invention provides a method of reducing the content of triterpenes and/or triterpenoids of rubber from a laticiferous plant or part thereof, comprising genetically modifying the laticiferous plant or part thereof, such that the activity of at least one oxidosqualene cyclase is reduced, compared to the respective wild-type or untreated laticiferous plant or part thereof.

In another embodiment, the present invention provides a method of reducing the content of triterpenes and/or triterpenoids of latex from a laticiferous plant or part thereof, comprising genetically modifying the laticiferous plant or part thereof, such that the activity of at least one oxidosqualene cyclase is reduced, compared to the respective wild-type or untreated laticiferous plant or part thereof.

In a further embodiment, the present invention provides a method of eliminating the content of triterpenes and/or triterpenoids of rubber from a laticiferous plant or part thereof, comprising genetically modifying the laticiferous plant or part thereof, such that the activity of at least one oxidosqualene cyclase is eliminated, compared to the respective wild-type or untreated laticiferous plant or part thereof.

In a further embodiment, the present invention provides a method of eliminating the content of triterpenes and/or triterpenoids of latex from a laticiferous plant or part thereof, comprising genetically modifying the laticiferous plant or part thereof, such that the activity of at least one oxidosqualene cyclase is eliminated, compared to the respective wild-type or untreated laticiferous plant or part thereof.

In a further embodiment, the present invention provides a method of reducing or eliminating the content of triterpenes and/or triterpenoids of latex or rubber from a laticiferous plant, progeny thereof or part thereof, comprising genetically modifying the laticiferous plant or part thereof, such that the activity of at least one oxidosqualene cyclase is reduced or eliminated, compared to the respective wild-type or untreated laticiferous plant or part thereof.

"Triterpenes" as used herein relate to a class of chemical compounds composed of three terpene units with the molecular formula $C_{30}H_{48}$; they may also be thought of as comprising of six isoprene units. Animals, plants and fungi all produce triterpenes, including squalene, the precursor to all steroids. Triterpenes as such do not comprise heteroatoms.

"Triterpenoids" as used herein relate to triterpenes, which possess at least one heteroatom. Examples of triterpenoids include, but are not limited to, taraxerol, β-amyrin, lupeol, α-amyrin, lup-19(21)-en-3-ol or taraxasterol. Triterpenes and triterpenoids may also be summarized as pentacyclic triterpene content of the laticiferous plant or part thereof. Triterpenes and triterpenoids may also be summarized as pentacyclic triterpene content of the method of the present invention.

As used herein, the term "progeny" or "progenies" refers in a non limiting manner to offspring or descendant plants. According to certain embodiments, the term "progeny" or "progenies" refers to plants developed or grown or produced from the respective laticiferous plants. Those plants grown under consideration of the methods according to the present invention as described herein are characterized by a reduced or eliminated content of triterpenes and/or triterpenoids of the latex or rubber, which is gained from these laticiferous plant progeny or progenies.

For the method of the present invention, it is necessary that the activity of the oxidosqualene cyclase is reduced or eliminated compared to the respective wild-type or untreated laticiferous plant, progeny thereof or part thereof. There are many possible ways to achieve this reduction or elimination of oxidosqualene cyclase activity including reducing/eliminating the amount of the enzyme and/or reducing/eliminating the activity of the enzyme oxidosqualene cyclase. Ways to reduce the oxidosqualene cyclase amount, i.e. reduction of the expression of oxidosqualene cyclase, are known to a person skilled in the art and include the use gene knockdown technologies such as RNA interference (RNAi) or modification of regulatory elements. The expression of the oxidosqualene cyclase can be eliminated e.g. by knocking out the gene(s) encoding an oxidosqualene cyclase. Examples of technologies for knocking out genes include homologous recombination or site-specific nucleases such as Zinc-Finger nucleases, TALEN or CRISPR.

However, a "reduction of the content of triterpenes and/or triterpenoids" or "the content of triterpenes and/or triterpenoids is reduced" or "being capable of reducing the content of triterpenes and/or triterpenoids" means in the context of the present invention and as used herein that the content of triterpenes and/or triterpenoids contained in a laticiferous plant, progeny thereof or part thereof is reduced for at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94% or 95% compared to the wild-type or untreated laticiferous plant, progeny thereof or part thereof, meaning without being genetically modified or before being genetically modified.

An "elimination of the content of triterpenes and/or triterpenoids" or "the content of triterpenes and/or triterpenoids is eliminated" or "being capable of eliminating the content of triterpenes and/or triterpenoids" means in the context of the present invention and as used herein that the content of triterpenes and/or triterpenoids contained in a laticiferous plant, progeny thereof or part thereof is reduced for at least 95.1%, 95.2%, 95.3%, 95.4%, 95.5%, 95.6%, 95.7%, 95.8%, 95.9%, 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, 99.9% or even 100.00% compared to the wild-type or untreated laticiferous plant, progeny thereof or part thereof, meaning without being genetically modified or before being genetically modified.

The "activity of at least one oxidosqualene cyclase is reduced" or the "reduction of the activity of the at least one oxidosqualene cyclase" or "being capable of reducing the activity of at least one oxidosqualene cyclase" means in the context of the present invention and as used herein that the activity of the at least one oxidosqualene cyclase contained in a laticiferous plant, progeny thereof or part thereof is reduced for at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94% or 95%, compared to the wild-type or untreated laticiferous plant, progeny thereof or part thereof, meaning without being genetically modified or before being genetically modified.

The "activity of at least one oxidosqualene cyclase is eliminated" or an "elimination of the activity of the at least one oxidosqualene cyclase" or "being capable of eliminating the activity of at least one oxidosqualene cyclase" means in the context of the present invention and as used herein that the activity of at least one oxidosqualene cyclase of the laticiferous plant, progeny thereof or part thereof is reduced for at least 95.1%, 95.2%, 95.3%, 95.4%, 95.5%, 95.6%, 95.7%, 95.8%, 95.9%, 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, 99.9% or even 100.00%, compared to the wild-type or untreated laticiferous plant, progeny thereof or part thereof, meaning without being genetically modified or before being genetically modified.

"Latex" or "latexes" as used herein relate to products well known to those skilled in the art. They consist of aqueous dispersions of water-insoluble polymers. These fluid systems contain, as dispersed phase, particles of polymers consisting of several entangled polymer chains in an aqueous dispersion medium. The diameter of the polymer particles within the dispersion can range between 5 nm and 10 μm. These latexes find many applications, in particular as additives in formulations for paints, for paper (coating mixtures, bulk paper) or in formulations intended to be applied in the building industry (adhesive, bonding agents, smoothing coatings, etc.). They impart important properties on these formulations by virtue, for example, of their binding power and their film-forming power.

"Rubber" as used herein relates to natural rubber, component of the latex of the rubber tree *Hevea brasiliensis* and of other rubber-supplying plants. It contains polyisoprene, which is present very finely dispersed in the aqueous phase and represents the actual natural rubber, and also, as secondary components, proteins, sugars, polysaccharides and inorganic salts. These secondary components, in particular, form a culture medium for bacteria, which multiply quickly in the latex and cause it to perish, which finally results in coagulation, i.e., in the precipitation of the polymer phase. There are often long distances, and possibly relatively long storage times, between extraction at the rubber plantations and further processing. If processing to solid rubber does not take place on site, the latex is normally treated with suitable agents immediately after extraction. This treatment is to provide protection against bacterial attack of the latex and for stabilization of the physico-chemical properties of the latex.

The term "laticiferous" or "laticifers" as used in the context of the present invention and as used herein is related to or is a type of elongated secretory cells found in the leaves and/or stems of plants that produce latex and rubber as secondary metabolites. Laticifers may be divided into: Articulated laticifers, i.e., composed of a series of cells joined together, or non-articulated laticifers, consisting of one long coenocytic cell. Non-articulated laticifers begin their growth from the meristematic tissue of the embryo, termed the laticifer initial, and can exhibit continual growth throughout the lifetime of the plant. Laticifer tubes have irregularly edged walls and a larger inner diameter than the surrounding parenchyma cells. In the development of the cell, elongation occurs via karyokinesis and no cell plate develops resulting in coenocytic cells, which extend throughout the plant. These cells can reach up to tens of centimeters long and can be branched or unbranched. They are thought to have a role in wound healing and as defense against herbivory, as well as pathogen defense, and are often used for taxonomy.

The term "wild-type" plant, respectively laticiferous plant, or "untreated" plant, respectively laticiferous plant, refers in the context of the present invention and as used herein to plants, which serve as starting material for the production of the plants described herein and according to the present invention, i.e. plants of which the genetic information—apart from the genetic modification introduced—is identical to the genetic information of the plant of the present invention. This specifically means herein that the "wild-type" plant, respectively laticiferous plant, or "untreated" plant, respectively laticiferous plant, is without being genetically modified or before being genetically modified as described herein.

In an embodiment of the method of the present invention, the laticiferous plant or part thereof is genetically modified by at least one heterologous nucleotide sequence that is capable of reducing or eliminating the activity of the at least one oxidosqualene cyclase. In one further embodiment of the method of the present invention, the laticiferous plant, progeny thereof or part thereof is genetically modified by at least one heterologous nucleotide sequence that is capable of reducing or eliminating the activity of the at least one oxidosqualene cyclase. The term "genetically modified" means, as used herein and in the context of the present invention, that the laticiferous plant, progeny thereof or part thereof comprises one or more heterologous nucleotide sequence(s) that is/are capable of reducing or eliminating the activity of the at least one oxidosqualene cyclase. The term "is/are capable of reducing or eliminating" is also to be considered compared to the respective wild-type or untreated laticiferous plant, progeny thereof or part thereof as defined above. A "heterologous nucleotide sequence" or "heterologous nucleic acid" is a sequence that is not naturally occurring in the respective nucleic acid. Generally, the heterologous nucleic acid comprises an open reading frame that encodes a polypeptide or non-translated RNA of interest (e.g., for delivery to a cell or subject). In another a further embodiment, the laticiferous plant or part thereof is genetically modified by at least one heterologous nucleotide sequence that is capable of reducing the activity of the at least one oxidosqualene cyclase. In a further embodiment, the laticiferous plant, progeny thereof or part thereof is genetically modified by at least one heterologous nucleotide sequence that is capable of reducing the activity of the at least one oxidosqualene cyclase. Preferably, the laticiferous plant or part thereof is genetically modified by at least one heterologous nucleotide sequence that is capable of reducing or eliminating the expression of the gene of the at least one oxidosqualene cyclase. Also preferred, the laticiferous plant, progeny thereof or part thereof is genetically modified by at least one heterologous nucleotide sequence that is capable of reducing or eliminating the expression of the gene of the at least one oxidosqualene cyclase. The term "is capable of reducing or eliminating" is also to be considered compared to the respective wild-type or untreated laticiferous plant, progeny thereof or part thereof as defined above. Examples for such heterologous nucleotide sequences include nucleotides that can induce RNA interference, such as siRNA or shRNA.

Accordingly, in one embodiment of the method of the present invention, the at least one heterologous nucleotide sequence encodes at least one RNAi that interferes with the mRNA encoding the at least one oxidosqualene cyclase, with the proviso that the at least one RNAi is capable of reducing or eliminating the activity of the at least one oxidosqualene cyclase. Activity in this context may relate to a reduced or eliminated amount of triterpenes or triterpenoids in the resulting rubber or latex of the laticiferous plant, progeny thereof or part thereof. In this context "capable of reducing the activity of the at least one oxidosqualene cyclase" means that the respective RNAi can reduce the activity of the at least one oxidosqualene cyclase contained in the laticiferous plant, progeny thereof or part thereof for at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94% or 95%, compared to the wild-type or untreated laticiferous plant, progeny thereof or part thereof, meaning without or in the absence of the respective RNAi. In this context, "capable of eliminating the activity of the at least one oxidosqualene cyclase" means that the respective RNAi can reduce the activity of the at least one oxidosqualene cyclase contained in the laticiferous plant, progeny thereof or part thereof for at least 95.1%, 95.2%, 95.3%, 95.4%, 95.5%, 95.6%, 95.7%, 95.8%, 95.9%, 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, 99.9% or even 100.00%, compared to the wild-type or untreated laticiferous plant, progeny thereof or part thereof, meaning without or in the absence of the respective RNAi.

The amount or content of triterpenes or triterpenoids can be determined by methods known to a person skilled in the art. Such methods e.g. include, but are not limited to, mass spectrometry, chromatography such as RP-HPLC or gas chromatography, or NMR. An exemplary method for the quantification of triterpenes and/or triterpenoids in natural rubber is described in Example 1.

In another embodiment of the method of the present invention, the at least one RNAi is specifically directed against the mRNA transcript of the at least one oxidosqualene cyclase. Preferably, the at least one RNAi comprises or consists of a nucleotide sequence according to SEQ ID NO: 1, and/or comprises or consists of a nucleotide sequence according to SEQ ID NO: 2, and/or comprises or consists of a nucleotide sequence being at least 60%, 70%, 80%, 90%, 95% or 99% identical to SEQ ID NO: 1 or SEQ ID NO: 2.

The nucleotide sequence according to SEQ ID NO: 1 of the present invention is given as follows:

```
TCTCCAAGCGCCCATAGCGGAAAAGTGTTCCTATATTCTGCATAATGTAAC

ATGCAATTCTTCATGTACACTCCTGTTATTTCCTGTTGAGGAAAGTCTCCA

TTATCCATTTGTCCATTTATGAGCAATTTTGCTGCCTTGTGTAATGGTGTC

GGATCTCTTTCAGCCTGTCCACCACATAGAAGACCAAGCATGGCCCATGAA

GTTTGCACAAAATTTGTTCTGTTCCCTTCCAAAGGTATAAATTTCTCTTGT

GGGCATGACTCAAAGTTCTCTCCCCAACCACCTTCTGAGTTTTGTGTCGAG

AGGAAAAACTTGACAGCTTTCCGAACTGCTTCACTATTTTCATATGTTTGT

CCACAAGCTACCAATCCTTGTAACACGAAATAGGTTCCATAAAGATAACAT

ATACCCCAATAACCATACCAAGAACCATTTTCTTGTT.
```

The complementary sequence thereto, which is, for example, also present in a vector construct comprising the SEQ ID NO: 1 if the vector comprises a hairpin-structure, is given as follows:

```
                                             (SEQ ID NO: 47)
AACAAGAAAATGGTTCTTGGTATGGTTATTGGGGTATATGTTATCTTTATG

GAACCTATTTCGTGTTACAAGGATTGGTAGCTTGTGGACAAACATATGAAA

ATAGTGAAGCAGTTCGGAAAGCTGTCAAGTTTTTCCTCTCGACACAAAACT

CAGAAGGTGGTTGGGGAGAGAACTTTGAGTCATGCCCACAAGAGAAATTTA

TACCTTTGGAAGGGAACAGAACAAATTTTGTGCAAACTTCATGGGCCATGC

TTGGTCTTCTATGTGGTGGACAGGCTGAAAGAGATCCGACACCATTACACA

AGGCAGCAAAATTGCTCATAAATGGACAAATGGATAATGGAGACTTTCCTC

AACAGGAAATAACAGGAGTGTACATGAAGAATTGCATGTTACATTATGCAG

AATATAGGAACACTTTTCCGCTATGGGCGCTTGGAGA.
```

The nucleotide sequence according to SEQ ID NO: 2 of the present invention is given as follows:

```
ATCCCAAGCTTGAATCGCACGGTTCAGTCTAACTGCCTTTCTCACGGCTGT

TGTCACCGCTTCATAGTTCACATCTTCGTCGTCTCCAAGTCTCACTGGAGG

TACGCTTATAAGATCAATTCCGC.
```

The complementary sequence thereto, which is, for example, also present in a vector construct comprising the SEQ ID NO: 2 if the vector comprises a hairpin-structure, is given as follows:

```
                                             (SEQ ID NO: 48)
GCGGAATTGATCTTATAAGCGTACCTCCAGTGAGACTTGGAGACGACGAAG

ATGTGAACTATGAAGCGGTGACAACAGCCGTGAGAAAGGCAGTTAGACTGA

ACCGTGCGATTCAAGCTTGGGAT.
```

More preferably, the at least one RNAi comprises or consists of a nucleotide sequence being at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% identical to SEQ ID NO: 1.

Even more preferably, the at least one RNAi consists of a nucleotide sequence being at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% identical to SEQ ID NO: 1.

More preferably, the at least one RNAi comprises or consists of a nucleotide sequence being at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% identical to SEQ ID NO: 2.

Even more preferably, the at least one RNAi consists of a nucleotide sequence being at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% identical to SEQ ID NO: 2.

More preferably, the at least one RNAi comprises or consists of a nucleotide sequence according to SEQ ID NO: 1, even more preferably, the at least one RNAi consists of a nucleotide sequence according to SEQ ID NO: 1. More preferably, the at least one RNAi comprises or consists of a nucleotide sequence according to SEQ ID NO: 2, even more preferably, the at least one RNAi consists of a nucleotide sequence according to SEQ ID NO: 2.

Two amino-acid or nucleotide sequences are said to be "identical" within the context of the present invention, if the sequence of amino-acid or nucleotide residues in the two sequences is the same when aligned for maximum correspondence as described below. Sequence comparisons between two (or more) peptides or polynucleotides are typically performed by comparing sequences of two optimally aligned sequences over a segment or "comparison window" to identify and compare local regions of sequence similarity. Optimal alignment of sequences for comparison may be conducted by the local homology algorithm of Smith and Waterman, *Ad. App. Math* 2: 482 (1981), by the homology alignment algorithm of Neddleman and Wunsch, *J. Mol. Biol.* 48: 443 (1970), by the search for similarity method of Pearson and Lipman, *Proc. Natl. Acad. Sci*. (U.S.A.) 85: 2444 (1988), by computerized implementation of these algorithms (GAP, BESTFIT, FASTA, and TFASTA in the Wisconsin Genetics Software Package, Genetics Computer Group (GCG), 575 Science Dr., Madison, Wis.), or by visual inspection.

"Percentage of sequence identity" (or "degree" or "identity") is determined by comparing two optimally aligned sequences over a comparison window, where the portion of the peptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity.

The definition of sequence identity given above is the definition that would use one of skill in the art. The definition by itself does not need the help of any algorithm, said algorithms being helpful only to achieve the optimal alignments of sequences, rather than the calculation of sequence identity.

From the definition given above, it follows that there is a well-defined and only one value for the sequence identity between two compared sequences, which value corresponds to the value obtained for the best or optimal alignment.

Instead of reducing the amount of the enzyme oxidosqualene cyclase, it is also within the context of the present invention that the reduction or elimination of the activity of the oxidosqualene cyclase may be inhibited by inhibitors. Accordingly, in an embodiment of the method of the present invention, the laticiferous plant or part thereof is genetically modified by subjecting it to and/or incubating it with agents, which are capable of reducing or eliminating the activity of the at least one oxidosqualene cyclase.

Further, in one embodiment of the method of the present invention, the laticiferous plant, progeny thereof or part thereof is genetically modified by subjecting it to and/or incubating it with agents, which are capable of reducing or eliminating the activity of the at least one oxidosqualene cyclase. This means, that the term "genetically modified" or "genetically modification" may also comprise subjecting the laticiferous plant, progeny thereof or part thereof of the present invention or the laticiferous plant, progeny thereof or part thereof used in any embodiments of the method of the present invention to and/or incubating it with agents, which are capable of reducing or eliminating the activity of the at least one oxidosqualene cyclase. The term "is/are capable of reducing or eliminating" is also to be considered compared to the respective wild-type or untreated laticiferous plant, progeny thereof or part thereof as defined above. Preferably, such an agent is an inhibitor of the activity of the at least one oxidosqualene cyclase. More preferably, the inhibitor of the activity of the at least one oxidosqualene cyclase is selected from the group consisting of 2,3-sulfidosqualene, derivatives of oxidosqualene, even more preferably 10- and 19-azasqualene derivatives, 4,4,10β-trimethyl-trans-decal-3-β-ol (TMD) or derivatives thereof, aminoketones, azadecaline and derivatives of imidazoline, epohelmins, lanopylins, isoquinoline derivatives, 4-piperidinopyridines and 4-piperidinopyrimidines, even more preferably BIBB 515 (1-(4-chlorobenzoyl)-4-((4-2-oxazolin-2-yl)benzylidene)) piperidine), vinyl sulfide and ketene dithioacetal derivatives, umbelliferone aminoalkyl derivatives and digalactosylglycerols.

In another embodiment of the method of the present invention, the laticiferous plant or part thereof is genetically modified by at least one heterologous nucleotide sequence that is capable of reducing or eliminating the activity of the at least one oxidosqualene cyclase, preferably that is capable of reducing or eliminating the expression of the gene of the at least one oxidosqualene cyclase, and/or wherein the laticiferous plant or part thereof is genetically modified by subjecting it to and/or incubating it with agents, which are capable of reducing or eliminating the activity of the at least one oxidosqualene cyclase. In another embodiment of the method of the present invention, the laticiferous plant, progeny thereof or part thereof is genetically modified by at least one heterologous nucleotide sequence that is capable of reducing or eliminating the activity of the at least one oxidosqualene cyclase, preferably that is capable of reducing or eliminating the expression of the gene of the at least one oxidosqualene cyclase, and/or wherein the laticiferous plant, progeny thereof or part thereof is genetically modified by subjecting it to and/or incubating it with agents, which are capable of reducing or eliminating the activity of the at least one oxidosqualene cyclase. The above given definitions also apply for this embodiment, e.g. the term "is/are capable of reducing or eliminating" is also to be considered compared to the respective wild-type or untreated laticiferous plant, progeny thereof or part thereof as defined above.

In a further embodiment of the method of the present invention, the laticiferous plant or part thereof is selected from the group of plant families consisting of Apocynaceae, Asteraceae, Euphorbiaceae and Moraceae. In a further embodiment of the method of the present invention, the laticiferous plant, progeny thereof or part thereof is selected from the group of plant families consisting of Apocynaceae, Asteraceae, Euphorbiaceae and Moraceae.

In a further embodiment of the method of the present invention, it is preferred that the laticiferous plant or part thereof is selected from the group consisting of *Agoseris glauca, Apocynum venetum, Chrysothamnus graveolens, Chrysothamnus nauseosus, Chrysothamnus viscidiflorus, Funtumia elastica, Parthenium argentatum, Scorzonera acanthoclada, Scorzonera albicaulis, Scorzonera divaricate, Scorzonera hissaricata, Scorzonera racemosa, Scorzonera tau-saghyz, Scorzonera tragapogonoides, Scorzonera turkestania, Scorzonera virgate, Solidago canadensis scabra, Solidago fistulosa, Solidago leavenworthii, Solidago rigida, Sonchus oleraceus, Taraxacum brevicomiculaturn, Taraxacum hybemum, Taraxacum koksaghyz, Taraxacum megalorrhizon, Taraxacum officinale* and crossings thereof. In a further embodiment of the method of the present invention, it is preferred that the laticiferous plant or part thereof is selected from the group consisting of *Agoseris glauca, Apocynum venetum, Chrysothamnus graveolens, Chrysothamnus nauseosus, Chrysothamnus viscidiflorus, Cichorium intybus L., Funtumia elastica, Parthenium argentatum, Scorzonera acanthoclada, Scorzonera albicaulis, Scorzonera divaricate, Scorzonera hissaricata, Scorzonera racemosa, Scorzonera tau-saghyz, Scorzonera tragapogonoides, Scorzonera turkestania, Scorzonera virgate, Solidago canadensis scabra, Solidago fistulosa, Solidago leavenworthii, Solidago rigida, Sonchus oleraceus, Taraxacum brevicomiculaturn, Taraxacum hybemum, Taraxacum koksaghyz, Taraxacum megalorrhizon, Taraxacum officinale* and crossings thereof. In a more preferred embodiment, the laticiferous plant or part thereof is *Cichorium intybus* L. The term "crossings thereof" means in the context of the present invention plant varieties or lines that have been created by the deliberate interbreeding of closely or distantly related plant species, e.g. to introduce genes from one variety or line into a new genetic background. The laticiferous plant or part thereof can also be the progeny of the respective laticiferous plant. It is even more preferred that the laticiferous plant or part thereof is selected from the group consisting of *Parthenium argentaturn, Chrysothamnus nauseosus, Taraxacum koksaghyz, Taraxacum officinale* and crossings thereof. However, most preferably the laticiferous plant or part thereof is *Taraxacum koksaghyz*. In one embodiment of the method of the present invention, the laticiferous plant or part thereof is not a member of the family Euphorbiaceae. This means the present invention is also directed to a method of reducing or eliminating the content of triterpenes and/or triterpenoids of latex or rubber from a laticiferous plant or part thereof, comprising genetically modifying the laticiferous plant or part thereof, such that the activity of at least one oxidosqualene cyclase is reduced or eliminated, compared to the respective wild-type or untreated laticiferous plant or part thereof, wherein the laticiferous plant or part thereof is not a member of the family Euphorbiaceae. In another related embodiment of the method of the present invention, the laticiferous plant or part thereof is not *Hevea brasiliensis*. This means the present invention is also directed to a method of reducing or eliminating the content of triterpenes and/or triterpenoids of latex or rubber from a laticiferous plant or part thereof, comprising genetically modifying the laticiferous plant or part thereof, such that the activity of at least one oxidosqualene cyclase is reduced or eliminated, compared to the respective wild-type or untreated laticiferous plant or part thereof, wherein the laticiferous plant or part thereof is not *Hevea brasiliensis*. In a further related embodiment of the method of the present invention, the laticiferous plant or part thereof is not from the genus *Landolphia*. This means, the present invention is also directed to a method of reducing or eliminating the content of triterpenes and/or triterpenoids of latex or rubber from a laticiferous plant or part thereof, comprising genetically modifying the laticiferous plant or part thereof, such that the activity of at least one oxidosqualene cyclase is reduced or eliminated, compared to the respective wild-type or untreated laticiferous plant or part thereof, wherein the laticiferous plant or part thereof is not from the genus *Landolphia*.

In another embodiment of the method of the present invention, the at least one oxidosqualene cyclase is selected from the group consisting of oxidosqualene cyclase 1 according to SEQ ID NO: 4, the oxidosqualene cyclase 2 according to SEQ ID NO: 6, the oxidosqualene cyclase 3 according to SEQ ID NO: 8, the oxidosqualene cyclase 4 according to SEQ ID NO: 10, the oxidosqualene cyclase 5 according to SEQ ID NO: 12, the oxidosqualene cyclase 6 according to SEQ ID NO: 14, the oxidosqualene cyclase 7 according to SEQ ID NO: 16, the oxidosqualene cyclase 8 according to SEQ ID NO: 18, the lupeol synthase according to SEQ ID NO: 20 and an amino acid sequence being at least 60%, 70%, 80%, 90%, 95% or 99% identical to SEQ ID NOs: 4, 6, 8, 10, 12, 14, 16, 18 or 20.

In another embodiment of the method of the present invention, the at least one oxidosqualene cyclase is selected from the group consisting of an amino acid sequence being at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% identical to SEQ ID NOs: 4, 6, 8, 10, 12, 14, 16, 18 or 20.

It is further preferred that the at least one oxidosqualene cyclase is selected from the group consisting of the oxidosqualene cyclase 1 according to SEQ ID NO: 4, the oxidosqualene cyclase 2 according to SEQ ID NO: 6, the oxidosqualene cyclase 3 according to SEQ ID NO: 8 and the oxidosqualene cyclase 5 according to SEQ ID NO: 12 and an amino acid sequence being at least 60%, 70%, 80%, 90%, 95% or 99% identical to SEQ ID NOs: 4, 6, 8 or 12.

In another embodiment of the method of the present invention, the at least one oxidosqualene cyclase is selected from the group consisting of an amino acid sequence being at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% identical to SEQ ID NOs: 4, 6, 8 or 12.

It is even more preferred that the at least one oxidosqualene cyclase is the oxidosqualene cyclase 1 according to SEQ ID NO: 4 or an amino acid sequence being at least 60%, 70%, 80%, 90%, 95% or 99% identical thereto.

In another embodiment of the method of the present invention, the at least one oxidosqualene cyclase is selected from the group consisting of an amino acid sequence being at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% identical to SEQ ID NO: 4. It is most preferred that at least one oxidosqualene cyclase is the oxidosqualene cyclase 1 according to SEQ ID NO: 4.

The nucleotide sequence of the oxidosqualene cyclase 1 is further given herein as SEQ ID NO: 3. The nucleotide sequence of the oxidosqualene cyclase 2 is further given herein as SEQ ID NO: 5. The nucleotide sequence of the oxidosqualene cyclase 3 is further given herein as SEQ ID NO: 7. The nucleotide sequence of the oxidosqualene cyclase 4 is further given herein as SEQ ID NO: 9. The nucleotide sequence of the oxidosqualene cyclase 5 is further given herein as SEQ ID NO: 11. The nucleotide sequence of the oxidosqualene cyclase 6 is further given herein as SEQ ID NO: 13. The nucleotide sequence of the oxidosqualene cyclase 7 is further given herein as SEQ ID NO: 15. The nucleotide sequence of the oxidosqualene cyclase 8 is further given herein as SEQ ID NO: 17. The nucleotide sequence of the lupeol synthase is further given herein as SEQ ID NO: 19.

"Oxidosqualene cyclases (OSC)" as used herein are enzymes involved in the cyclization reactions of 2,3-oxidosqualene to form sterols or triterpenes. It can be differentiated between two different types of cyclisation reaction: The chair-boat-chair conformation results in the formation of cycloartenol, a phytosterol intermediate, while the chair-chair-chair conformation results in the formation of triterpenes (Abe, 2007; Thimmappa et al., 2014). The lupeol synthase also belongs to the oxidosqualene cyclases, wherein the lupeol synthase catalyses the cyclisation of 2,3-oxidosqualene to lupeol.

The polypeptides of TkOSC1-8 and TkLUP according to SEQ ID NOs: 4, 6, 8, 10, 12, 14, 16, 18 and 20 of the present invention comprise 758 to 770 amino acids, whereas TkOSC1 compared to TkOSC2 displays the highest (94%) sequence identity among the newly identified sequences. Analysis of the amino acid sequence reveals that conserved domains reported for OSC are present with only slight modifications for TkOSC4, TkOSC5, TkOSC6 and TkOSC8. Those include a domain essential for product determination (M(W/Y)CY(C/S)R-motif), one region involved in substrate binding and polycyclization initiation (DCTAE-motif) and six repeated QW motifs involved in stabilization of carbocationic intermediates and localized near the 5' and 3'-ends of the proteins (see FIG. 3).

In a further embodiment of the method of the present invention, the part of the laticiferous plant is selected from the group consisting of cells, tissues, organs, roots, stems, branches, leaves, exudates, latex and mixtures thereof. In the Russian dandelion *Taraxacum koksaghyz*, the part of the laticiferous plant with the highest concentration of latex is the root. Accordingly, the part of the laticiferous plant preferably is root, if the plant or part thereof is *Taraxacum koksaghyz*. In the context of the present invention, the term "exudate(s)" comprises saps, gums, resins or nectar of the respective plant.

The present invention also provides a laticiferous plant or part thereof being genetically modified such that the activity of the at least one oxidosqualene cyclase is reduced or eliminated, compared to the respective wild-type or untreated laticiferous plant or part thereof. The present invention also provides a laticiferous plant, progeny thereof or part thereof being genetically modified such that the activity of the at least one oxidosqualene cyclase is reduced or eliminated, compared to the respective wild-type or untreated laticiferous plant, progeny thereof or part thereof.

In one embodiment of the laticiferous plant or part thereof according to the present invention, the laticiferous plant or part thereof is genetically modified by at least one heterologous nucleotide sequence that is capable of reducing or eliminating the activity of the at least one oxidosqualene cyclase, preferably that is capable of reducing or eliminating the expression of the gene of the at least one oxidosqualene cyclase. In one embodiment of the laticiferous plant, progeny thereof or part thereof according to the present invention, the laticiferous plant, progeny thereof or part thereof is genetically modified by at least one heterologous nucleotide sequence that is capable of reducing or eliminating the activity of the at least one oxidosqualene cyclase, preferably that is capable of reducing or eliminating the expression of the gene of the at least one oxidosqualene cyclase. The term "is/are capable of reducing or eliminating" is also to be considered compared to the respective wild-type or untreated laticiferous plant, progeny thereof or part thereof as defined above.

The "activity of at least one oxidosqualene cyclase is reduced" or "reducing the activity of the at least one oxidosqualene cyclase" or "being capable of reducing the activity of at least one oxidosqualene cyclase" means in the context of the present invention and as used herein that the activity of the at least one oxidosqualene cyclase contained in a laticiferous plant, progeny thereof or part thereof is reduced for at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94% or 95%, compared to the wild-type or untreated laticiferous plant, progeny thereof or part thereof, meaning without being genetically modified or before being genetically modified.

The "activity of at least one oxidosqualene cyclase is eliminated" or "eliminating of the activity of the at least one oxidosqualene cyclase" or "being capable of eliminating the activity of at least one oxidosqualene cyclase" means in the context of the present invention and as used herein that the activity of at least one oxidosqualene cyclase of the laticiferous plant, progeny thereof or part thereof is reduced for at least 95.1%, 95.2%, 95.3%, 95.4%, 95.5%, 95.6%, 95.7%, 95.8%, 95.9%, 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, 99.9% or even 100.00%, compared to the wild-type or untreated laticiferous plant, progeny thereof or part thereof, meaning without being genetically modified or before being genetically modified.

In another embodiment, the laticiferous plant or part thereof according to the present invention, is genetically modified by subjecting it to and/or incubating it with agents, which are capable of reducing or eliminating the activity of the at least one oxidosqualene cyclase. In another embodiment, the laticiferous plant, progeny thereof or part thereof according to the present invention, is genetically modified by subjecting it to and/or incubating it with agents, which are capable of reducing or eliminating the activity of the at least one oxidosqualene cyclase. The term "is/are capable of reducing or eliminating" is also to be considered compared to the respective wild-type or untreated laticiferous plant, progeny thereof or part thereof as defined above. Such an agent may be an inhibitor of the activity of the at least one oxidosqualene cyclase, preferably an inhibitor of the activity of the at least one oxidosqualene cyclase selected from the group consisting of 2,3-sulfidosqualene, derivatives of oxidosqualene, more preferably 10- and 19-azasqualene derivatives, 4,4,10β-trimethyl-trans-decal-3-β-ol (TMD) or derivatives thereof, aminoketones, azadecaline and derivatives of imidazoline, epohelmins, lanopylins, isoquinoline derivatives, 4-piperidinopyridines and 4-piperidinopyrimidines, even more preferably BIBB 515 (1-(4-chlorobenzoyl)-4-((4-2-oxazolin-2-yl)benzylidene))piperidine), vinyl sulfide and ketene dithioacetal derivatives, umbelliferone aminoalkyl derivatives and digalactosylglycerols. In a further embodiment, such an agent may be an inhibitor of the activity of the at least one oxidosqualene cyclase and preferably an inhibitor of the activity of the at least one oxidosqualene cyclase selected from the group consisting of 2,3-sulfidosqualene, derivatives of oxidosqualene, more preferably 10- and 19-azasqualene derivatives, 4,4,10β-trimethyl-trans-decal-3-β-ol (TMD) or derivatives thereof, aminoketones, ethyl methanesulfonates, azadecaline and derivatives of imidazoline, epohelmins, lanopylins, isoquinoline derivatives, 4-piperidinopyridines and 4-piperidinopyrimidines, even more preferably BIBB 515 (1-(4-chlorobenzoyl)-4-((4-2-oxazolin-2-yl)benzylidene))piperidine), vinyl sulfide and ketene dithioacetal derivatives, umbelliferone aminoalkyl derivatives and digalactosylglycerols. In a preferred embodiment, an inhibitor of the activity of the at least one oxidosqualene cyclase is ethyl methanesulfonates.

In a further embodiment of the laticiferous plant or part thereof according to the present invention, the laticiferous plant or part thereof is genetically modified by at least one heterologous nucleotide sequence that is capable of reducing or eliminating the activity of the at least one oxidosqualene cyclase, preferably that is capable of reducing or eliminating the expression of the gene of the at least one oxidosqualene cyclase, and/or wherein the laticiferous plant or part thereof is genetically modified by subjecting it to and/or incubating it with agents, which are capable of reducing or eliminating the activity of the at least one oxidosqualene cyclase. In a further embodiment of the laticiferous plant, progeny thereof or part thereof according to the present invention, the laticiferous plant, progeny thereof or part thereof is genetically modified by at least one heterologous nucleotide sequence that is capable of reducing or eliminating the activity of the at least one oxidosqualene cyclase, preferably that is capable of reducing or eliminating the expression of the gene of the at least one oxidosqualene cyclase, and/or wherein the laticiferous plant, progeny thereof or part thereof is genetically modified by subjecting it to and/or incubating it with agents, which are capable of reducing or eliminating the activity of the at least one oxidosqualene cyclase. The "activity of at least one oxidosqualene cyclase is reduced" or "reducing the activity of the at least one oxidosqualene cyclase" or "being capable of reducing the activity of at least one oxidosqualene cyclase" means in this context and as used herein that the activity of the at least one oxidosqualene cyclase contained in a laticiferous plant, progeny thereof or part thereof is reduced for at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94% or 95%, compared to the wild-type or untreated laticiferous plant, progeny thereof or part thereof, meaning without being genetically modified or before being genetically modified. The "activity of at least one oxidosqualene cyclase is eliminated" or "eliminating the activity of the at least one oxidosqualene cyclase" or "being capable of eliminating the activity of at least one oxidosqualene cyclase" means in this context that the activity of at least one oxidosqualene cyclase of the laticiferous plant, progeny thereof or part thereof is reduced for at least 95.1%, 95.2%, 95.3%, 95.4%, 95.5%, 95.6%, 95.7%, 95.8%, 95.9%, 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, 99.9% or even 100.00%, compared to the wild-type or untreated laticiferous plant, progeny thereof or part thereof, meaning without being genetically modified or before being genetically modified.

Thus, in one embodiment of the present invention, the laticiferous plant or part thereof may be a transgenic plant. In one embodiment of the present invention, the laticiferous plant, progeny thereof or part thereof may be a transgenic plant. A "transgenic plant" as used herein refers to a plant that contains genetic material not found in a wild-type plant of the same species, variety or cultivar. The genetic material may include a transgene, the product of a mutagenesis event (such as by transposon or T-DNA insertional mutagenesis), including insertion, deletion or substitution, an activation tagging sequence, a mutated sequence, the product of a homologous recombination event or a sequence modified by chimeraplasty. Typically, the foreign genetic material has been introduced into the plant by human manipulation, but any method can be used as one of skill in the art recognizes. A transgenic plant may contain an expression vector or cassette. The expression cassette typically comprises a polypeptide-encoding sequence operably linked (i.e., under regulatory control of) to appropriate inducible or constitutive regulatory sequences that allow for the expression of polypeptide. The expression cassette can be introduced into a plant by transformation or by breeding after transformation of a parent plant. The term "plant" as used herein refers to a whole plant, including seedlings and mature plants, as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

In one embodiment of the laticiferous plant or part thereof according to the present invention, the at least one heterologous nucleotide sequence encodes at least one RNAi that interferes with the mRNA encoding the at least one oxidosqualene cyclase, with the proviso that the at least one RNAi is capable of reducing or eliminating the activity of the at least one oxidosqualene cyclase. In one embodiment of the laticiferous plant, progeny thereof or part thereof according to the present invention, the at least one heterologous nucleotide sequence encodes at least one RNAi that interferes with the mRNA encoding the at least one oxidosqualene cyclase, with the proviso that the at least one RNAi is capable of reducing or eliminating the activity of the at least one oxidosqualene cyclase. In this context, "capable of reducing the activity of the at least one oxidosqualene cyclase" means that the respective RNAi can reduce the activity of the at least one oxidosqualene cyclase contained in the laticiferous plant, progeny thereof or part thereof for at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94% or 95%, compared to the wild-type or untreated laticiferous plant, progeny thereof or part thereof, meaning without or in the absence of the respective RNAi. In this context, "capable of eliminating the activity of the at least one oxidosqualene cyclase" means that the respective RNAi can reduce the activity of the at least one oxidosqualene cyclase contained in the laticiferous plant, progeny thereof or part thereof for at least 95.1%, 95.2%, 95.3%, 95.4%, 95.5%, 95.6%, 95.7%, 95.8%, 95.9%, 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, 99.9% or even 100.00%, compared to the wild-type or untreated laticiferous plant, progeny thereof or part thereof, meaning without or in the absence of the respective RNAi.

In a further embodiment of the laticiferous plant or part thereof according to the present invention, the at least one RNAi is specifically directed against the mRNA transcript of the at least one oxidosqualene cyclase, preferably wherein the at least one RNAi comprises or consists of a nucleotide sequence according to SEQ ID NO: 1 and/or comprises or consists of a nucleotide sequence according to SEQ ID NO: 2 and/or comprises or consists of a nucleotide sequence being at least 60%, 70%, 80%, 90%, 95% or 99% identical to SEQ ID NO: 1 or SEQ ID NO: 2. In a further embodiment of the laticiferous plant, progeny thereof or part thereof according to the present invention, the at least one RNAi is specifically directed against the mRNA transcript of the at least one oxidosqualene cyclase, preferably wherein the at least one RNAi comprises or consists of a nucleotide sequence according to SEQ ID NO: 1 and/or comprises or consists of a nucleotide sequence according to SEQ ID NO: 2 and/or comprises or consists of a nucleotide sequence being at least 60%, 70%, 80%, 90%, 95% or 99% identical to SEQ ID NO: 1 or SEQ ID NO: 2.

Also for all embodiments of the laticiferous plant, progeny thereof or part thereof according to the present invention, the nucleotide sequence according to SEQ ID NO: 1 is given as follows:

```
TCTCCAAGCGCCCATAGCGGAAAAGTGTTCCTATATTCTGCATAATGTAAC

ATGCAATTCTTCATGTACACTCCTGTTATTTCCTGTTGAGGAAAGTCTCCA

TTATCCATTTGTCCATTTATGAGCAATTTTGCTGCCTTGTGTAATGGTGTC

GGATCTCTTTCAGCCTGTCCACCACATAGAAGACCAAGCATGGCCCATGAA

GTTTGCACAAAATTTGTTCTGTTCCCTTCCAAAGGTATAAATTTCTCTTGT

GGGCATGACTCAAAGTTCTCTCCCCAACCACCTTCTGAGTTTTGTGTCGAG

AGGAAAAACTTGACAGCTTTCCGAACTGCTTCACTATTTTCATATGTTTGT

CCACAAGCTACCAATCCTTGTAACACGAAATAGGTTCCATAAAGATAACAT

ATACCCCAATAACCATACCAAGAACCATTTTCTTGTT.
```

The complementary sequence thereto, which is, for example, also present in a vector construct comprising the SEQ ID NO: 1 if the vector comprises a hairpin-structure, is given as follows:

(SEQ ID NO: 47)

AACAAGAAAATGGTTCTTGGTATGGTTATTGGGGTATATGTTATCTTTATG

GAACCTATTTCGTGTTACAAGGATTGGTAGCTTGTGGACAAACATATGAAA

ATAGTGAAGCAGTTCGGAAAGCTGTCAAGTTTTTCCTCTCGACACAAAACT

CAGAAGGTGGTTGGGGAGAGAACTTTGAGTCATGCCCACAAGAGAAATTTA

TACCTTTGGAAGGGAACAGAACAAATTTTGTGCAAACTTCATGGGCCATGC

TTGGTCTTCTATGTGGTGGACAGGCTGAAAGAGATCCGACACCATTACACA

AGGCAGCAAAATTGCTCATAAATGGACAAATGGATAATGGAGACTTTCCTC

AACAGGAAATAACAGGAGTGTACATGAAGAATTGCATGTTACATTATGCAG

AATATAGGAACACTTTTCCGCTATGGGCGCTTGGAGA.

Also for all embodiments of the laticiferous plant, progeny thereof or part thereof according to the present invention, the nucleotide sequence according to SEQ ID NO: 2 of the present invention is given as follows:

ATCCCAAGCTTGAATCGCACGGTTCAGTCTAACTGCCTTTCTCACGGCTGT

TGTCACCGCTTCATAGTTCACATCTTCGTCGTCTCCAAGTCTCACTGGAGG

TACGCTTATAAGATCAATTCCGC.

The complementary sequence thereto, which is, for example, also present in a vector construct comprising the SEQ ID NO: 2 if the vector comprises a hairpin-structure, is given as follows:

(SEQ ID NO: 48)

GCGGAATTGATCTTATAAGCGTACCTCCAGTGAGACTTGGAGACGACGAAG

ATGTGAACTATGAAGCGGTGACAACAGCCGTGAGAAAGGCAGTTAGACTGA

ACCGTGCGATTCAAGCTTGGGAT.

More preferably, the at least one RNAi comprises or consists of a nucleotide sequence being at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% identical to SEQ ID NO: 1.

Even more preferably, the at least one RNAi consists of a nucleotide sequence being at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% identical to SEQ ID NO: 1.

More preferably, the at least one RNAi comprises or consists of a nucleotide sequence being at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% identical to SEQ ID NO: 2.

Even more preferably, the at least one RNAi consists of a nucleotide sequence being at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% identical to SEQ ID NO: 2.

More preferably, the at least one RNAi comprises or consists of a nucleotide sequence according to SEQ ID NO: 1, even more preferably, the at least one RNAi consists of a nucleotide sequence according to SEQ ID NO: 1. More preferably, the at least one RNAi comprises or consists of a nucleotide sequence according to SEQ ID NO: 2, even more preferably, the at least one RNAi consists of a nucleotide sequence according to SEQ ID NO: 2.

In a further embodiment of the laticiferous plant or part thereof according to the present invention, the laticiferous plant or part thereof is selected from the group of plant families consisting of Apocynaceae, Asteraceae, Euphorbiaceae and Moraceae. Preferably, the laticiferous plant or part thereof according to the present invention is selected from the group consisting of *Agoseris glauca, Apocynum venetum, Chrysothamnus graveolens, Chrysothamnus nauseosus, Chrysothamnus viscidiflorus, Funtumia elastica, Parthenium argentatum, Scorzonera acanthoclada, Scorzonera albicaulis, Scorzonera divaricate, Scorzonera hissaricata, Scorzonera racemosa, Scorzonera tau-saghyz, Scorzonera tragapogonoides, Scorzonera turkestania, Scorzonera virgate, Solidago canadensis scabra, Solidago fistulosa, Solidago leavenworthii, Solidago rigida, Sonchus oleraceus, Taraxacum brevicomiculaturn, Taraxacum hybernum, Taraxacum koksaghyz, Taraxacum megalorrhizon, Taraxacum officinale* and crossings thereof. In a further embodiment of the laticiferous plant or part thereof according to the present invention, the laticiferous plant or part thereof is selected from the group of plant families consisting of Apocynaceae, Asteraceae, Euphorbiaceae and Moraceae. Preferably, the laticiferous plant or part thereof according to the present invention is selected from the group consisting of *Agoseris glauca, Apocynum venetum, Chrysothamnus graveolens, Chrysothamnus nauseosus, Chrysothamnus viscidiflorus, Cichorium intybus L., Funtumia elastica, Parthenium argentatum, Scorzonera acanthoclada, Scorzonera albicaulis, Scorzonera divaricate, Scorzonera hissaricata, Scorzonera racemosa, Scorzonera tau-saghyz, Scorzonera tragapogonoides, Scorzonera turkestania, Scorzonera virgate, Solidago canadensis scabra, Solidago fistulosa, Solidago leavenworthii, Solidago rigida, Sonchus oleraceus, Taraxacum brevicomiculaturn, Taraxacum hybemum, Taraxacum koksaghyz, Taraxacum megalorrhizon, Taraxacum officinale* and crossings thereof. In a more preferred embodiment, the laticiferous plant or part thereof is *Cichorium intybus* L. It is even more preferred that the laticiferous plant or part thereof is selected from the group consisting of *Parthenium argentatum, Chrysothamnus nauseosus, Taraxacum koksaghyz, Taraxacum officinale* and crossings thereof. Most preferably, the laticiferous plant or part thereof is *Taraxacum koksaghyz*. In one embodiment of the laticiferous plant or part thereof according to the present invention, the laticiferous plant or part thereof is not a member of the family Euphorbiaceae. This means the present invention also provides a laticiferous plant or part thereof being genetically modified such that the activity of the at least one oxidosqualene cyclase is reduced or eliminated, compared to the respective wild-type or untreated laticiferous plant or part thereof, wherein the laticiferous plant or part thereof is not a member of the family Euphorbiaceae. In another related embodiment of the laticiferous plant or part thereof according to the present invention, the laticiferous plant or part thereof is not *Hevea brasiliensis*. This means, the present invention also provides a laticiferous plant or part thereof being genetically modified such that the activity of the at least one oxidosqualene cyclase is reduced or eliminated, compared to the respective wild-type or untreated laticiferous plant or part thereof, wherein the laticiferous plant or part thereof is not *Hevea brasiliensis*. In a further related embodiment of the laticiferous plant or part thereof according to the present invention, the laticiferous plant or part thereof is not from the genus *Landolphia*. This means the present invention also provides a laticiferous plant or part thereof being genetically modified such that the activity of the at least one oxidosqualene cyclase is reduced or eliminated, compared to the respective wild-type or untreated laticiferous plant or part thereof, wherein the laticiferous plant or part thereof is not from the genus *Landolphia*. The laticiferous plant or part thereof can also be the progeny of the respective laticiferous plant as mentioned in this paragraph.

In another embodiment of the laticiferous plant or part thereof according to the present invention, the at least one oxidosqualene cyclase is selected from the group consisting of oxidosqualene cyclase 1 according to SEQ ID NO: 4, the oxidosqualene cyclase 2 according to SEQ ID NO: 6, the oxidosqualene cyclase 3 according to SEQ ID NO: 8, the oxidosqualene cyclase 4 according to SEQ ID NO: 10, the oxidosqualene cyclase 5 according to SEQ ID NO: 12, the oxidosqualene cyclase 6 according to SEQ ID NO: 14, the oxidosqualene cyclase 7 according to SEQ ID NO: 16, the oxidosqualene cyclase 8 according to SEQ ID NO: 18, the lupeol synthase according to SEQ ID NO: 20 and an amino acid sequence being at least 60%, 70%, 80%, 90%, 95% or 99% identical to SEQ ID NOs: 4, 6, 8, 10, 12, 14, 16, 18 or 20. Preferably, the at least one oxidosqualene cyclase is selected from the group consisting of the oxidosqualene cyclase 1 according to SEQ ID NO: 4, the oxidosqualene cyclase 2 according to SEQ ID NO: 6, the oxidosqualene cyclase 3 according to SEQ ID NO: 8, the oxidosqualene cyclase 5 according to SEQ ID NO: 12 and an amino acid sequence being at least 60%, 70%, 80%, 90%, 95% or 99% identical to SEQ ID NOs: 4, 6, 8 or 12. More preferably, the at least one oxidosqualene cyclase is the oxidosqualene cyclase 1 according to SEQ ID NO: 4 or an amino acid sequence being at least 60%, 70%, 80%, 90%, 95% or 99% identical thereto. Most preferably, the at least one oxidosqualene cyclase is the oxidosqualene cyclase 1 according to SEQ ID NO: 4.

In another embodiment of the laticiferous plant or part thereof according to the present invention, the at least one oxidosqualene cyclase is selected from the group consisting of an amino acid sequence being at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% identical to SEQ ID NOs: 4, 6, 8, 10, 12, 14, 16, 18 or 20.

In another embodiment of the laticiferous plant or part thereof according to the present invention, it is further preferred that the at least one oxidosqualene cyclase is selected from the group consisting of the oxidosqualene cyclase 1 according to SEQ ID NO: 4, the oxidosqualene cyclase 2 according to SEQ ID NO: 6, the oxidosqualene cyclase 3 according to SEQ ID NO: 8 and the oxidosqualene cyclase 5 according to SEQ ID NO: 12 and an amino acid sequence being at least 60%, 70%, 80%, 90%, 95% or 99% identical to SEQ ID NOs: 4, 6, 8 or 12. In a further embodiment of the laticiferous plant, progeny thereof or part thereof according to the present invention, the at least one RNAi is specifically directed against the mRNA transcript of the at least one oxidosqualene cyclase, preferably wherein the at least one RNAi comprises or consists of a nucleotide sequence according to SEQ ID NO: 1 and/or comprises or consists of a nucleotide sequence according to SEQ ID NO: 2 and/or comprises or consists of a nucleotide sequence being at least 60%, 70%, 80%, 90%, 95% or 99% identical to SEQ ID NO: 1 or SEQ ID NO: 2.

In another embodiment of the laticiferous plant or part thereof according to the present invention, the at least one oxidosqualene cyclase is selected from the group consisting of an amino acid sequence being at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% identical to SEQ ID NOs: 4, 6, 8 or 12.

It is even more preferred for the laticiferous plant or part thereof according to the present invention that the at least one oxidosqualene cyclase is the oxidosqualene cyclase 1 according to SEQ ID NO: 4 or an amino acid sequence being at least 60%, 70%, 80%, 90%, 95% or 99% identical thereto.

In another embodiment of the laticiferous plant or part thereof according to the present invention, the at least one oxidosqualene cyclase is selected from the group consisting of an amino acid sequence being at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% identical to SEQ ID NO: 4. It is most preferred that at least one oxidosqualene cyclase is the oxidosqualene cyclase 1 according to SEQ ID NO: 4.

The nucleotide sequence of the oxidosqualene cyclase 1 is further given herein as SEQ ID NO: 3. The nucleotide sequence of the oxidosqualene cyclase 2 is further given herein as SEQ ID NO: 5. The nucleotide sequence of the oxidosqualene cyclase 3 is further given herein as SEQ ID NO: 7. The nucleotide sequence of the oxidosqualene cyclase 4 is further given herein as SEQ ID NO: 9. The nucleotide sequence of the oxidosqualene cyclase 5 is further given herein as SEQ ID NO: 11. The nucleotide sequence of the oxidosqualene cyclase 6 is further given herein as SEQ ID NO: 13. The nucleotide sequence of the oxidosqualene cyclase 7 is further given herein as SEQ ID NO: 15. The nucleotide sequence of the oxidosqualene cyclase 8 is further given herein as SEQ ID NO: 17. The nucleotide sequence of the lupeol synthase is further given herein as SEQ ID NO: 19.

The definitions as well as the preferred embodiments provided herein above with regard to the method of the present invention apply mutatis mutandis also to the embodiments relating to the laticiferous plant, progeny thereof or part thereof of the present invention. Further, the definitions as well as the embodiments and preferred embodiments provided herein above with regard to the laticiferous plant or part thereof apply mutatis mutandis also to the progeny of the respective laticiferous plant or part thereof.

The present invention also provides an RNAi being specifically directed against a mRNA transcript of at least one oxidosqualene cyclase, for use in a method of reducing or eliminating the content of triterpenes and/or triterpenoids of latex or rubber from a laticiferous plant or part thereof. The present invention also provides an RNAi being specifically directed against a mRNA transcript of at least one oxidosqualene cyclase, for use in a method of reducing or eliminating the content of triterpenes and/or triterpenoids of latex or rubber from a laticiferous plant, progeny thereof or part thereof. In this context, the term "reducing the content of triterpenes and/or triterpenoids" or the term "the content of triterpenes and/or triterpenoids is reduced" or the term "being capable of reducing the content of triterpenes and/or triterpenoids" means, as used herein, that the content of triterpenes and/or triterpenoids contained in a laticiferous plant, progeny thereof or part thereof is reduced for at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94% or 95% compared to the wild-type or untreated laticiferous plant, progeny thereof or part thereof, meaning without being genetically modified or before being genetically modified. Further, the term "eliminating the content of triterpenes and/or triterpenoids" or the term "the content of triterpenes and/or triterpenoids is eliminated" or the term "being capable of eliminating the content of triterpenes and/or triterpenoids" means that the content of triterpenes and/or triterpenoids contained in a laticiferous plant, progeny thereof or part thereof is reduced for at least 95.1%, 95.2%, 95.3%, 95.4%, 95.5%, 95.6%, 95.7%, 95.8%, 95.9%, 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, 99.9% or even 100.00% compared to the wild-type or untreated laticiferous plant, progeny thereof or part thereof, meaning without being genetically modified or before being genetically modified.

Preferably, the RNAi according to the present invention comprises or consists of a nucleotide sequence according to SEQ ID NO: 1 and/or comprises or consists of a nucleotide sequence according to SEQ ID NO: 2 and/or comprises or consists of a nucleotide sequence being at least 60%, 70%, 80%, 90%, 95% or 99% identical to SEQ ID NO: 1 or SEQ ID NO: 2, for use in a method of reducing or eliminating the content of triterpenes and/or triterpenoids of latex or rubber from a laticiferous plant or part thereof. The laticiferous plant or part thereof can also be a progeny of the respective laticiferous plant as mentioned herein.

In a further embodiment of the present invention, the RNAi according to the present invention comprises or consists of a nucleotide sequence according to SEQ ID NO: 1 and/or comprises or consists of a nucleotide sequence being at least 60%, 70%, 80%, 90%, 95% or 99% identical to SEQ ID NO: 1. More preferably, the RNAi according to the present invention consists of a nucleotide sequence according to SEQ ID NO: 1 and/or consists of a nucleotide sequence being at least 60%, 70%, 80%, 90%, 95% or 99% identical to SEQ ID NO: 1. Most preferably, the RNAi according to the present invention consists of a nucleotide sequence according to SEQ ID NO: 1.

In a further embodiment of the present invention, the RNAi according to the present invention comprises or consists of a nucleotide sequence according to SEQ ID NO: 2 and/or comprises or consists of a nucleotide sequence being at least 60%, 70%, 80%, 90%, 95% or 99% identical to SEQ ID NO: 2. More preferably, the RNAi according to the present invention consists of a nucleotide sequence according to SEQ ID NO: 2 and/or consists of a nucleotide sequence being at least 60%, 70%, 80%, 90%, 95% or 99% identical to SEQ ID NO: 2. Most preferably, the RNAi according to the present invention consists of a nucleotide sequence according to SEQ ID NO: 2.

Also for all embodiments of the RNAi according to the present invention, the nucleotide sequence according to SEQ ID NO: 1 is given as follows:

```
TCTCCAAGCGCCCATAGCGGAAAAGTGTTCCTATATTCTGCATAATGTAAC

ATGCAATTCTTCATGTACACTCCTGTTATTTCCTGTTGAGGAAAGTCTCCA

TTATCCATTTGTCCATTTATGAGCAATTTTGCTGCCTTGTGTAATGGTGTC

GGATCTCTTTCAGCCTGTCCACCACATAGAAGACCAAGCATGGCCCATGAA

GTTTGCACAAAATTTGTTCTGTTCCCTTCCAAAGGTATAAATTTCTCTTGT

GGGCATGACTCAAAGTTCTCTCCCCAACCACCTTCTGAGTTTTGTGTCGAG

AGGAAAAACTTGACAGCTTTCCGAACTGCTTCACTATTTTCATATGTTTGT

CCACAAGCTACCAATCCTTGTAACACGAAATAGGTTCCATAAAGATAACAT

ATACCCCAATAACCATACCAAGAACCATTTTCTTGTT.
```

The complementary sequence thereto, which is, for example, also present in a vector construct comprising the SEQ ID NO: 1 if the vector comprises a hairpin-structure, is given as follows:

```
                                     (SEQ ID NO: 47)
AACAAGAAAATGGTTCTTGGTATGGTTATTGGGGTATATGTTATCTTTATG

GAACCTATTTCGTGTTACAAGGATTGGTAGCTTGTGGACAAACATATGAAA

ATAGTGAAGCAGTTCGGAAAGCTGTCAAGTTTTTCCTCTCGACACAAAACT

CAGAAGGTGGTTGGGGAGAGAACTTTGAGTCATGCCCACAAGAGAAATTTA

TACCTTTGGAAGGGAACAGAACAAATTTTGTGCAAACTTCATGGGCCATGC

TTGGTCTTCTATGTGGTGGACAGGCTGAAAGAGATCCGACACCATTACACA

AGGCAGCAAAATTGCTCATAAATGGACAAATGGATAATGGAGACTTTCCTC

AACAGGAAATAACAGGAGTGTACATGAAGAATTGCATGTTACATTATGCAG

AATATAGGAACACTTTTCCGCTATGGGCGCTTGGAGA.
```

Also for all embodiments of the RNAi according to the present invention, the nucleotide sequence according to SEQ ID NO: 2 of the present invention is given as follows:

```
ATCCCAAGCTTGAATCGCACGGTTCAGTCTAACTGCCTTTCTCACGGCTGT

TGTCACCGCTTCATAGTTCACATCTTCGTCGTCTCCAAGTCTCACTGGAGG

TACGCTTATAAGATCAATTCCGC.
```

The complementary sequence thereto, which is, for example, also present in a vector construct comprising the SEQ ID NO: 2 if the vector comprises a hairpin-structure, is given as follows:

```
                                        (SEQ ID NO: 48)
GCGGAATTGATCTTATAAGCGTACCTCCAGTGAGACTTGGAGACGACGAAG

ATGTGAACTATGAAGCGGTGACAACAGCCGTGAGAAAGGCAGTTAGACTGA

ACCGTGCGATTCAAGCTTGGGAT.
```

Preferably, the RNAi according to the present invention comprises or consists of a nucleotide sequence being at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% identical to SEQ ID NO: 1.

More preferably, the at least one RNAi consists of a nucleotide sequence being at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% identical to SEQ ID NO: 1.

Preferably, the RNAi according to the present invention comprises or consists of a nucleotide sequence being at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% identical to SEQ ID NO: 2.

More preferably, the RNAi according to the present invention consists of a nucleotide sequence being at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% identical to SEQ ID NO: 2.

More preferably, the RNAi according to the present invention comprises or consists of a nucleotide sequence according to SEQ ID NO: 1. Even more preferably, the RNAi according to the present invention consists of a nucleotide sequence according to SEQ ID NO: 1.

More preferably, the RNAi according to the present invention comprises or consists of a nucleotide sequence according to SEQ ID NO: 2. Even more preferably, the at least one RNAi consists of a nucleotide sequence according to SEQ ID NO: 2.

The term "RNA interference" refers generally and in the context of the present invention as used herein to a process in which a double-stranded RNA molecule changes the expression of a nucleic acid sequence with which the double-stranded or short hairpin RNA molecule shares substantial or total homology.

The term "RNAi" refers generally and in the context of the present invention as used herein to an RNA sequence that elicits RNA interference, and which is transcribed from a vector. The terms "short hairpin RNA" or "shRNA" refer to an RNA structure having a duplex region and a loop region. This term should also be understood to specifically include RNA molecules with stem-loop or panhandle secondary structures. In some embodiments of the present invention, RNAi's are expressed initially as shRNAs.

A better understanding of the present invention and of its advantages will be available from the following examples, offered for illustrative purposes only. The examples are not intended to limit the scope of the present invention in any way.

The invention is further characterized by the following items:

1. Method of reducing or eliminating the content of triterpenes and/or triterpenoids of latex or rubber from a laticiferous plant or part thereof, comprising genetically modifying the laticiferous plant or part thereof, such that the activity of at least one oxidosqualene cyclase is reduced or eliminated, compared to the respective wild-type or untreated laticiferous plant or part thereof.

2. Method according to item 1, wherein the laticiferous plant or part thereof is genetically modified by at least one heterologous nucleotide sequence that is capable of reducing or eliminating the activity of the at least one oxidosqualene cyclase, preferably that is capable of reducing or eliminating the expression of the gene of the at least one oxidosqualene cyclase, and/or wherein the laticiferous plant or part thereof is genetically modified by subjecting it to and/or incubating it with agents, which are capable of reducing or eliminating the activity of the at least one oxidosqualene cyclase.

3. Method according to item 2, wherein the at least one heterologous nucleotide sequence encodes at least one RNAi that interferes with the mRNA encoding the at least one oxidosqualene cyclase, with the proviso that the at least one RNAi is capable of reducing or eliminating the activity of the at least one oxidosqualene cyclase.

4. Method according to item 3, wherein the at least one RNAi is specifically directed against the mRNA transcript of the at least one oxidosqualene cyclase, preferably wherein the at least one RNAi comprises or consists of a nucleotide sequence according to SEQ ID NO: 1 and/or comprises or consists of a nucleotide sequence according to SEQ ID NO: 2 and/or comprises or consists of a nucleotide sequence being at least 60%, 70%, 80%, 90%, 95% or 99% identical to SEQ ID NO: 1 or SEQ ID NO: 2.

5. Method according to any one of the preceding items, wherein the laticiferous plant or part thereof is selected from the group of plant families consisting of Apocynaceae, Asteraceae, Euphorbiaceae and Moraceae.

6. Method according to any one of the preceding items, wherein the laticiferous plant or part thereof is selected from the group consisting of *Agoseris glauca, Apocynum venetum, Chrysothamnus graveolens, Chrysothamnus nauseosus, Chrysothamnus viscidiflorus, Funtumia elastica, Parthenium argentatum, Scorzonera acanthoclada, Scorzonera albicaulis, Scorzonera divaricate, Scorzonera hissaricata, Scorzonera racemosa, Scorzonera tau-saghyz, Scorzonera tragapogonoides, Scorzonera turkestania, Scorzonera virgate, Solidago canadensis scabra, Solidago fistulosa, Solidago leavenworthii, Solidago rigida, Sonchus oleraceus, Taraxacum brevicomiculaturn, Taraxacum hybemum, Taraxacum koksaghyz, Taraxacum megalorrhizon, Taraxacum officinale* and crossings thereof, preferably wherein the laticiferous plant or part thereof is selected from the group consisting of *Parthenium argentatum, Chrysothamnus nauseosus, Taraxacum koksaghyz, Taraxacum officinale* and crossings thereof, more preferably wherein the laticiferous plant or part thereof is *Taraxacum koksaghyz.*

7. Method according to any one of the preceding items, wherein the at least one oxidosqualene cyclase is selected from the group consisting of oxidosqualene cyclase 1 according to SEQ ID NO: 4, the oxidosqualene cyclase 2 according to SEQ ID NO: 6, the oxidosqualene cyclase 3 according to SEQ ID NO: 8, the oxidosqualene cyclase 4 according to SEQ ID NO: 10, the oxidosqualene cyclase 5 according to SEQ ID NO: 12, the oxidosqualene cyclase 6 according to SEQ ID NO: 14, the oxidosqualene cyclase 7 according to SEQ ID NO: 16, the oxidosqualene cyclase 8 according to SEQ ID NO: 18, the lupeol synthase according to SEQ ID NO: 20 and an amino acid sequence being at least 60%, 70%, 80%, 90%, 95% or 99% identical to SEQ ID NOs: 4, 6, 8, 10, 12, 14, 16, 18 or 20, preferably wherein the at least one oxidosqualene cyclase is selected from the group consisting of the oxidosqualene cyclase 1 according to SEQ ID NO: 4, the oxidosqualene cyclase 2 according to SEQ ID NO: 6, the oxidosqualene cyclase 3 according to SEQ ID NO: 8 and the oxidosqualene cyclase 5 according to SEQ ID NO: 12 and an amino acid sequence being at least 60%, 70%, 80%, 90%, 95% or 99% identical to SEQ ID NOs: 4, 6, 8 or 12, more preferably wherein the at least one oxidosqualene cyclase is the oxidosqualene cyclase 1 according to SEQ ID NO: 4 or an amino acid sequence being at least 60%, 70%, 80%, 90%, 95% or 99% identical thereto.

8. Method according to any one of the preceding items, wherein the part of the laticiferous plant is selected from the group consisting of cells, tissues, organs, roots, stems, branches, leaves, exudates, latex and mixtures thereof.

9. Laticiferous plant or part thereof being genetically modified such that the activity of at least one oxidosqualene cyclase is reduced or eliminated, compared to the respective wild-type or untreated laticiferous plant or part thereof.

10. Laticiferous plant or part thereof according to item 9, wherein the laticiferous plant or part thereof is genetically modified by at least one heterologous nucleotide sequence that is capable of reducing or eliminating the activity of the at least one oxidosqualene cyclase, preferably that is capable of reducing or eliminating the expression of the gene of the at least one oxidosqualene cyclase, and/or wherein the laticiferous plant or part thereof is genetically modified by subjecting it to and/or incubating it with agents, which are capable of reducing or eliminating the activity of the at least one oxidosqualene cyclase.

11. Laticiferous plant or part thereof according to item 9 or 10, wherein the at least one heterologous nucleotide sequence encodes at least one RNAi that interferes with the mRNA encoding the at least one oxidosqualene cyclase with the proviso that the at least one RNAi is capable of reducing or eliminating the activity of the at least one oxidosqualene cyclase.

12. Laticiferous plant or part thereof according to item 11, wherein the at least one RNAi is specifically directed against the mRNA transcript of the at least one oxidosqualene cyclase, preferably wherein the at least one RNAi comprises or consists of a nucleotide sequence according to SEQ ID NO: 1 and/or comprises or consists of a nucleotide sequence according to SEQ ID NO: 2 and/or comprises or consists of a nucleotide sequence being at least 60%, 70%, 80%, 90%, 95% or 99% identical to SEQ ID NO: 1 or SEQ ID NO: 2.

13. Laticiferous plant or part thereof according to any one of items 9 to 12, wherein the laticiferous plant or part thereof is selected from the group of plant families consisting of Apocynaceae, Asteraceae, Euphorbiaceae and Moraceae, preferably wherein the laticiferous plant or part thereof is selected from the group consisting of *Agoseris glauca, Apocynum venetum, Chrysothamnus graveolens, Chrysothamnus nauseosus, Chrysothamnus viscidiflorus, Funtumia elastica, Parthenium argentatum, Scorzonera acanthoclada, Scorzonera albicaulis, Scorzonera divaricate, Scorzonera hissaricata, Scorzonera racemosa, Scorzonera tau-saghyz, Scorzonera tragapogonoides, Scorzonera turkestania, Scorzonera virgate, Solidago canadensis scabra, Solidago fistulosa, Solidago leavenworthii, Solidago rigida, Sonchus oleraceus, Taraxacum brevicomiculaturn, Taraxacum hybemum, Taraxacum koksaghyz, Taraxacum megalorrhizon, Taraxacum officinale* and crossings thereof, preferably wherein the laticiferous plant or part thereof is selected from the group consisting of *Parthenium argentatum, Chrysothamnus nauseosus, Taraxacum koksaghyz, Taraxacum officinale* and crossings thereof, more preferably wherein the laticiferous plant or part thereof is *Taraxacum koksaghyz.*

14. Laticiferous plant or part thereof according to any one of items 9 to 13, wherein the at least one oxidosqualene cyclase is selected from the group consisting of oxidosqualene cyclase 1 according to SEQ ID NO: 4, the oxidosqualene cyclase 2 according to SEQ ID NO: 6, the oxidosqualene cyclase 3 according to SEQ ID NO: 8, the oxidosqualene cyclase 4 according to SEQ ID NO: 10, the oxidosqualene cyclase 5 according to SEQ ID NO: 12, the oxidosqualene cyclase 6 according to SEQ ID NO: 14, the oxidosqualene cyclase 7 according to SEQ ID NO: 16, the oxidosqualene cyclase 8 according to SEQ ID NO: 18, the lupeol synthase according to SEQ ID NO: 20, and an amino acid sequence being at least 60%, 70%, 80%, 90%, 95% or 99% identical to SEQ ID NOs: 4, 6, 8, 10, 12, 14, 16, 18 or 20, preferably wherein the at least one oxidosqualene cyclase is selected from the group consisting of the oxidosqualene cyclase 1 according to SEQ ID NO: 4, the oxidosqualene cyclase 2 according to SEQ ID NO: 6, the oxidosqualene cyclase 3 according to SEQ ID NO: 8, the oxidosqualene cyclase 5 according to SEQ ID NO: 12, and an amino acid sequence being at least 60%, 70%, 80%, 90%, 95% or 99% identical to SEQ ID NOs: 4, 6, 8 or 12, more preferably wherein the at least one oxidosqualene cyclase is the oxidosqualene cyclase 1 according to SEQ ID NO: 4 or an amino acid sequence being at least 60%, 70%, 80%, 90%, 95% or 99% identical thereto.

15. RNAi being specifically directed against a mRNA transcript of at least one oxidosqualene cyclase, preferably wherein the RNAi comprises or consists of a nucleotide sequence according to SEQ ID NO: 1 and/or comprises or consists of a nucleotide sequence according to SEQ ID NO: 2 and/or comprises or consists of a nucleotide sequence being at least 60%, 70%, 80%, 90%, 95% or 99% identical to SEQ ID NO: 1 or SEQ ID NO: 2, for use in a method of reducing or eliminating the content of triterpenes and/or triterpenoids of latex or rubber from a laticiferous plant or part thereof.

EXAMPLES

Example 1: Materials and Methods

Plant Material and Cultivation Conditions

*T. koksaghyz* wild-type and transgenic plants were grown in standard soil (ED73 Einheitserde, Fröndenberg, Germany). Every four weeks a commercial fertilizer was supplemented according to the manufacturer's recommendations (Hakaphos Plus, Compo GmbH, Munster, Germany). The plants were cultivated in controlled growth chambers or in the greenhouse at 18° C. and 20 klux (high pressure sodium lamp, HPS 600 Watts, Greenbud, enhanced yellow and red spectrum) with a 16-h photoperiod.

Total RNA Extraction and cDNA Synthesis

Latex was harvested from wounded *T. koksaghyz* root in 90 μl REB buffer (Schmidt et al., 2010). Subsequently, total RNA was extracted using the innuPREP RNA Mini Kit (Analytik Jena, Jena, Germany) according to manufacturer's instructions.

Full-length cDNA was synthesized from 500 ng total RNA using PrimeScript RT Master Mix (TaKaRa, Clontech, Saint-Germain-en-Laye, France) according to manufacturer's instructions.

Quantitative RT-PCR

Quantitative RT-PCR analysis was performed as previously described (Putter et al., 2017). The T. kokzaghyz TkOSC1- and TkOSC-RNAi-plants were 9 to 16 weeks old at the time of expression analysis. All oligonucleotide sequences for expression analysis are listed in Table 1. Primer efficiencies and amplification factors are summarized in Table 2.

TABLE 1

Sequences of oligonucleotides used.

| Oligo | Sequence (5'43') |
|---|---|
| cloning procedures | |
| TkOSC1-RNAi-fwd-Ncol | AAACCATGGGCGGAATTGATCTTATAAGCG (SEQ ID NO: 21) |
| TkOSC1-RNAi-rev-Xhol | AAACTCGAGATCCCAAGCTTGAATCGCAC (SEQ ID NO: 22) |
| TkOSC-RNAi-fwd-Ncol | AAACCATGGAACAAGAAAATGGTTCTTGG (SEQ ID NO: 23) |
| TkOSC-RNAi-rev-Xhol | AAACTCGAGTCTCCAAGCGCCCATAGCGG (SEQ ID NO: 24) |
| qRT-PCR | |
| TkEF1alpha-fw-realtime | CGAGAGATTCGAGAAGGAAGC (SEQ ID NO: 25) |
| TkEF1alpha-rv-realtime | CTGTGCAGTAGTACTTGGTGG (SEQ ID NO: 26) |
| TkLUP-fw-realtime | GCTGACCACCACCAACAACCAC (SEQ ID NO: 27) |
| TkLUP-rv-realtime | AGCACGTTCCTCTTCGGTTCCAG (SEQ ID NO: 28) |
| TkOSC1-fw-realtime | ACTCCTCCCTTGATAATTGCCC (SEQ ID NO: 29) |
| TkOSC1-rv-realtime | TTGTGCTTCTGCCTGATATATAGAAC (SEQ ID NO: 30) |
| TkOSC2-fw-realtime | CCGGTGAGAAGGTGGAAGTT (SEQ ID NO: 31) |
| TkOSC2-rv-realtime | GGAACCGGTACCTCCCAAAC (SEQ ID NO: 32) |
| TkOSC3-fw-realtime | TCCATCCAAACCACAGAAAAG (SEQ ID NO: 33) |
| TkOSC3-rv-realtime | ATGAAGCATACTCCCCAATAAC (SEQ ID NO: 34) |
| TkOSC4-fw-realtime | CCGACAATTCGTAAGGCCACTG (SEQ ID NO: 35) |
| TkOSC4-rv-realtime | TGTTTGCACCACGTTCGACC (SEQ ID NO: 36) |
| TkOSC5-fw-realtime | GAAACACAACTAGAAGATGGCGGT (SEQ ID NO: 37) |
| TkOSC5-rv-realtime | CATAGCCCATGAAGTGTGCACT (SEQ ID NO: 38) |
| TkOSC6-fw-realtime | GGTCATAGCACCATGTTTGGG (SEQ ID NO: 39) |
| TkOSC6-rv-realtime | GGTGACTGAGCCATGATCCAGG (SEQ ID NO: 40) |
| TkOSC7-fw-realtime | CGATGCTGGAACACCCGC (SEQ ID NO: 41) |
| TkOSC7-rv-realtime | GTTGGTGGTATGCTCGATACATC (SEQ ID NO: 42) |
| TkOSC8-fw-realtime | CTGAGCATACCACCTGCGAG (SEQ ID NO: 43) |
| TkOSC8-rv-realtime | CAGCTTTTCTTATTGATGTCGTCACTG (SEQ ID NO: 44) |
| TkRP-fw-realtime | CGTCGATCTCAAGGATGTTGTC (SEQ ID NO: 45) |
| TkRP-rv-realtime | GGAGCTTTGAGAAGAACCAACG (SEQ ID NO: 46) |

TABLE 2

Primer efficiency and amplification factors of qRT-PCR oligos. All values are obtained from cDNA synthesized from *T. koksaghyz* mRNA. The values were calculated using the Bio-Rad CFX Manager v3.1 software (Bio-Rad Laboratories Inc., Hercules, CA, USA) and the qPCR primer efficiency calculator provided by Thermo Fisher Scientific (thermoscientificbio.com/webtools/qpcrefficiency/).

| Oligo pair | Efficiency | Amplification factor (66° C.) |
|---|---|---|
| TkLUP-realtime | 99.17% | 1.99 |
| TkOSC1-realtime | 100.16% | 2.00 |
| TkOSC2-realtime | 101.87% | 2.02 |
| TkOSC3-realtime | 109.67% | 2.10 |
| TkOSC4-realtime | 108.54% | 2.09 |
| TkOSC5-realtime | 106.95% | 2.07 |
| TkOSC6-realtime | 94.39% | 1.94 |
| TkOSC7-realtime | 91.2% | 1.91 |
| TkOSC8-realtime | 98.6% | 1.99 |
| TkEF1alpha-realtime | 104.48% | 2.04 |
| TkRP-realtime | 105.44% | 2.05 |
| TkSQE1-realtime | 95.53% | 1.96 |
| TkSQS1-realtime | 102.56% | 2.03 |

Cloning and Stable Transformation Procedures

For cloning of RNAi-vectors for stable transformation, cDNA fragments were inserted initially, into the Gateway-compatible entry vector pBluescript II KS (+) (Addgene, Cambridge, MA, USA). Therefore, cDNA fragments TkOSC1-RNAi (125 bp) (SEQ ID NO: 48) and TkOSC-RNAi (445 bp) (SEQ ID NO: 47) were amplified by using the oligos TkOSC1-RNAi-fwd-Nco1 (SEQ ID NO: 21) and TkOSC1-RNAi-rev-Xho1 (SEQ ID NO: 22) or TkOSC-RNAi-fwd-Nco1 (SEQ ID NO: 23) and TkOSC-RNAi-rev-Xho1 (SEQ ID NO: 24), respectively. The insertion of the RNAi-fragments by using the Nco1/Xho1 restriction sites of pBluescript II KS (+) resulted in the entry vectors pBluescript-TkOSC1 and pBluescript-TkOSC. Subsequently, the entry vectors were used for recombination into the expression vector pLab12.5-pREF (Epping et al., 2015) resulting in the expression vectors pLab12.5-pREF-TkOSC1-RNAi (SEQ ID NO: 50) and pLab12.5-pREF-TkOSC-RNAi (SEQ ID NO: 49) vectors. The fragment according to SEQ ID NO: 48 (GCGGAATTGATCTTATAAGCGTACCTCCAGTGAGACTTGGAGACGACGAAGATGTGAACT ATGAAGCGGTGACAACAGCCGTGAGAAAGGCAGTTAGACTGAACCGTGCGATTCAAGCTT GGGAT) was used to construct pLab12.5-pREF-TkOSC1-RNAi (SEQ ID NO: 50).

The fragment according to SEQ ID NO: 47 (AACAAGAAAATGGTTCTTGGTATGGTTATTGGG GTATATGTTATCTTTATGGAACCTATTTCGTGTTACAAGGATTGGTAGCTTGTGGACAAACA TATGAAAATAGTGAAGCAGTTCGGAAAGCTGTCAAGTTTTTCCTCTCGACACAAAACTCAGA AGGTGGTTGGGGAGAGAACTTTGAGTCATGCCCACAAGAGAAATTTATACCTTTGGAAGGG AACAGAACAAATTTTGTGCAAACTTCATGGGCCATGCTTGGTCTTCTATGTGGTGGACAGG CTGAAAGAGATCCGACACCATTACACAAGGCAGCAAAATTGCTCATAAATGGACAAATGGA TAATGGAGACTTTCCTCAACAGGAAATAACAGGAGTGTACATGAAGAATTGCATGTTACATT ATGCAGAATATAGGAACACTTTTCCGCTATGGGCGCTTGGAGA) was used to construct pLab12.5-pREF-TkOSC-RNAi (SEQ ID NO: 49).

All vector sequences were verified by sequencing. The complete vector sequence or construct for pLab12.5-pREF-TkOSC1-RNAi is given as SEQ ID NO: 50. The complete vector sequence or construct for pLab12.5-pREF-TkOSC-RNAi is given as SEQ ID NO: 49. Oligonucleotide sequences are shown in Table 1.

The transformation of *T. koksaghyz* by *A. tumefaciens* strain EHA105 with OE- and RNAi-constructs was carried out as previously described (Stolze et al., 2017).

Triterpene Extraction and Analysis

Whole *T. koksaghyz* roots were frozen in liquid nitrogen, freeze-dried, and grinded to a fine powder. Root material was harvested from 5- to 7-month old RNAi-lines. For triterpene analysis, 100 mg of dry root material were used for saponification by adding 20 ml of methanol containing 6% potassium hydroxide and heating to 80° C. for 2 h. 100 μl of betuline (2.5 mg/ml stock solutions in acetone) were added as internal standard. Samples were refilled with water to a volume of 15 ml and extracted three times with one volume of hexane by vortexing and subsequent centrifugation at 4000 rpm for 5 min. The pooled hexane phases were evaporated in the Rocket Evaporator 4D (Genvac Aerospace Inc., Cleveland, USA) and redissolved in 1 ml acetone.

To extract NR from root material, 2 g of the dry root powder as mentioned above and 20 ml of water were transferred into a 50 ml reaction tube and a mixture of steal beads (six 7 g-beads and nine 4 g-beads) were added. The sample was vortexed for 30 min and centrifuged for 15 min at 5000 g. The floating rubber flakes were removed, washed in fresh water and dried over night at 40° C. For triterpene extraction, 100 mg of the resulting NR were filled up with 10 ml acetone and 100 μl internal betuline standard (2.5 mg/ml stock solution in acetone) and were incubated by rotating at room temperature for one week. The resulting extract was dried and redissolved in 1 ml acetone.

Triterpene analysis was performed with a GC-MS-QP 210 Ultra system (Shimadzu, Duisburg, Germany) equipped with a Rxi®-5 ms column (Restek GmbH, Bad Homburg, Germany). 0.5 μl of the extract were injected using split modus (1:10) at an injector and interface temperature of 260° C. The GC temperature program was as follows: 120° C. for 3 min, temperature gradient of 15° C. per minute up to 330° C., 330° C. for 10 min. Electron ionization (EI) in the MS was set to 70 eV. Peak integration and identification was performed with the LabSolution software (Shimadzu, Duisburg, Germany) using a NIST library (NIST=National Institute of Standards and Technology) or by analyzing the corresponding standards obtained from Extrasynthese (Genay, France). Quantification was performed in relation to the internal standard. Retention indices for the triterpene compounds were determined using the LabSolution software in relation to a C8-C40 alkane calibration standard (Sigma Aldrich, Taufkirchen, Germany) using the same operating conditions.

Statistical Analysis

For statistical analysis with more than three samples, the Mann-Whitney U test was applied. This test is a nonparametric test of the null hypothesis that does not require the assumption of normal distributions. The corresponding results were displayed in boxplots. All other statistics were performed using the two-tailed t-test. If variances were assumed to be unequal Welch's correction was applied. The corresponding results were displayed in bar charts.

Example 2: Generation of *T. koksaghyz* Plants Comprising RNAi Targeting OSCs In order to gain *T. koksaghyz* plants with reduced triterpene levels in latex, two different RNAi constructs driven by the laticifer predominant REF-promoter were transformed in

*T. koksaghyz* plants. The fragment (SEQ ID NO: 48) used to construct plab12.5-pREF-TkOSC1-RNAi (SEQ ID NO: 50) (comprising SEQ ID NO: 2 as the RNAi that is specifically directed against the mRNA transcript) comprises a 125 bp long not conserved region and was supposed to knock-down only TkOSC1, whereas the fragment (SEQ ID NO: 47) of pLab12.5-pREF-TkOSC-RNAi (SEQ ID NO: 49) (comprising SEQ ID NO: 1 as the RNAi that is specifically directed against the mRNA transcript) contains a 445 bp long sequence derived from a more conserved region and was expected to knock-down several TkOSCs. After stable transformation, the inventors received two individual TkOSC1-RNAi lines comprising seven plants and five TkOSC-RNAi lines consisting of 12 plants.

Figure 1:
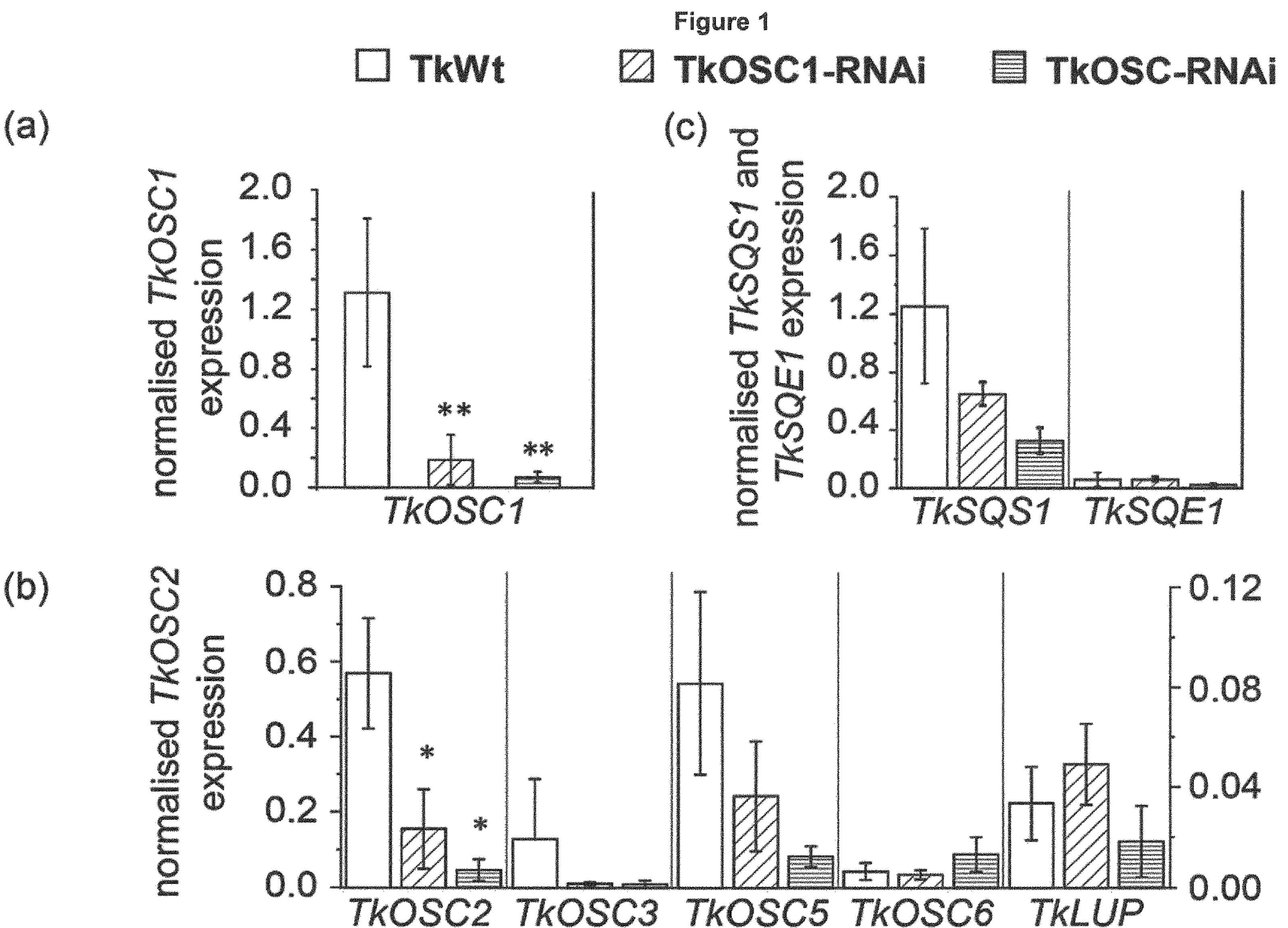
FIG. 1: Analysis of TkOSC1- and TkOSC-RNAi lines.

In 9- to 16-week-old plants, the expression of TkOSC1 in latex was analysed via qPCR (FIG. 1(*a*)). Compared to *T. koksaghyz* wild-type plants (TkWt; n=4) the expression of TkOSC1 was reduced significantly in all lines. For the TkOSC1-RNAi plants, the expression was reduced to one-seventh. For the TkOSC-RNAi plants, the effect was even stronger, resulting in a reduction to one-eighteenth.

To analyse the expression of further triterpene biosynthesis related genes, three wild-type, three TkOSC1-RNAi plants and four TkOSC-RNAi plants were exemplarily used for further qPCR analysis (FIG. 1(*b*) and FIG. 1(*c*)). TkOSC-RNAi plants show a remarkable reduction of TkOSC2, TkOSC3, TkOSC5 and TkLUP expression. Only TkOSC6 expression was slightly enhanced. Surprisingly, the plants with the TkOSC1 specific construct showed also a reduced expression of TkOSC2, TkOSC3 and TkOSC5, but the effect was weaker compared to the TkOSC-RNAi plants. TkOSC6 expression was not affected and TkLUP expression was slightly upregulated. TkOSC4 expression was not detectable in latex of any plants. Earlier studies revealed the co-regulation of TkOSC1 with the upstream genes TkSQS1 and TkSQE1 (Unland et al., 2018). Therefore, the expression of TkSQS1 and TkSQE1 was also analysed in the RNAi-lines (FIG. 3(*c*)). Mean expression of TkSQS1 in TkOSC1-RNAi plants was reduced to one-half, whereas the TkSQE1 expression was comparable to the expression in wild-type plants. In the TkOSC-RNAi lines, TkSQS1 expression was even further reduced to one-quarter and TkSQE1 expression was reduced to one-half compared to the wild-type, confirming the co-regulation of TkSQS1, TkSQE1 and TkOSC1. It can be noted that the expression of several triterpene biosynthesis related genes are affected in both RNAi lines with a general stronger effect in the plants carrying the TkOSC-RNAi fragment.

Example 3: Effect of Oxidosqualene Cyclase (OSC) Knockdown on Triterpene Composition To analyse if alterations in expression have an effect on triterpene composition in the RNAi lines, triterpene extracts of dry root material from 5- to 7-month-old plants were measured by GC/MS (FIG. 1). The pentacyclic triterpenes were strongly affected in the transgenic lines (FIG. 1(*d*) and FIG. 1(*e*)). As a result, the total amount was reduced from 4.6 mg/g in wild-type plants to 2.8 mg/g in TkOSC1-RNAi plants and to 2.6 mg/g in TkOSC-RNAi plants. Especially the most abundant triterpenes, taraxasterol, β-amyrin and one unidentified triterpene (n.i.1), were remarkably reduced with a higher level of significance in TkOSC-RNAi plants.

Besides the pentacyclic triterpenes, further compounds were measured via GC/MS (FIG. 1(*e*), Table 3). It was found that precursors like squalene and 2,3-oxidosqualene accumulated significantly in the transgenic lines, with a higher level of significance in TkOSC-RNAi plants. Additionally, cycloartenol and 24-methylene cycloartanol, two sterol intermediates, were detected in both transgenic lines, with an average of 0.1 mg/g dry root weight in TkOSC1-RNAi plants and 0.9 mg/g dry root weight in TkOSC-RNAi plants. Sterols including campesterol, stigmasterol and sitosterol were detected to equal amounts of about 0.5 mg/g dry root weight in all plants and were not affected by the knock-down. In sum, the total triterpene content including precursors, sterol intermediates, sterols and pentacyclic triterpenes was significantly reduced in transgenic RNAi lines to about two-thirds with a higher level of significance in TkOSC-RNAi plants (FIG. 1(*e*)).

TABLE 3

Triterpene content of root material from *T. koksaghyz* TkOSC1-/TkOSC-RNAi lines. Triterpene compounds were identified and quantified by GC/MS [mg/g root dry weight], corresponding retention indices (RI) were determined in relation to a C8-C40 alkane calibration standard. The mean values represent independent extractions from wild-type plants (n = 4), TkOSC1-RNAi plants (n = 7) and TkOSC-RNAi plants (n = 12) conducted in triplicates and are indicated with the corresponding standard deviations.

| | RI | TkWt | TkOSC1-RNAi | TkOSC-RNAi |
|---|---|---|---|---|
| precursors | | 0.05 ± 0.01 | 0.08 ± 0.04 | 0.17 ± 0.08 |
| squalene | 2843 | 0.01 ± 0.00 | 0.01 ± 0.00 | 0.03 ± 0.02 |
| 2,3-oxidosqualene | 2965 | 0.04 ± 0.01 | 0.06 ± 0.03 | 0.14 ± 0.08 |
| sterol intermediates | | 0.00 ± 0.00 | 0.14 ± 0.06 | 0.27 ± 0.07 |
| cycloartenol | 3478 | 0.00 ± 0.00 | 0.09 ± 0.03 | 0.15 ± 0.04 |
| 24-methylene cycloartanol | 3536 | 0.00 ± 0.00 | 0.05 ± 0.04 | 0.13 ± 0.03 |
| sterols | | 0.50 ± 0.06 | 0.52 ± 0.05 | 0.54 ± 0.05 |
| campesterol | 3313 | 0.07 ± 0.01 | 0.07 ± 0.01 | 0.07 ± 0.01 |
| stigmasterol | 3343 | 0.22 ± 0.04 | 0.21 ± 0.02 | 0.24 ± 0.03 |
| sitosterol | 3405 | 0.21 ± 0.01 | 0.24 ± 0.03 | 0.23 ± 0.02 |
| pentacyclic triterpenes | | 4.57 ± 0.38 | 2.79 ± 0.58 | 2.60 ± 0.42 |
| taraxerol and n.i. | 3448 | 0.70 ± 0.09 | 0.81 ± 0.14 | 0.79 ± 0.10 |
| β-amyrin | 3465 | 0.73 ± 0.06 | 0.25 ± 0.08 | 0.23 ± 0.05 |
| lupeol | 3510 | 0.12 ± 0.02 | 0.18 ± 0.07 | 0.11 ± 0.02 |
| α-amyrin and lup-19(21)-en-3-ol | 3516 | 0.70 ± 0.06 | 0.52 ± 0.14 | 0.56 ± 0.17 |
| TkOSC3-product-1 | 3550 | 0.06 ± 0.01 | 0.05 ± 0.01 | 0.07 ± 0.01 |

TABLE 3-continued

Triterpene content of root material from *T. koksaghyz* TkOSC1-/TkOSC-RNAi lines. Triterpene compounds were identified and quantified by GC/MS [mg/g root dry weight], corresponding retention indices (RI) were determined in relation to a C8-C40 alkane calibration standard. The mean values represent independent extractions from wild-type plants (n = 4), TkOSC1-RNAi plants (n = 7) and TkOSC-RNAi plants (n = 12) conducted in triplicates and are indicated with the corresponding standard deviations.

| | RI | TkWt | TkOSC1-RNAi | TkOSC-RNAi |
|---|---|---|---|---|
| TkOSC3-product-2 | 3590 | 0.48 ± 0.05 | 0.45 ± 0.10 | 0.58 ± 0.12 |
| n.i.1 | 3603 | 0.43 ± 0.04 | 0.19 ± 0.06 | 0.12 ± 0.02 |
| taraxasterol | 3615 | 1.37 ± 0.12 | 0.33 ± 0.13 | 0.14 ± 0.05 |

For triterpene quantification in NR, root material of three wild-type, TkOSC1-RNAi and TkOSC-RNAi plants, respectively, were used for rubber extraction. The triterpenes in NR extracts were isolated by acetone extraction and quantified in relation to NR weight (FIG. 2, Table 4). The crude acetone extracts contained acetate derivatives of different triterpenes. Those acetates as well as the predominant triterpenes in latex (taraxasterol, β-amyrin and n.i.1) were strongly reduced compared to wild-type plants with a higher level of significance in TkOSC-RNAi plants compared to TkOSC1-RNAi plants (FIGS. 2(*a*) and 2(*b*)). The average amount of total pentacyclic triterpenes in wild-type plants with 56.6 mg/g NR was reduced to 33.4 mg/g NR in TkOSC1-RNAi lines or even to 16.1 mg/g NR in TkOSC-RNAi lines (FIG. 2(*c*)).

TABLE 4

Triterpene content in NR extracts from *T. koksaghyz* TkOSC1-/TkOSC-RNAi lines. Triterpene compounds were identified and quantified by GC/MS [mg/g NR dry weight], corresponding retention indices (RI) were determined in relation to a C8-C40 alkane calibration standard. The mean values represent independent extractions from wild-type plants (WtTk; n = 3), TkOSC1-RNAi plants (n = 3) and TkOSC-RNAi plants (n = 3) and are indicated with the corresponding standard deviations.

| | RI | TkWt | TkOSC1-RNAi | TkOSC-RNAi |
|---|---|---|---|---|
| precursors | | 1.02 ± 0.69 | 1.69 ± 0.92 | 5.12 ± 1.14 |
| squalene | 2843 | 0.59 ± 0.53 | 0.54 ± 0.39 | 0.58 ± 0.23 |
| 2,3-oxidosqualene | 2965 | 0.44 ± 0.17 | 1.16 ± 0.53 | 4.55 ± 0.95 |
| sterol precursors | | 0.00 ± 0.00 | 1.86 ± 0.23 | 3.51 ± 0.06 |
| cycloartenol | 3478 | 0.00 ± 0.00 | 1.48 ± 0.46 | 2.06 ± 0.11 |
| 24-methylene cycloartanol | 3536 | 0.00 ± 0.00 | 0.37 ± 0.30 | 1.45 ± 0.06 |
| sterols | | 1.25 ± 0.15 | 2.14 ± 0.63 | 1.45 ± 0.09 |
| campesterol | 3313 | 0.15 ± 0.08 | 0.23 ± 0.07 | 0.16 ± 0.02 |
| stigmasterol | 3343 | 0.43 ± 0.04 | 0.59 ± 0.19 | 0.51 ± 0.05 |
| sitosterol | 3405 | 0.67 ± 0.14 | 1.32 ± 0.38 | 0.78 ± 0.02 |
| pentacyclic triterpenes | | 56.60 ± 0.62 | 33.37 ± 3.99 | 16.05 ± 2.86 |
| taraxerol and n.i. | 3448 | 1.84 ± 0.14 | 3.65 ± 0.85 | 1.93 ± 0.21 |
| β-amyrin | 3465 | 6.14 ± 0.60 | 3.69 ± 0.95 | 1.83 ± 0.32 |
| lupeol | 3510 | 1.85 ± 0.91 | 3.53 ± 0.29 | 1.30 ± 0.24 |
| α-amyrin and lup-19(21)-en-3-ol | 3516 | 4.74 ± 0.34 | 7.89 ± 2.03 | 6.46 ± 1.40 |
| β-amyrin acetate | 3562 | 3.17 ± 0.47 | 0.47 ± 0.27 | 0.00 ± 0.00 |
| TkOSC3-product-1 | 3550 | 0.08 ± 0.01 | 0.28 ± 0.12 | 0.17 ± 0.02 |
| TkOSC3-product-2 | 3590 | 0.62 ± 0.06 | 1.49 ± 0.43 | 1.43 ± 0.24 |
| n.i.1 | 3603 | 8.27 ± 0.07 | 4.54 ± 0.97 | 1.09 ± 0.26 |
| taraxasterol | 3615 | 22.58 ± 1.68 | 7.00 ± 0.77 | 1.85 ± 0.59 |
| triterpene acetate 1 | 3695 | 2.41 ± 0.40 | 0.54 ± 0.20 | 0.00 ± 0.00 |
| triterpene acetate 2 | 3707 | 4.90 ± 1.14 | 0.33 ± 0.24 | 0.00 ± 0.00 |

In contrast to the reduced pentacyclic triterpene content, increasing amounts of triterpene precursors as well as sterol intermediates were again detected in RNAi-lines compared to wild-type, while equal amounts of sterols were measured in all three groups. However, total triterpenoid amount was still significantly decreased to two thirds in TkOSC1-RNAi NR and to less than the half in TkOSC-RNAi NR (FIG. 2(*b*)).

In conclusion, it can be claimed that an OSC knockdown strongly reduces triterpenes/triterpenoids in dandelion root and NR.

The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms “comprising”, “including”, “containing”, etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modifications and variations of the inventions disclosed herein are also considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

REFERENCES

Abe I (2007) Enzymatic synthesis of cyclic triterpenes. Nat Prod Rep 24: 1311-1331

Akashi T, Furuno T, Takahashi T, Ayabe S (1994) TOMOYOSHI AKASHI, TET-UO FURUNO, TAKEYOSHI TAKAHASHI and. 36: 303-308

Augustin J M, Kuzina V, Andersen S B, Bak S (2011) Molecular activities, biosynthesis and evolution of triterpenoid saponins. Phytochemistry 72: 435-457

Clouse S D (2002) *Arabidopsis* mutants reveal multiple roles for sterols in plant development. Plant Cell 14: 1995-2000

Davis W (1997) The rubber industry's biological nightmare. Fortune 136: 86

Epping J, van Deenen N, Niephaus E, Stolze A, Fricke J, Huber C, Eisenreich W, Twyman R M M, Prüfer D, Schulze Gronover C (2015) A rubber transferase activator is necessary for natural rubber biosynthesis in dandelion. Nat Plants 1: 15048

Furuno T, Kamiyama A, Akashi T, Usui M, Takahashi T, Ayabe S (1993) Triterpenoid Constituents of Tissue Cultures and Regenerated Organs of *Taraxacum officinale*. Plant tissue Cult Lett 10: 275-280

Hagel J M, Yeung E C, Facchini P J (2008) Got milk? The secret life of laticifers. Trends Plant Sci 13: 631-639

Hartmann M A (1998) Plant sterols and the membrane environment. Trends Plant Sci 3: 170-175

Krotkov G (1945) Botanical review. XI:

Mooibroek H, Cornish K (2000) Alternative sources of natural rubber. Appl Microbiol Biotechnol 53: 355-365

Moses T, Papadopoulou K K, Osbourn A (2014) Metabolic and functional diversity of saponins, biosynthetic intermediates and semi-synthetic derivatives. Crit Rev Biochem Mol Biol 49: 439-462

Nor H M, Ebdon J R (1998) Telechelic liquid natural rubber: a review. Prog Polym Sci 23: 143-177

Osbourn A, Goss R J, Field R A (2011) The saponins: polar isoprenoids with important and diverse biological activities. Nat Prod Rep 28: 1261-1268

Pütter K M, van Deenen N, Unland K, Prüfer D, Schulze Gronover C (2017) Isoprenoid biosynthesis in dandelion latex is enhanced by the overexpression of three key enzymes involved in the mevalonate pathway. BMC Plant Biol 17: 1-13

Sakdapipanich J T (2007) Structural characterization of natural rubber based on recent evidence from selective enzymatic treatments. J Biosci Bioeng 103: 287-292

Schmidt T, Lenders M, Hillebrand A, van Deenen N, Munt O, Reichelt R, Eisenreich W, Fischer R, Prufer D, Gronover C S (2010) Characterization of rubber particles and rubber chain elongation in *Taraxacum koksaghyz*. BMC Biochem 11: 11

Schulze Gronover C, Wahler D, Prüfer D (2011) Natural Rubber Biosynthesis and Physic-Chemical Studies on Plant Derived Latex. Biotechnol Biopolym 75-88

Stolze A, Wanke A, van Deenen N, Geyer R, Prlifer D, Schulze Gronover C (2017) Development of rubber-enriched dandelion varieties by metabolic engineering of the inulin pathway. Plant Biotechnol J 15: 740-753

Thimmappa R, Geisler K, Louveau T, O'Maille P, Osbourn A (2014) Triterpene Biosynthesis in Plants. Annu Rev Plant Biol 65: 225-257

Unland K, Pütter K M, Vorwerk K, van Deenen N, Prüfer D, Schulze Gronover C (2018) Functional characterization of squalene synthase and squalene epoxidase in *Taraxacum*. 1-15

Xu R, Fazio G C, Matsuda S P T (2004) On the origins of triterpenoid skeletal diversity. Phytochemistry 65: 261-291

The invention claimed is:

1. A method of reducing the content of triterpenes, triterpenoids, or both triterpenes and triterpenoids, of latex or rubber from a laticiferous plant or part thereof, comprising genetically modifying the laticiferous plant or part thereof, such that the activity of at least one oxidosqualene cyclase is reduced, compared to a like laticiferous plant or part thereof that has not been genetically modified by at least one heterologous nucleotide sequence that is capable of reducing the activity of the at least one oxidosqualene cyclase, wherein the laticiferous plant or part thereof is genetically modified by at least one heterologous nucleotide sequence that is capable of reducing the activity of the at least one oxidosqualene cyclase, wherein the at least one heterologous nucleotide sequence encodes at least one RNAi that interferes with the mRNA encoding the at least one oxidosqualene cyclase, with the proviso that the at least one RNAi is capable of reducing the activity of the at least one oxidosqualene cyclase, wherein the at least one RNAi is specifically directed against the mRNA transcript of the at least one oxidosqualene cyclase and thereby affects the presence of the protein of the at least one oxidosqualene cyclase, wherein the at least one oxidosqualene cyclase is selected from the group consisting of an amino acid sequence being at least 99% identical to any one of SEQ ID NOs: 4, 6, 8, 10, 12, 14, 16, 18, or 20, and wherein the at least one RNAi comprises or consists of a nucleotide sequence being at least 99% identical to SEQ ID NO: 1 or SEQ ID NO: 2, wherein the at least one RNAi attaches individually or binds to the mRNA transcript of the at least one oxidosqualene cyclase, wherein the at least one RNAi comprising or consisting of a nucleotide sequence being at least 99% identical to SEQ ID NO: 1 is specifically directed against the mRNA transcript of the at least one oxidosqualene cyclase selected from the group consisting of an amino acid sequence being at least 99% identical to any one of SEQ ID NOs: 4, 6, 8, 10, 12, 14, 16, 18, or 20, and wherein the at least one RNAi comprising or consisting of a nucleotide sequence being at least 99% identical to SEQ ID NO: 2 is specifically directed against the mRNA transcript of the oxidosqualene cyclase of an amino acid sequence being at least 99% identical to SEQ ID NO: 4.

2. The method according to claim 1, wherein the laticiferous plant or part thereof is selected from the group of plant families consisting of Apocynaceae, Asteraceae, Euphorbiaceae and Moraceae.

3. The method according to claim 1, wherein the laticiferous plant or part thereof is selected from the group consisting of *Agoseris glauca, Apocynum venetum, Chrysothamnus graveolens, Chrysothamnus nauseosus, Chrysothamnus viscidiflorus, Funtumia elastica, Parthenium argentatum, Scorzonera acanthoclada, Scorzonera albicaulis, Scorzonera divaricate, Scorzonera hissaricata, Scorzonera racemosa, Scorzonera tau-saghyz, Scorzonera tragapogonoides, Scorzonera turkestania, Scorzonera virgate, Solidago canadensis scabra, Solidago fistulosa, Solidago leavenworthii, Solidago rigida, Sonchus oleraceus, Taraxacum brevicorniculatum, Taraxacum hybernum, Taraxacum koksaghyz, Taraxacum megalorrhizon, Taraxacum officinale* and crossings thereof.

4. The method according to claim 1, wherein the at least one oxidosqualene cyclase is selected from the group consisting of oxidosqualene cyclase 1 according to SEQ ID NO: 4, the oxidosqualene cyclase 2 according to SEQ ID NO: 6, the oxidosqualene cyclase 3 according to SEQ ID NO: 8, the oxidosqualene cyclase 4 according to SEQ ID NO: 10, the oxidosqualene cyclase 5 according to SEQ ID NO: 12, the oxidosqualene cyclase 6 according to SEQ ID NO: 14, the oxidosqualene cyclase 7 according to SEQ ID NO: 16, the oxidosqualene cyclase 8 according to SEQ ID NO: 18, and the lupeol synthase according to SEQ ID NO: 20.

5. The method according to claim 1, wherein the part of the laticiferous plant is selected from the group consisting of cells, tissues, organs, roots, stems, branches, leaves, exudates, latex and mixtures thereof.

6. The method according to claim 1, wherein the at least one RNAi comprises or consists of the nucleotide sequence according to SEQ ID NO: 1, or comprises or consists of the nucleotide sequence according to SEQ ID NO: 2.

7. The method according to claim 3, wherein the laticiferous plant or part thereof is selected from the group consisting of *Parthenium argentatum, Chrysothamnus nauseosus, Taraxacum koksaghyz, Taraxacum officinale* and crossings thereof.

8. The method according to claim 4, wherein the at least one oxidosqualene cyclase is selected from the group consisting of the oxidosqualene cyclase 1 according to SEQ ID NO: 4, the oxidosqualene cyclase 2 according to SEQ ID NO: 6, the oxidosqualene cyclase 3 according to SEQ ID NO: 8, and the oxidosqualene cyclase 5 according to SEQ ID NO: 12, and an amino acid sequence being at least 99% identical to any one of SEQ ID NOs: 4, 6, 8 or 12.

9. The method according to claim 1, wherein the at least one RNAi comprising or consisting of a nucleotide sequence being identical to SEQ ID NO: 1 is specifically directed against the mRNA transcript of at least one oxidosqualene cyclase selected from the group consisting of an amino acid sequence being identical to any one of SEQ ID NOs: 4, 6, 8, 10, 12, 14, 16, 18, or 20, and wherein the at least one RNAi comprising or consisting of a nucleotide sequence being identical to SEQ ID NO: 2 is specifically directed against the mRNA transcript of the oxidosqualene cyclase of an amino acid sequence being identical to SEQ ID NO: 4.

10. The method according to claim 1, wherein the at least one RNAi comprising or consisting of a nucleotide sequence being identical to SEQ ID NO: 1 is specifically directed against the mRNA transcript of the at least one oxidosqualene cyclase selected from the group consisting of an amino acid sequence being identical to any one of SEQ ID NOs: 4, 6, 8, 10, 12, 14, or 20.

11. The method according to claim 1, wherein the at least one RNAi comprising or consisting of a nucleotide sequence being identical to SEQ ID NO: 2 is specifically directed against the mRNA transcript of the oxidosqualene cyclase of an amino acid sequence being identical to SEQ ID NO: 4.

12. The method according to claim 1, wherein taraxasterol and/or β-amyrin, is/are reduced in the lactiferous plant or part thereof.

13. The method according to claim 1, wherein the plant is (a) *Taraxacum koksaghyz*, (b) wherein the part of the plant is the plant root, or both (a) and (b).

14. A method of increasing the content of a triterpene precursor, a triterpenoid precursor, or both triterpene and triterpenoid precursors, of latex or rubber from a laticiferous plant or part thereof, comprising genetically modifying the laticiferous plant or part thereof, such that the activity of at least one oxidosqualene cyclase is reduced, compared to a like laticiferous plant or part thereof that has not been genetically modified by at least one heterologous nucleotide sequence that is capable of reducing the activity of the at least one oxidosqualene cyclase, wherein the laticiferous plant or part thereof is genetically modified by at least one heterologous nucleotide sequence that is capable of reducing the activity of the at least one oxidosqualene cyclase, wherein the at least one heterologous nucleotide sequence encodes at least one RNAi that interferes with the mRNA encoding the at least one oxidosqualene cyclase, with the proviso that the at least one RNAi is capable of reducing the activity of the at least one oxidosqualene cyclase, wherein the at least one RNAi is specifically directed against the mRNA transcript of the at least one oxidosqualene cyclase and thereby affects the presence of the protein of the at least one oxidosqualene cyclase, wherein the at least one oxidosqualene cyclase is selected from the group consisting of an amino acid sequence being at least 99% identical to any one of SEQ ID NOs: 4, 6, 8, 10, 12, 14, 16, 18, or 20, and wherein the at least one RNAi comprises or consists of the nucleotide sequence being at least 99% identical to SEQ ID NO: 1 or SEQ ID NO: 2, wherein the at least one RNAi attaches individually or binds to the mRNA transcript of the at least one oxidosqualene cyclase, wherein the at least one RNAi comprising or consisting of a nucleotide sequence being at least 99% identical to SEQ ID NO: 1 is specifically directed against the mRNA transcript of the at least one oxidosqualene cyclase selected from the group consisting of an amino acid sequence being at least 99% identical to any one of SEQ ID NOs: 4, 6, 8, 10, 12, 14, 16, 18, or 20, and wherein the at least one RNAi comprising or consisting of a nucleotide sequence being at least 99% identical to SEQ ID NO: 2 is specifically directed against the mRNA transcript of the oxidosqualene cyclase of an amino acid sequence being at least 99% identical to SEQ ID NO: 4.

15. The method according to claim 14, wherein one or more of 2,3-oxidosqualene, cycloartenol, 24-methylene cycloartenol is increased in the lactiferous plant or part thereof.

* * * * *

SEQUENCE LISTING

```
<160> NUMBER OF SEQ ID NOS: 50

<210> SEQ ID NO 1
<211> LENGTH: 445
<212> TYPE: DNA
<213> ORGANISM: Artificial
<220> FEATURE:
<223> OTHER INFORMATION: TkOSC RNAi antisense sequence

<400> SEQUENCE: 1

tctccaagcg cccatagcgg aaaagtgttc ctatattctg cataatgtaa catgcaattc      60

ttcatgtaca ctcctgttat ttcctgttga ggaaagtctc cattatccat ttgtccattt     120

atgagcaatt ttgctgcctt gtgtaatggt gtcggatctc tttcagcctg tccaccacat     180

agaagaccaa gcatggccca tgaagtttgc acaaaatttg ttctgttccc ttccaaaggt     240

ataaatttct cttgtgggca tgactcaaag ttctctcccc aaccaccttc tgagttttgt     300
```

```
gtcgagagga aaaacttgac agctttccga actgcttcac tattttcata tgtttgtcca    360

caagctacca atccttgtaa cacgaaatag gttccataaa gataacatat accccaataa    420

ccataccaag aaccattttc ttgtt                                          445
```

<210> SEQ ID NO 2
<211> LENGTH: 125
<212> TYPE: DNA
<213> ORGANISM: Artificial
<220> FEATURE:
<223> OTHER INFORMATION: TkOSC1 RNAi antisense sequence

<400> SEQUENCE: 2

```
atcccaagct tgaatcgcac ggttcagtct aactgccttt ctcacggctg ttgtcaccgc     60

ttcatagttc acatcttcgt cgtctccaag tctcactgga ggtacgctta taagatcaat    120

tccgc                                                                125
```

<210> SEQ ID NO 3
<211> LENGTH: 2313
<212> TYPE: DNA
<213> ORGANISM: Taraxacum koksaghyz

<400> SEQUENCE: 3

```
atgtggaagc tgagaatagg tgaaaagaat ggaaagttca acattggtga tggaaacggt     60

gatgactatt tgcatagcac caacaacttt gtggggagac aaacatggga attcgaccct    120

gatgcaggca cgcagaaaga gcgtgacgaa attgaaaggc ttcgagagca atttttgatc    180

aataaaaaga agcttgacat tagatgttgc gcagacttgc taatgcgaaa tcagcttatt    240

aaggaaagcg gaattgatct tataagcgta cctccagtga gacttggaga cgacgaagat    300

gtgaactatg aagcggtgac aacagccgtg agaaaggcag ttagactgaa ccgtgcgatt    360

caagcttggg atggccattg gccagctgaa aatgccggtc cgctcttctt cactcctccc    420

ttgataattg ccctgtacat aagtggtaca ttggatacca tcctcacaca agaacacaaa    480

agggagatga ttcgttatat gtacatccat caaaatgaag acggagggtg ggggttctat    540

atatcaggca gaagcacaat gatagggact gcgctgaatt atgtgggtct aagacttctt    600

ggagaagatg ataatgatgc aattgctaaa ggccgtaaat ggatacttga ccacggtggc    660

gccacctcta ttccttcgtg gggaaaggtg tatctttcgg tgcttggagt gtacgaatgg    720

gcagggtgta accctcttcc tccagaattc tggctttttc cttccttttt gccttatcat    780

ccagcaaaaa tgtggtgtta ttgcagaacc acatacatgc caatgtcata cttgtatggt    840

acaggcttcc aagggcctat tacggacctt gttaagtctt tgagaaaaga gattcatgtc    900

attccttacc atcagattga ttggaacaaa caacgacata attgttgcaa ggaggatctt    960

tactaccctc atacctacat ccaagatctc ttatgggatg gtcttcatta ttttagtgag   1020

ccacttgtat caaaatggcc tctcaagaag ttaagagaga agggtttgaa aagagtattg   1080

gatctaatgc aatataacgc cgaggaagga cgttacataa ctctgggttg cgttgagaag   1140

tctttacaaa tgatgtgttt ttctgcccta gatccaaatg gaattgactt taaacgacac   1200

cttgctagag tccccgatta cttatgggtg gcggaggatg gtatgaaaat gcaaagtttt   1260

ggtagtcagt tatgggattg tactcttgta actcaagcaa ttatcgctag tgatatggtt   1320

gaagaatatg gagattcact taaaaaagct aacttttact taaaagaatc acagatcaaa   1380

caaaacccaa aaggcgattt cgaaaacatg tgtcgccagt ttacaaaagg ggcttggact   1440
```

```
ttctctgatc aagatcaagg ttgggtcgtc tcagattgca ctgccgaagc tgtgaagtgt   1500

ttattggcat tgtcacaaat gccacaagaa atttccggtg aaaaggtcga cgtcgagcga   1560

ttatatgatg ccattaacgt ccttctttac ctacagagtc cagaaactgg tggttttgca   1620

atttgggagg caccggttcc aaaaccatat ttagagaaat tgaatccttc agaacttttt   1680

gcagacatag tggtcgagag agagcatgtt gaatgtacgg ggtccataat tcaaacgttg   1740

caaacattta aaactctgca tccagggcat cgtcaaaaag aaatagaagt tgctattgaa   1800

aaaggcatac gctttttgga aaatagacaa caagaaaatg gttcttggta tggttattgg   1860

ggtatatgtt atctttatgg aacctatttc gtgttacaag gattggtagc ttgtggacaa   1920

acatatgaaa atagtgaagc agttcggaaa gctgtcaagt tttcctctc gacacaaaac    1980

tcagaaggtg gttggggaga gaactttgag tcatgcccac aagagaaatt tatacctttg   2040

gaagggaaca gaacaaattt tgtgcaaact tcatgggcca tgcttggtct tctatgtggt   2100

ggacaggctg aaagagatcc gacaccatta cacaaggcag caaaattgct cataaatgga   2160

caaatggata atggagactt tcctcaacag gaaataacag gagtgtacat gaagaattgc   2220

atgttacatt atgcagaata taggaacact tttccgctat gggcgcttgg agagtaccgt   2280

aagcgtgttt ggttagcaaa acaagaaacc taa                                2313
```

<210> SEQ ID NO 4
<211> LENGTH: 770
<212> TYPE: PRT
<213> ORGANISM: Taraxacum koksaghyz

<400> SEQUENCE: 4

```
Met Trp Lys Leu Arg Ile Gly Glu Lys Asn Gly Lys Phe Asn Ile Gly
1               5                   10                  15

Asp Gly Asn Gly Asp Asp Tyr Leu His Ser Thr Asn Asn Phe Val Gly
            20                  25                  30

Arg Gln Thr Trp Glu Phe Asp Pro Asp Ala Gly Thr Gln Lys Glu Arg
        35                  40                  45

Asp Glu Ile Glu Arg Leu Arg Glu Gln Phe Leu Ile Asn Lys Lys Lys
    50                  55                  60

Leu Asp Ile Arg Cys Cys Ala Asp Leu Leu Met Arg Asn Gln Leu Ile
65                  70                  75                  80

Lys Glu Ser Gly Ile Asp Leu Ile Ser Val Pro Pro Val Arg Leu Gly
                85                  90                  95

Asp Asp Glu Asp Val Asn Tyr Glu Ala Val Thr Thr Ala Val Arg Lys
            100                 105                 110

Ala Val Arg Leu Asn Arg Ala Ile Gln Ala Trp Asp Gly His Trp Pro
        115                 120                 125

Ala Glu Asn Ala Gly Pro Leu Phe Phe Thr Pro Pro Leu Ile Ile Ala
    130                 135                 140

Leu Tyr Ile Ser Gly Thr Leu Asp Thr Ile Leu Thr Gln Glu His Lys
145                 150                 155                 160

Arg Glu Met Ile Arg Tyr Met Tyr Ile His Gln Asn Glu Asp Gly Gly
                165                 170                 175

Trp Gly Phe Tyr Ile Ser Gly Arg Ser Thr Met Ile Gly Thr Ala Leu
            180                 185                 190

Asn Tyr Val Gly Leu Arg Leu Leu Gly Glu Asp Asp Asn Asp Ala Ile
        195                 200                 205

Ala Lys Gly Arg Lys Trp Ile Leu Asp His Gly Gly Ala Thr Ser Ile
    210                 215                 220
```

```
Pro Ser Trp Gly Lys Val Tyr Leu Ser Val Leu Gly Val Tyr Glu Trp
225                 230                 235                 240

Ala Gly Cys Asn Pro Leu Pro Pro Glu Phe Trp Leu Phe Pro Ser Phe
                245                 250                 255

Leu Pro Tyr His Pro Ala Lys Met Trp Cys Tyr Cys Arg Thr Thr Tyr
            260                 265                 270

Met Pro Met Ser Tyr Leu Tyr Gly Thr Gly Phe Gln Gly Pro Ile Thr
        275                 280                 285

Asp Leu Val Lys Ser Leu Arg Lys Glu Ile His Val Ile Pro Tyr His
    290                 295                 300

Gln Ile Asp Trp Asn Lys Gln Arg His Asn Cys Cys Lys Glu Asp Leu
305                 310                 315                 320

Tyr Tyr Pro His Thr Tyr Ile Gln Asp Leu Leu Trp Asp Gly Leu His
                325                 330                 335

Tyr Phe Ser Glu Pro Leu Val Ser Lys Trp Pro Leu Lys Lys Leu Arg
            340                 345                 350

Glu Lys Gly Leu Lys Arg Val Leu Asp Leu Met Gln Tyr Asn Ala Glu
        355                 360                 365

Glu Gly Arg Tyr Ile Thr Leu Gly Cys Val Glu Lys Ser Leu Gln Met
    370                 375                 380

Met Cys Phe Ser Ala Leu Asp Pro Asn Gly Ile Asp Phe Lys Arg His
385                 390                 395                 400

Leu Ala Arg Val Pro Asp Tyr Leu Trp Val Ala Glu Asp Gly Met Lys
                405                 410                 415

Met Gln Ser Phe Gly Ser Gln Leu Trp Asp Cys Thr Leu Val Thr Gln
            420                 425                 430

Ala Ile Ile Ala Ser Asp Met Val Glu Glu Tyr Gly Asp Ser Leu Lys
        435                 440                 445

Lys Ala Asn Phe Tyr Leu Lys Glu Ser Gln Ile Lys Gln Asn Pro Lys
    450                 455                 460

Gly Asp Phe Glu Asn Met Cys Arg Gln Phe Thr Lys Gly Ala Trp Thr
465                 470                 475                 480

Phe Ser Asp Gln Asp Gln Gly Trp Val Val Ser Asp Cys Thr Ala Glu
                485                 490                 495

Ala Val Lys Cys Leu Leu Ala Leu Ser Gln Met Pro Gln Glu Ile Ser
            500                 505                 510

Gly Glu Lys Val Asp Val Glu Arg Leu Tyr Asp Ala Ile Asn Val Leu
        515                 520                 525

Leu Tyr Leu Gln Ser Pro Glu Thr Gly Gly Phe Ala Ile Trp Glu Ala
    530                 535                 540

Pro Val Pro Lys Pro Tyr Leu Glu Lys Leu Asn Pro Ser Glu Leu Phe
545                 550                 555                 560

Ala Asp Ile Val Val Glu Arg Glu His Val Glu Cys Thr Gly Ser Ile
                565                 570                 575

Ile Gln Thr Leu Gln Thr Phe Lys Thr Leu His Pro Gly His Arg Gln
            580                 585                 590

Lys Glu Ile Glu Val Ala Ile Glu Lys Gly Ile Arg Phe Leu Glu Asn
        595                 600                 605

Arg Gln Gln Glu Asn Gly Ser Trp Tyr Gly Tyr Trp Gly Ile Cys Tyr
    610                 615                 620

Leu Tyr Gly Thr Tyr Phe Val Leu Gln Gly Leu Val Ala Cys Gly Gln
625                 630                 635                 640
```

```
Thr Tyr Glu Asn Ser Glu Ala Val Arg Lys Ala Val Lys Phe Phe Leu
                645                 650                 655

Ser Thr Gln Asn Ser Glu Gly Gly Trp Gly Glu Asn Phe Glu Ser Cys
            660                 665                 670

Pro Gln Glu Lys Phe Ile Pro Leu Glu Gly Asn Arg Thr Asn Phe Val
        675                 680                 685

Gln Thr Ser Trp Ala Met Leu Gly Leu Leu Cys Gly Gly Gln Ala Glu
    690                 695                 700

Arg Asp Pro Thr Pro Leu His Lys Ala Ala Lys Leu Leu Ile Asn Gly
705                 710                 715                 720

Gln Met Asp Asn Gly Asp Phe Pro Gln Gln Glu Ile Thr Gly Val Tyr
                725                 730                 735

Met Lys Asn Cys Met Leu His Tyr Ala Glu Tyr Arg Asn Thr Phe Pro
            740                 745                 750

Leu Trp Ala Leu Gly Glu Tyr Arg Lys Arg Val Trp Leu Ala Lys Gln
        755                 760                 765

Glu Thr
    770


<210> SEQ ID NO 5
<211> LENGTH: 2313
<212> TYPE: DNA
<213> ORGANISM: Taraxacum koksaghyz

<400> SEQUENCE: 5

atgtggaagc tgagaatagg tgaaaagaat ggaaagttca acattggtga tggaaacggc      60

gatgaatatt tgtatagcac caacaacttt gtggggagac aaacatggga gttcgaccct     120

gatgcaggca cacaggaaga gcgtgatgaa gttgaaaggc ttcgagaaca atttctaatc     180

aataagaaga agcttgacat cagttgttgt gcagacttgc tcatgcgaaa tcagcttatt     240

aaggaaagcg gaattgatct tataagcgaa gctccagtga aacttggaca cgatgaggat     300

gtgaactata aagcggtaac aacagcagta agaaaggcag tcagactgaa ccgtgcaatc     360

caagcttggg atggtcattg gccggctgaa aatgcgggtc cgctcttttt cactcctcct     420

ttgataatcg tcttgtatat tagtggtaca ttggataatg tccttacaca agaccacaag     480

aaggagatga ttcgttatat gtacatccat caaaatgaag atggagggtg ggattctat      540

atatcaggca gaagcacaat gatagggact gcgctgaatt atgtgggtct aagacttctt     600

ggagaagatg ataatgatgc aattgctaaa ggccgtaaat ggatacttga ccacggtggc     660

gccacctcta ttccttcgtg ggaaaaggtg tatctttcgg tacttggagt gtacgaatgg     720

gcaggctgta accctcttcc tccagaattc tggctttttc cttccttttt cccttatcat     780

ccagcaaaaa tgtggtgtta ttgcagaacc acatacatgc caatgtcata cttgtatggt     840

agaggcatcc aagggcctat tacggacctc gttaagtctt tgagaaaaga gatccatgtc     900

attccttacc atcagattga ttggaataaa caacgacata attgttgcaa ggaggatctg     960

tactaccctc atacctacat ccaagatctc ttatgggatg gtcttcatta ttttagtgag    1020

ccacttatca caaaatggcc cttcgagaag ttaagagcga agggtttgaa aagagtattg    1080

gatctaatgc aatataatgc tgaggaagga cgttacataa ccctaggttc cgttgagaag    1140

tctttacaaa tgatgtgttt ttatgcccta gatccaaatg gaattgactt taaacgacac    1200

cttgctagag tccccgatta cttatgggtg gcggaagatg gtatgaaaat gcaaagtttt    1260

ggtagtcagt tatgggattg tactcttgta actcaagcta ttatcgctag tgatatggtt    1320
```

```
gaagaatatg gagattcact taaaaaagcc aacttttact taaaagaatc acagatcaaa   1380

gaaaacccaa aaggcgattt tgaaaacatg tgtcgtcagt ttacaaaagg ggcatggact   1440

ttcactgatc aagatcaagg gtgggtcgtc tcagattgca ctgctgaagc tgtgaagtgt   1500

ttattggcaa tgtcacaaat gccacaagaa attgccggtg agaaggtgga agttgagcga   1560

ttgtatgatg ccattaacgt ccttctttac ctacagagtc cagaaaccgg tggttttgca   1620

gtttgggagg taccggttcc aaaaccatat ttagagaaat tgaatccttc ggaacttttt   1680

gcagacataa ccgtcgagag agagcatgtt gaatgtacag gctccataat tcaagcgttg   1740

caaacattta aaactctgca tccagggcat cgtgaaaaag aaatagaagt tgctattgaa   1800

aaaggcatac actttttgga aaataggcaa caagaaaatg gttcttggta tggtttttgg   1860

ggtatatgtt atatttatgg aacgtatttt gtgctacaag gattggtagc ttgtggaaaa   1920

acatatgaaa attgtgaagc tgtcaggaaa gctgttaagt tttcctctc gacacaaaac   1980

tcagaaggtg gttggggaga gcactttgag tcatgcccac aagagaaatt tataccttta   2040

gagggcaaca gaacacattt tgtgcatact tcatgggcca tgcttggtct tctatatggt   2100

ggacaggttg aaagagatcc gacaccatta cacaaggcat caaaattgct cataaatgga   2160

caaacggata atggagattt tcctcaacag gaaataacag gagtgtacaa caagaattgc   2220

atgttacatt atgcagaata taggaacact ttcccgctat gggcacttgg agagtaccgc   2280

aagcgtgttt ggttagcaaa acaagaaacc taa                                 2313
```

<210> SEQ ID NO 6
<211> LENGTH: 770
<212> TYPE: PRT
<213> ORGANISM: Taraxacum koksaghyz

<400> SEQUENCE: 6

```
Met Trp Lys Leu Arg Ile Gly Glu Lys Asn Gly Lys Phe Asn Ile Gly
1               5                   10                  15

Asp Gly Asn Gly Asp Glu Tyr Leu Tyr Ser Thr Asn Asn Phe Val Gly
            20                  25                  30

Arg Gln Thr Trp Glu Phe Asp Pro Asp Ala Gly Thr Gln Glu Glu Arg
        35                  40                  45

Asp Glu Val Glu Arg Leu Arg Glu Gln Phe Leu Ile Asn Lys Lys Lys
    50                  55                  60

Leu Asp Ile Ser Cys Cys Ala Asp Leu Leu Met Arg Asn Gln Leu Ile
65                  70                  75                  80

Lys Glu Ser Gly Ile Asp Leu Ile Ser Glu Ala Pro Val Lys Leu Gly
                85                  90                  95

His Asp Glu Asp Val Asn Tyr Lys Ala Val Thr Thr Ala Val Arg Lys
            100                 105                 110

Ala Val Arg Leu Asn Arg Ala Ile Gln Ala Trp Asp Gly His Trp Pro
        115                 120                 125

Ala Glu Asn Ala Gly Pro Leu Phe Phe Thr Pro Pro Leu Ile Ile Val
    130                 135                 140

Leu Tyr Ile Ser Gly Thr Leu Asp Asn Val Leu Thr Gln Asp His Lys
145                 150                 155                 160

Lys Glu Met Ile Arg Tyr Met Tyr Ile His Gln Asn Glu Asp Gly Gly
                165                 170                 175

Trp Gly Phe Tyr Ile Ser Gly Arg Ser Thr Met Ile Gly Thr Ala Leu
            180                 185                 190

Asn Tyr Val Gly Leu Arg Leu Leu Gly Glu Asp Asp Asn Asp Ala Ile
```

```
        195                 200                 205

Ala Lys Gly Arg Lys Trp Ile Leu Asp His Gly Gly Ala Thr Ser Ile
    210                 215                 220

Pro Ser Trp Gly Lys Val Tyr Leu Ser Val Leu Gly Val Tyr Glu Trp
225                 230                 235                 240

Ala Gly Cys Asn Pro Leu Pro Pro Glu Phe Trp Leu Phe Pro Ser Phe
                245                 250                 255

Phe Pro Tyr His Pro Ala Lys Met Trp Cys Tyr Cys Arg Thr Thr Tyr
            260                 265                 270

Met Pro Met Ser Tyr Leu Tyr Gly Arg Gly Ile Gln Gly Pro Ile Thr
        275                 280                 285

Asp Leu Val Lys Ser Leu Arg Lys Glu Ile His Val Ile Pro Tyr His
    290                 295                 300

Gln Ile Asp Trp Asn Lys Gln Arg His Asn Cys Cys Lys Glu Asp Leu
305                 310                 315                 320

Tyr Tyr Pro His Thr Tyr Ile Gln Asp Leu Leu Trp Asp Gly Leu His
                325                 330                 335

Tyr Phe Ser Glu Pro Leu Ile Thr Lys Trp Pro Phe Glu Lys Leu Arg
            340                 345                 350

Ala Lys Gly Leu Lys Arg Val Leu Asp Leu Met Gln Tyr Asn Ala Glu
        355                 360                 365

Glu Gly Arg Tyr Ile Thr Leu Gly Ser Val Glu Lys Ser Leu Gln Met
    370                 375                 380

Met Cys Phe Tyr Ala Leu Asp Pro Asn Gly Ile Asp Phe Lys Arg His
385                 390                 395                 400

Leu Ala Arg Val Pro Asp Tyr Leu Trp Val Ala Glu Asp Gly Met Lys
                405                 410                 415

Met Gln Ser Phe Gly Ser Gln Leu Trp Asp Cys Thr Leu Val Thr Gln
            420                 425                 430

Ala Ile Ile Ala Ser Asp Met Val Glu Glu Tyr Gly Asp Ser Leu Lys
        435                 440                 445

Lys Ala Asn Phe Tyr Leu Lys Glu Ser Gln Ile Lys Glu Asn Pro Lys
    450                 455                 460

Gly Asp Phe Glu Asn Met Cys Arg Gln Phe Thr Lys Gly Ala Trp Thr
465                 470                 475                 480

Phe Thr Asp Gln Asp Gln Gly Trp Val Val Ser Asp Cys Thr Ala Glu
                485                 490                 495

Ala Val Lys Cys Leu Leu Ala Met Ser Gln Met Pro Gln Glu Ile Ala
            500                 505                 510

Gly Glu Lys Val Glu Val Glu Arg Leu Tyr Asp Ala Ile Asn Val Leu
        515                 520                 525

Leu Tyr Leu Gln Ser Pro Glu Thr Gly Gly Phe Ala Val Trp Glu Val
    530                 535                 540

Pro Val Pro Lys Pro Tyr Leu Glu Lys Leu Asn Pro Ser Glu Leu Phe
545                 550                 555                 560

Ala Asp Ile Thr Val Glu Arg Glu His Val Glu Cys Thr Gly Ser Ile
                565                 570                 575

Ile Gln Ala Leu Gln Thr Phe Lys Thr Leu His Pro Gly His Arg Glu
            580                 585                 590

Lys Glu Ile Glu Val Ala Ile Glu Lys Gly Ile His Phe Leu Glu Asn
        595                 600                 605

Arg Gln Gln Glu Asn Gly Ser Trp Tyr Gly Phe Trp Gly Ile Cys Tyr
    610                 615                 620
```

```
Ile Tyr Gly Thr Tyr Phe Val Leu Gln Gly Leu Val Ala Cys Gly Lys
625                 630                 635                 640

Thr Tyr Glu Asn Cys Glu Ala Val Arg Lys Ala Val Lys Phe Phe Leu
                645                 650                 655

Ser Thr Gln Asn Ser Glu Gly Gly Trp Gly Glu His Phe Glu Ser Cys
            660                 665                 670

Pro Gln Glu Lys Phe Ile Pro Leu Glu Gly Asn Arg Thr His Phe Val
        675                 680                 685

His Thr Ser Trp Ala Met Leu Gly Leu Leu Tyr Gly Gly Gln Val Glu
    690                 695                 700

Arg Asp Pro Thr Pro Leu His Lys Ala Ser Lys Leu Leu Ile Asn Gly
705                 710                 715                 720

Gln Thr Asp Asn Gly Asp Phe Pro Gln Gln Glu Ile Thr Gly Val Tyr
                725                 730                 735

Asn Lys Asn Cys Met Leu His Tyr Ala Glu Tyr Arg Asn Thr Phe Pro
            740                 745                 750

Leu Trp Ala Leu Gly Glu Tyr Arg Lys Arg Val Trp Leu Ala Lys Gln
        755                 760                 765

Glu Thr
    770


<210> SEQ ID NO 7
<211> LENGTH: 2298
<212> TYPE: DNA
<213> ORGANISM: Taraxacum koksaghyz

<400> SEQUENCE: 7

atgtgggagt taaagatagc ggaaggggat ggcccttatt tgtacagtac caacaacttt      60

gttggtagac aattttggga gtttaatcca gatgctggaa ctccagaaga gaaagaggaa     120

atcgaaaagg ttcgccagaa atttaaagat aatcgtaaaa aaggaggatt tcatgcttgt     180

ggcgatctac tcatgcggat gcagctaatg aaagaaaatg caatcgatct tacgagcata     240

cttccggtga gaataagtga gggcgagcaa gtaaattatg aagcaacaac aattgcagta     300

cgaaaagcag ttcgactaca tcgtggaatc caagcgaaag atggacattg gcctgctgaa     360

aatgctggtc ccttgttttt taccccctca cttgttattg ctttatatat cagtggtacc     420

attaataccg tcttaagtga agaacacaaa aaagagatga tacgatactt ctacaatcat     480

caaaatgaag atgggggatg gggttctat atcgagggtc atagtacaat gatcggatca     540

gtactgagtt atgtagccct acgtctactc ggagaaggag aagatgatgg agatggtgca     600

atcgcccgag cacgcaagtg gatacttgac catggtggtg ctgcctctat tccctcatgg     660

ggaaaggttt atctttcggt gcttggagtg tacgaatggg agggctgcaa tccattgcca     720

ccagaatttt ggctctttcc ttcgacattt ccttttcatc ctgctgagat gtggtgctac     780

tgccggacaa cctacatgcc tatgtcatat ttatatggga aagaatcca aggacctctc     840

acccctctcg tttcctcatt gagaaaagaa attcatttaa cccctttga ggatattaat     900

tggaataaac aaaggaataa ttgttgtaag aaggacttct actatccaca ttcatttctt     960

caagatgcat tgtggcatag ccttcactac cttactgagc ctgtcctcaa gtattggcca    1020

ttttcaaaac tacgagggag atctcttgat agagttgtag aactaatgcg ctatgaatct    1080

gaagagacca gatatatgac catagggtgt gtcgaaaaaa gtctacaaat gatgtgttgg    1140

tgggcagaaa atcctaatgg tgatgagttc aaatatcatc tagcaagagt tccagattac    1200
```

```
ttatggattg cagaagatgg aatgacaatg catagtttcg gtagtcaagt gtgggattgt   1260
tctcttgcaa ctcaagcaat tatagcaagt aacatggtag aggaatatga tgattgtctg   1320
gaaaaggcac acttctattt aagagaatca caggtaaaag aaaatccttc aggagatttc   1380
actcgcatgt gtcggcagtt cactaaggga tcgtggacct tctctgatca agatcatgga   1440
tggacagtct ctgactgtac agctgaagca ctaaagtgtc tattgttact atcaaacatg   1500
cctaaaaata tcgctggaga gaaagatgac actgccagac tatatgaagc agttaatgtg   1560
cttctttaca tgcaaagtcc tgtaagtggg ggatttgctg tttgggagcc accaattcca   1620
aaaccgtttc tacagcttct taatccttca gagatttttg cagatatcgt cgttgagaaa   1680
gagcatgtgg agacaacatc ttccattatc ggagctctga tcgagttcaa acgggtccat   1740
ccaaaccaca gaaaagaaga aatagaatac tcaatctcga atggaatacg ttatctcgag   1800
gaaacacaat ggcatgatgg ttcatggtat ggttattggg gagtatgctt catatatgga   1860
accttctttg ctctgagagc attaagtact gccggaaaga catataagaa taacgaagca   1920
gcctgtaaag gtgtcaaatt cttattgtcg atacaaaatg aagagggggg ttggggagag   1980
agcctactat cttgccctac tgaggtatat acaccgttgg atggaaatca gacaaatttg   2040
gtgcaaacat cgtgggctat gcttggccta ctttttggtg ggcaggtgga tagagatccc   2100
acgcctttac atagagcagc aaagctgttg attaatgctc agatggataa tggagatttt   2160
cctcaacagg aaattaccgg agtctacatg aagaattgct tgctgcttta cgcacaatac   2220
agaaacattt ttccactatg ggcacttggg gaataccgta aacgtgtttg gagcataaaa   2280
aagggtattc aaaattaa                                                 2298
```

<210> SEQ ID NO 8
<211> LENGTH: 765
<212> TYPE: PRT
<213> ORGANISM: Taraxacum koksaghyz

<400> SEQUENCE: 8

```
Met Trp Glu Leu Lys Ile Ala Glu Gly Asp Gly Pro Tyr Leu Tyr Ser
1               5                   10                  15

Thr Asn Asn Phe Val Gly Arg Gln Phe Trp Glu Phe Asn Pro Asp Ala
            20                  25                  30

Gly Thr Pro Glu Glu Lys Glu Glu Ile Glu Lys Val Arg Gln Lys Phe
        35                  40                  45

Lys Asp Asn Arg Lys Lys Gly Gly Phe His Ala Cys Gly Asp Leu Leu
    50                  55                  60

Met Arg Met Gln Leu Met Lys Glu Asn Ala Ile Asp Leu Thr Ser Ile
65                  70                  75                  80

Leu Pro Val Arg Ile Ser Glu Gly Glu Gln Val Asn Tyr Glu Ala Thr
                85                  90                  95

Thr Ile Ala Val Arg Lys Ala Val Arg Leu His Arg Gly Ile Gln Ala
            100                 105                 110

Lys Asp Gly His Trp Pro Ala Glu Asn Ala Gly Pro Leu Phe Phe Thr
        115                 120                 125

Pro Pro Leu Val Ile Ala Leu Tyr Ile Ser Gly Thr Ile Asn Thr Val
    130                 135                 140

Leu Ser Glu Glu His Lys Lys Glu Met Ile Arg Tyr Phe Tyr Asn His
145                 150                 155                 160

Gln Asn Glu Asp Gly Gly Trp Gly Phe Tyr Ile Glu Gly His Ser Thr
                165                 170                 175
```

-continued

```
Met Ile Gly Ser Val Leu Ser Tyr Val Ala Leu Arg Leu Leu Gly Glu
            180                 185                 190

Gly Glu Asp Asp Gly Asp Gly Ala Ile Ala Arg Ala Arg Lys Trp Ile
        195                 200                 205

Leu Asp His Gly Gly Ala Ala Ser Ile Pro Ser Trp Gly Lys Val Tyr
    210                 215                 220

Leu Ser Val Leu Gly Val Tyr Glu Trp Glu Gly Cys Asn Pro Leu Pro
225                 230                 235                 240

Pro Glu Phe Trp Leu Phe Pro Ser Thr Phe Pro Phe His Pro Ala Glu
                245                 250                 255

Met Trp Cys Tyr Cys Arg Thr Thr Tyr Met Pro Met Ser Tyr Leu Tyr
            260                 265                 270

Gly Lys Arg Ile Gln Gly Pro Leu Thr Pro Leu Val Ser Ser Leu Arg
        275                 280                 285

Lys Glu Ile His Leu Thr Pro Phe Glu Asp Ile Asn Trp Asn Lys Gln
    290                 295                 300

Arg Asn Asn Cys Cys Lys Lys Asp Phe Tyr Tyr Pro His Ser Phe Leu
305                 310                 315                 320

Gln Asp Ala Leu Trp His Ser Leu His Tyr Leu Thr Glu Pro Val Leu
                325                 330                 335

Lys Tyr Trp Pro Phe Ser Lys Leu Arg Gly Arg Ser Leu Asp Arg Val
            340                 345                 350

Val Glu Leu Met Arg Tyr Glu Ser Glu Glu Thr Arg Tyr Met Thr Ile
        355                 360                 365

Gly Cys Val Glu Lys Ser Leu Gln Met Met Cys Trp Trp Ala Glu Asn
    370                 375                 380

Pro Asn Gly Asp Glu Phe Lys Tyr His Leu Ala Arg Val Pro Asp Tyr
385                 390                 395                 400

Leu Trp Ile Ala Glu Asp Gly Met Thr Met His Ser Phe Gly Ser Gln
                405                 410                 415

Val Trp Asp Cys Ser Leu Ala Thr Gln Ala Ile Ile Ala Ser Asn Met
            420                 425                 430

Val Glu Glu Tyr Asp Asp Cys Leu Glu Lys Ala His Phe Tyr Leu Arg
        435                 440                 445

Glu Ser Gln Val Lys Glu Asn Pro Ser Gly Asp Phe Thr Arg Met Cys
    450                 455                 460

Arg Gln Phe Thr Lys Gly Ser Trp Thr Phe Ser Asp Gln Asp His Gly
465                 470                 475                 480

Trp Thr Val Ser Asp Cys Thr Ala Glu Ala Leu Lys Cys Leu Leu Leu
                485                 490                 495

Leu Ser Asn Met Pro Lys Asn Ile Ala Gly Glu Lys Asp Asp Thr Ala
            500                 505                 510

Arg Leu Tyr Glu Ala Val Asn Val Leu Leu Tyr Met Gln Ser Pro Val
        515                 520                 525

Ser Gly Gly Phe Ala Val Trp Glu Pro Pro Ile Pro Lys Pro Phe Leu
    530                 535                 540

Gln Leu Leu Asn Pro Ser Glu Ile Phe Ala Asp Ile Val Val Glu Lys
545                 550                 555                 560

Glu His Val Glu Thr Thr Ser Ser Ile Ile Gly Ala Leu Ile Glu Phe
                565                 570                 575

Lys Arg Val His Pro Asn His Arg Lys Glu Glu Ile Glu Tyr Ser Ile
            580                 585                 590

Ser Asn Gly Ile Arg Tyr Leu Glu Glu Thr Gln Trp His Asp Gly Ser
```

```
        595                 600                 605

Trp Tyr Gly Tyr Trp Gly Val Cys Phe Ile Tyr Gly Thr Phe Phe Ala
    610                 615                 620

Leu Arg Ala Leu Ser Thr Ala Gly Lys Thr Tyr Lys Asn Asn Glu Ala
625                 630                 635                 640

Ala Cys Lys Gly Val Lys Phe Leu Leu Ser Ile Gln Asn Glu Glu Gly
                645                 650                 655

Gly Trp Gly Glu Ser Leu Leu Ser Cys Pro Thr Glu Val Tyr Thr Pro
            660                 665                 670

Leu Asp Gly Asn Gln Thr Asn Leu Val Gln Thr Ser Trp Ala Met Leu
        675                 680                 685

Gly Leu Leu Phe Gly Gly Gln Val Asp Arg Asp Pro Thr Pro Leu His
    690                 695                 700

Arg Ala Ala Lys Leu Leu Ile Asn Ala Gln Met Asp Asn Gly Asp Phe
705                 710                 715                 720

Pro Gln Gln Glu Ile Thr Gly Val Tyr Met Lys Asn Cys Leu Leu Leu
                725                 730                 735

Tyr Ala Gln Tyr Arg Asn Ile Phe Pro Leu Trp Ala Leu Gly Glu Tyr
            740                 745                 750

Arg Lys Arg Val Trp Ser Ile Lys Lys Gly Ile Gln Asn
        755                 760                 765
```

<210> SEQ ID NO 9
<211> LENGTH: 2286
<212> TYPE: DNA
<213> ORGANISM: Taraxacum koksaghyz

<400> SEQUENCE: 9

```
atgtggaggt taagaatcgg gcaagggaac aaagacgatc cttatttgtt cagcacaaat     60

aattttgtgg gaagacaaat atgggagtat gacgaaaact ataaagcaac tccagaagag    120

ttggaagaag ttaaacaagc ccgatcttct ttctggaaca accgtcacaa gcaaaggcca    180

tgtgatgatc gtctttggcg ttttcagttt ctaagggaga agaatttcaa acaaacaata    240

ccaagagaga ttatcgtgga tgaaagtgag ataaagtatg aaactgtcga caatgcattg    300

aaaagggcag ttcgttattg gacggctcta caagcaagcg acggccactg gccttcagcc    360

aacaacggct gccactattt tacaccaccc atcgtcatgt gtttgtatat aacaggacat    420

cttgatacat tcttctcgac ccaagataaa gaagaaatgc ttcgttatat atactgtcac    480

cagaatgaag atggaggatg ggatttcac cttgaaggcc atagcatcat gttttgcacc    540

gcggtcaatt atatatgcat gcgaatgctt ggagaaggac ccgatggtgg cctcgatggt    600

gcgtgttcta gagcacgtaa gtggattctt gatcatggca gtgtcaccgc catcccctca    660

tggggaaaga cttggttatc ggcacttggg ctatatgagt ggtctggaag caatccaatg    720

cctccagagt tttggcttct cccatcgttc cttcctatat cgccaggaaa gatatggtgt    780

tattgtcgga tgatttatat gccaatgtct tatttatatg ggaagagatt cattggtccg    840

atcactcctc taattctgca gttgagaaaa gagctttatt ctataccota tcatgaagtc    900

aattggagga aagtaagaca tctttgcgcg aaggaggaca tatattatcc tcacccttgg    960

ctacaagatc tctcttggga tactcttcat ttggcagtgg agcctatcct aactcgttgg   1020

ccattcaaga gcatgattcg agagaaagct cttaaaacca caatgagaca catacattat   1080

gaagacgaga atagtcgcta cattaccatc ggttgcgttg aaaaagcact atgtatgctt   1140

gcatgttggg tggaggatcc tcatggggat tatttcaaga aacacctaag cagaatccgc   1200
```

```
gatatgattt gggtacaaga agatggcatg acggttcaga gttttggtag ccagcaatgg   1260

gattcttctt tgagcgttct tgctttgata gattgcaata tgatagatga aactggatca   1320

acactaaaaa aaggacatga attcatcaaa aactctcagg ttcgggacaa cccttcaggc   1380

gacttcaaaa gcatgtatcg tcacatttct aagggaggtt ggacttattc cgaccaagat   1440

cacggatggc aagtttctga ttgcactgct cacgggttaa tgtcttgcct ccttttgtca   1500

aagatgccac tggaaatagt tggagagaag atggaaactg agcgtttatt cgattgcata   1560

aatttactgc tttcactaca gtacaaaaat ggaggtttct cggg ttggga acctgcaggt   1620

gctccaaaat ggttggagat gcttaaccct tcggaaatgt ttgcagacat tatgatcgaa   1680

attcaatacg ttgagtgtac atcatcggcg ttgcaggctt tgatattgtt taaaaagtta   1740

tatcctgaac atcggagtca agaagttgca aattgcattt ctaatgctat tcggtttctt   1800

gaagacacac aatggccgga tggatcatgg tatggagagt ggggtgtatg cttcacatat   1860

gctacgtggt ttgctacaaa agggttagct gcagctggca agacatatga gcaatctccg   1920

acaattcgta aggccactga gtttttactg aaacatcaac aagaagatgg tggttgggga   1980

gaaagctatc tttcttgccc taacttggaa tttacatctt tagaagaaag caggtcgaac   2040

gtggtgcaaa catcatggtg cttgatgagt ctaatccagt gtggacaggc agagagggat   2100

ttgacaccga ttcatcgtgg agcaaagttt ctcataaatt ctcaaatgga agatggtgat   2160

ttcccccaaa aggaaatcac ggggtctttt cgtaaaaatt gcatgttaca ctatgcttgc   2220

catagaaaca tatttccaat gtgggctctt gcagaataca agaatcgggt gtctaaaatc   2280

atctaa                                                              2286
```

<210> SEQ ID NO 10
<211> LENGTH: 761
<212> TYPE: PRT
<213> ORGANISM: Taraxacum koksaghyz

<400> SEQUENCE: 10

```
Met Trp Arg Leu Arg Ile Gly Gln Gly Asn Lys Asp Asp Pro Tyr Leu
1               5                   10                  15

Phe Ser Thr Asn Asn Phe Val Gly Arg Gln Ile Trp Glu Tyr Asp Glu
            20                  25                  30

Asn Tyr Lys Ala Thr Pro Glu Glu Leu Glu Glu Val Lys Gln Ala Arg
        35                  40                  45

Ser Ser Phe Trp Asn Asn Arg His Lys Gln Arg Pro Cys Asp Asp Arg
    50                  55                  60

Leu Trp Arg Phe Gln Phe Leu Arg Glu Lys Asn Phe Lys Gln Thr Ile
65                  70                  75                  80

Pro Arg Glu Ile Ile Val Asp Glu Ser Glu Ile Lys Tyr Glu Thr Val
                85                  90                  95

Asp Asn Ala Leu Lys Arg Ala Val Arg Tyr Trp Thr Ala Leu Gln Ala
            100                 105                 110

Ser Asp Gly His Trp Pro Ser Ala Asn Asn Gly Cys His Tyr Phe Thr
        115                 120                 125

Pro Pro Ile Val Met Cys Leu Tyr Ile Thr Gly His Leu Asp Thr Phe
    130                 135                 140

Phe Ser Thr Gln Asp Lys Glu Glu Met Leu Arg Tyr Ile Tyr Cys His
145                 150                 155                 160

Gln Asn Glu Asp Gly Gly Trp Gly Phe His Leu Glu Gly His Ser Ile
                165                 170                 175
```

```
Met Phe Cys Thr Ala Val Asn Tyr Ile Cys Met Arg Met Leu Gly Glu
            180                 185                 190

Gly Pro Asp Gly Gly Leu Asp Gly Ala Cys Ser Arg Ala Arg Lys Trp
        195                 200                 205

Ile Leu Asp His Gly Ser Val Thr Ala Ile Pro Ser Trp Gly Lys Thr
    210                 215                 220

Trp Leu Ser Ala Leu Gly Leu Tyr Glu Trp Ser Gly Ser Asn Pro Met
225                 230                 235                 240

Pro Pro Glu Phe Trp Leu Leu Pro Ser Phe Leu Pro Ile Ser Pro Gly
                245                 250                 255

Lys Ile Trp Cys Tyr Cys Arg Met Ile Tyr Met Pro Met Ser Tyr Leu
            260                 265                 270

Tyr Gly Lys Arg Phe Ile Gly Pro Ile Thr Pro Leu Ile Leu Gln Leu
        275                 280                 285

Arg Lys Glu Leu Tyr Ser Ile Pro Tyr His Glu Val Asn Trp Arg Lys
    290                 295                 300

Val Arg His Leu Cys Ala Lys Glu Asp Ile Tyr Tyr Pro His Pro Trp
305                 310                 315                 320

Leu Gln Asp Leu Ser Trp Asp Thr Leu His Leu Ala Val Glu Pro Ile
                325                 330                 335

Leu Thr Arg Trp Pro Phe Lys Ser Met Ile Arg Glu Lys Ala Leu Lys
            340                 345                 350

Thr Thr Met Arg His Ile His Tyr Glu Asp Glu Asn Ser Arg Tyr Ile
        355                 360                 365

Thr Ile Gly Cys Val Glu Lys Ala Leu Cys Met Leu Ala Cys Trp Val
    370                 375                 380

Glu Asp Pro His Gly Asp Tyr Phe Lys Lys His Leu Ser Arg Ile Arg
385                 390                 395                 400

Asp Met Ile Trp Val Gln Glu Asp Gly Met Thr Val Gln Ser Phe Gly
                405                 410                 415

Ser Gln Gln Trp Asp Ser Ser Leu Ser Val Leu Ala Leu Ile Asp Cys
            420                 425                 430

Asn Met Ile Asp Glu Thr Gly Ser Thr Leu Lys Lys Gly His Glu Phe
        435                 440                 445

Ile Lys Asn Ser Gln Val Arg Asp Asn Pro Ser Gly Asp Phe Lys Ser
    450                 455                 460

Met Tyr Arg His Ile Ser Lys Gly Gly Trp Thr Tyr Ser Asp Gln Asp
465                 470                 475                 480

His Gly Trp Gln Val Ser Asp Cys Thr Ala His Gly Leu Met Ser Cys
                485                 490                 495

Leu Leu Leu Ser Lys Met Pro Leu Glu Ile Val Gly Glu Lys Met Glu
            500                 505                 510

Thr Glu Arg Leu Phe Asp Cys Ile Asn Leu Leu Leu Ser Leu Gln Tyr
        515                 520                 525

Lys Asn Gly Gly Phe Ser Gly Trp Glu Pro Ala Gly Ala Pro Lys Trp
    530                 535                 540

Leu Glu Met Leu Asn Pro Ser Glu Met Phe Ala Asp Ile Met Ile Glu
545                 550                 555                 560

Ile Gln Tyr Val Glu Cys Thr Ser Ser Ala Leu Gln Ala Leu Ile Leu
                565                 570                 575

Phe Lys Lys Leu Tyr Pro Glu His Arg Ser Gln Glu Val Ala Asn Cys
            580                 585                 590
```

```
Ile Ser Asn Ala Ile Arg Phe Leu Glu Asp Thr Gln Trp Pro Asp Gly
        595                 600                 605

Ser Trp Tyr Gly Glu Trp Gly Val Cys Phe Thr Tyr Ala Thr Trp Phe
    610                 615                 620

Ala Thr Lys Gly Leu Ala Ala Ala Gly Lys Thr Tyr Glu Gln Ser Pro
625                 630                 635                 640

Thr Ile Arg Lys Ala Thr Glu Phe Leu Leu Lys His Gln Gln Glu Asp
                645                 650                 655

Gly Gly Trp Gly Glu Ser Tyr Leu Ser Cys Pro Asn Leu Glu Phe Thr
            660                 665                 670

Ser Leu Glu Glu Ser Arg Ser Asn Val Val Gln Thr Ser Trp Cys Leu
        675                 680                 685

Met Ser Leu Ile Gln Cys Gly Gln Ala Glu Arg Asp Leu Thr Pro Ile
    690                 695                 700

His Arg Gly Ala Lys Phe Leu Ile Asn Ser Gln Met Glu Asp Gly Asp
705                 710                 715                 720

Phe Pro Gln Lys Glu Ile Thr Gly Ser Phe Arg Lys Asn Cys Met Leu
                725                 730                 735

His Tyr Ala Cys His Arg Asn Ile Phe Pro Met Trp Ala Leu Ala Glu
            740                 745                 750

Tyr Lys Asn Arg Val Ser Lys Ile Ile
        755                 760


<210> SEQ ID NO 11
<211> LENGTH: 2283
<212> TYPE: DNA
<213> ORGANISM: Taraxacum koksaghyz

<400> SEQUENCE: 11

atgtggaaat taaagatagc agaaggaggc aatgatccat atctccactc cacaaataac      60

ttcattggga ggcaaatatg ggagtttgac tcgaaccatg gcaccccaga agaccgagcc     120

gaggccgaac atgctcgaat caatttctgg aaccttagac atcgggtcaa gcccagtagt     180

gatgtccttt ggcgcatgca gtttttaaaa gagaaacaat tcaaacaaac gatagcccaa     240

gtgaaaatag aggaatttga agagatatct tatgaaaaag ctacagtcac attgaagagg     300

tgtgtgaacc tttttgcagc tttgcaggcc gatgatggtc actggcctgc tgaaaatgcg     360

ggtccactat atttcatgca gccgttggtt atttgtttgt atatcactgg tcatcttgac     420

attgttttcc cagaagaaca ccgaaaagaa atcctacatt atatgtattg ccatcagaat     480

gaagacggtg gttggggatt tcacatcgag ggtcatagca gcatgttctg caccacccta     540

agttacattt gtatgcggct tttaggagaa ggggtggatg gtggtttgaa tggtgcatgc     600

accaaagccc gcaaatggat tctggatcat ggctctgtca ctgccattgc atcatggggc     660

aaaacatggc tttccatact tggagtgtgt gagtgggcag gaaccaaccc aatgccccca     720

gagttctgga tcctcccttc tttccttcct atgtatccag cgaaactatg gtgctattgt     780

cgactggtat acatgccaat gtcataccta tacggaaaaa gattcgttgg tcctattact     840

cctttaattt tacagcttag agacgaactt tacttacaac cttacaatga aatcaactgg     900

aagagcatac gacatttgtg tgctaaggaa gatctatact atcctcatcc attactacaa     960

gatttaatgt gggatagttt atatatttgc attgagcctc tattaaatcg ctggccatta    1020

aataaattgc gtcagaaagc acttgaaaca acaatgaaac atattcatta tgaagatgag    1080

aatagccgtt atatcaccat tggttcagtg gtaaaggtgt tgtgtatgct tgcatgttgg    1140
```

```
gttgaagaac caaatggcgt atgtttcaag aagcatcttg ctcgaatccc agattatata   1200

tggattgctg aagacggaat gaaaatgcag agttttggca gtcaagggtg ggatgctagt   1260

ttagccatcc aagctctttt ggctactgat cttacagatg aaatcgggtc tactttgatg   1320

aaaggacaca aatttgttaa agcttcacag gttaaagata atccttctgg atactttaaa   1380

aacatgcaca gacatatttc caaagggtca tggagctttt cagatcaaga ccatggatgg   1440

caaggttccg acaccactgc tgaagcattg aagtgttgtc tcctattctc aacaatgcca   1500

ccagaaattg ttggtgagaa aatgaaacct gagcaactga atgatgcggt caatgtgata   1560

ctttccctac agagcaaaaa cggcgggtta gcatcatggg aaccagcagg atcatcagaa   1620

tggttggaga ttttcaatcc tacagagttc tttgctgaca tcgtcattga gcacgagtat   1680

gttgagtgca catcatcagc aattcaggca atcgttttat ttaacaagtt atacccgcaa   1740

catagaaaaa aagagataga aacttttctt acaggtgcaa gtggatacct agagaaatta   1800

cagacaaaag atggttcatg gtacggaaac tggggcgtgt gttttacata tggtacatgg   1860

tttggtattg gtggattgac agctgtcggt aaaacattg aaaattgtca agcaattcaa   1920

aaagccgtta aatttctgtt ggaaacacaa ctagaagatg gcggttgggg agaaagctac   1980

aaatcctgtc cagaaaaaat atacataccc ctagaaggag gccggtcaaa tttagtgcac   2040

acttcatggg ctatgattgg actaattcag tctcaatgga tggagagaga ctcaacaccc   2100

atacacaaag cagccaggtt attgatcaat tcacagttag aaaacggtga ttttccacaa   2160

caggaaataa ccggagtatt catgaagaac tgcatgttac actacgcact ctacaggaac   2220

atatacccaa tgtgggccct agccgattat cgcaaaaagg tgttgtccac gtgtaaaaaa   2280

taa                                                                 2283
```

<210> SEQ ID NO 12
<211> LENGTH: 760
<212> TYPE: PRT
<213> ORGANISM: Taraxacum koksaghyz

<400> SEQUENCE: 12

```
Met Trp Lys Leu Lys Ile Ala Glu Gly Gly Asn Asp Pro Tyr Leu His
1               5                   10                  15

Ser Thr Asn Asn Phe Ile Gly Arg Gln Ile Trp Glu Phe Asp Ser Asn
            20                  25                  30

His Gly Thr Pro Glu Asp Arg Ala Glu Ala Glu His Ala Arg Ile Asn
        35                  40                  45

Phe Trp Asn Leu Arg His Arg Val Lys Pro Ser Ser Asp Val Leu Trp
    50                  55                  60

Arg Met Gln Phe Leu Lys Glu Lys Gln Phe Lys Gln Thr Ile Ala Gln
65                  70                  75                  80

Val Lys Ile Glu Glu Phe Glu Glu Ile Ser Tyr Glu Lys Ala Thr Val
                85                  90                  95

Thr Leu Lys Arg Cys Val Asn Leu Phe Ala Ala Leu Gln Ala Asp Asp
            100                 105                 110

Gly His Trp Pro Ala Glu Asn Ala Gly Pro Leu Tyr Phe Met Gln Pro
        115                 120                 125

Leu Val Ile Cys Leu Tyr Ile Thr Gly His Leu Asp Ile Val Phe Pro
    130                 135                 140

Glu Glu His Arg Lys Glu Ile Leu His Tyr Met Tyr Cys His Gln Asn
145                 150                 155                 160

Glu Asp Gly Gly Trp Gly Phe His Ile Glu Gly His Ser Ser Met Phe
```

```
                165                 170                 175

Cys Thr Thr Leu Ser Tyr Ile Cys Met Arg Leu Leu Gly Glu Gly Val
            180                 185                 190

Asp Gly Gly Leu Asn Gly Ala Cys Thr Lys Ala Arg Lys Trp Ile Leu
        195                 200                 205

Asp His Gly Ser Val Thr Ala Ile Ala Ser Trp Gly Lys Thr Trp Leu
    210                 215                 220

Ser Ile Leu Gly Val Cys Glu Trp Ala Gly Thr Asn Pro Met Pro Pro
225                 230                 235                 240

Glu Phe Trp Ile Leu Pro Ser Phe Leu Pro Met Tyr Pro Ala Lys Leu
                245                 250                 255

Trp Cys Tyr Cys Arg Leu Val Tyr Met Pro Met Ser Tyr Leu Tyr Gly
            260                 265                 270

Lys Arg Phe Val Gly Pro Ile Thr Pro Leu Ile Leu Gln Leu Arg Asp
        275                 280                 285

Glu Leu Tyr Leu Gln Pro Tyr Asn Glu Ile Asn Trp Lys Ser Ile Arg
    290                 295                 300

His Leu Cys Ala Lys Glu Asp Leu Tyr Tyr Pro His Pro Leu Leu Gln
305                 310                 315                 320

Asp Leu Met Trp Asp Ser Leu Tyr Ile Cys Ile Glu Pro Leu Leu Asn
                325                 330                 335

Arg Trp Pro Leu Asn Lys Leu Arg Gln Lys Ala Leu Glu Thr Thr Met
            340                 345                 350

Lys His Ile His Tyr Glu Asp Glu Asn Ser Arg Tyr Ile Thr Ile Gly
        355                 360                 365

Ser Val Val Lys Val Leu Cys Met Leu Ala Cys Trp Val Glu Glu Pro
    370                 375                 380

Asn Gly Val Cys Phe Lys Lys His Leu Ala Arg Ile Pro Asp Tyr Ile
385                 390                 395                 400

Trp Ile Ala Glu Asp Gly Met Lys Met Gln Ser Phe Gly Ser Gln Gly
                405                 410                 415

Trp Asp Ala Ser Leu Ala Ile Gln Ala Leu Leu Ala Thr Asp Leu Thr
            420                 425                 430

Asp Glu Ile Gly Ser Thr Leu Met Lys Gly His Lys Phe Val Lys Ala
        435                 440                 445

Ser Gln Val Lys Asp Asn Pro Ser Gly Tyr Phe Lys Asn Met His Arg
    450                 455                 460

His Ile Ser Lys Gly Ser Trp Ser Phe Ser Asp Gln Asp His Gly Trp
465                 470                 475                 480

Gln Gly Ser Asp Thr Thr Ala Glu Ala Leu Lys Cys Cys Leu Leu Phe
                485                 490                 495

Ser Thr Met Pro Pro Glu Ile Val Gly Glu Lys Met Lys Pro Glu Gln
            500                 505                 510

Leu Asn Asp Ala Val Asn Val Ile Leu Ser Leu Gln Ser Lys Asn Gly
        515                 520                 525

Gly Leu Ala Ser Trp Glu Pro Ala Gly Ser Ser Glu Trp Leu Glu Ile
    530                 535                 540

Phe Asn Pro Thr Glu Phe Phe Ala Asp Ile Val Ile Glu His Glu Tyr
545                 550                 555                 560

Val Glu Cys Thr Ser Ser Ala Ile Gln Ala Ile Val Leu Phe Asn Lys
                565                 570                 575

Leu Tyr Pro Gln His Arg Lys Lys Glu Ile Glu Thr Phe Leu Thr Gly
            580                 585                 590
```

Ala Ser Gly Tyr Leu Glu Lys Leu Gln Thr Lys Asp Gly Ser Trp Tyr
595 600 605

Gly Asn Trp Gly Val Cys Phe Thr Tyr Gly Thr Trp Phe Gly Ile Gly
610 615 620

Gly Leu Thr Ala Val Gly Lys Thr Phe Glu Asn Cys Gln Ala Ile Gln
625 630 635 640

Lys Ala Val Lys Phe Leu Leu Glu Thr Gln Leu Glu Asp Gly Gly Trp
645 650 655

Gly Glu Ser Tyr Lys Ser Cys Pro Glu Lys Ile Tyr Ile Pro Leu Glu
660 665 670

Gly Gly Arg Ser Asn Leu Val His Thr Ser Trp Ala Met Ile Gly Leu
675 680 685

Ile Gln Ser Gln Trp Met Glu Arg Asp Ser Thr Pro Ile His Lys Ala
690 695 700

Ala Arg Leu Leu Ile Asn Ser Gln Leu Glu Asn Gly Asp Phe Pro Gln
705 710 715 720

Gln Glu Ile Thr Gly Val Phe Met Lys Asn Cys Met Leu His Tyr Ala
725 730 735

Leu Tyr Arg Asn Ile Tyr Pro Met Trp Ala Leu Ala Asp Tyr Arg Lys
740 745 750

Lys Val Leu Ser Thr Cys Lys Lys
755 760

<210> SEQ ID NO 13
<211> LENGTH: 2277
<212> TYPE: DNA
<213> ORGANISM: Taraxacum koksaghyz

<400> SEQUENCE: 13
atgtggaaat taaagatagc cgaaggaggc aatgatccat acctccattc cacaaacaac 60
tttatcggga gacaaatatg ggagtttgac ccaaaccatg gaaccacaga agaccgagcc 120
gaggtcgaac aagctcgact cgatttctgg aaccatcgac atcaggtcaa gcctagcagt 180
gatgtccttt ggcgcatgca gtttttgaaa gagaaagaat tcaagcaaac gatagctcag 240
gtgaaaatag aggattctga agagatatcg tatgaaaaaa ctacaaccac attgaggagg 300
tgtgtgagct tttttgcagc gttgcaagcc agtgatggtc actggcctgc tgaaaatgcg 360
ggcccactgt atttcatgca gccattggtt atctgtttat atattactgg tcatcttaac 420
attgttttcc cagaagaata tcgaaaagaa attctacgtt acttatattg ccatcagaat 480
gaagacggtg gttggggatt tcacatcgag ggtcatagca ccatgtttgg gaccaccctc 540
agttacattt gtatgcggct cttaggagaa ggtccggatg gtggtctgaa tggtgcatgc 600
accaaagccc gcaaatggat cctggatcat ggctcagtca ccgccattcc atcatggggc 660
aaaacatggc tttcaatact tggtgtatgt gagtgggcag gaaccaaccc aatgccccca 720
gagttctggc tccttccttc ttttcttcct atgtgtccag caaagatgtg gtgctactgt 780
cggttggtgt acatgccaat gtcctaccta tatggaaaaa gatttgtggg tcccatcact 840
cctttggttc ttcaacttag agatgaatta tacgcacagc cctacgatga gatcaactgg 900
aaaagcatac gccatttgtg tgcaaaggaa gatttatact accctcatcc gttcctacaa 960
gatttaatgt gggatagttt atatatttgc accgagcctc tattaaatcg ctggccgtta 1020
aataaattac gtcaaaaagc acttgataca acaatgaaac atattcatta tgaagatgag 1080
aatagtcgtt atatcaccat tggttcggtg gtaaagccac tgtgtatgct tgcatgttgg 1140

```
gttgaagatc caaatggcgt ttgtttcaaa aaacatattg cacgaatccc tgattacatc   1200

tgggttgctg aagacggaat gaaaatgcag agttttggta gtcaaaagtg ggatgctggt   1260

tttgcgatcc aagctctatt ggctgctgat cttactgaag aaaatggatc tactttgatg   1320

aaaggacatg aatttattaa agcttcacag gttaaagata atccttctgg agactttaaa   1380

agcatgcaca ggcatatttc gaaagggtca tggactttct cagatcaaga tcacggatgg   1440

caaatttctg actgtactgc tgaaggacta aagtgttgtc tactattctt aacaatgcca   1500

gcggaaatcg ttggtgaaca tatgaaacct gagcaattta atgacgcggt caatgtaata   1560

ctttccctac agagcaaaaa cggtgggcta gcggcatggg aaccagcagg atcgtctgaa   1620

tggttggagg ttcttaatcc tacggagttc tttgctgaca ttgtaattga gcacgagtat   1680

gttgagtgca catcgtcagc aagtcaggca ctagttttgt ttaagaagtt ataccccgga   1740

caccggagaa aagagatcga aagttttctt acaggtgcaa gtggatacct ggagaaaata   1800

cagatggaag atggttcatg gtatggaaac tggggggtgt gttttacata tggtacctgg   1860

tttgctcttg gaggactgac ggctgtcggt aagacgtttg aaaattgtct agcaatccga   1920

aaagccgtca agtttctgtt agaaactcag ctggaagatg gtgggtgggg agaaagttac   1980

aaatcttgcc ctgaaaagag atatgtacca ctggaagaag gccggtcaaa tttggtacac   2040

acggcatggg gtatgatggg actgattcat tctcaacaga tggagagaga cccgatgccc   2100

ctacacaaag cagcaaagtt attgatcaat tcccagttgg aaaatggtga ttttccacaa   2160

cagaaaatag ctggagtgtt caagatgaac tgcatgctac actatgcatt gtacaggaat   2220

atattcccaa tgtgggccct tgctgattat cgcaagcatg tgctgaaagg gatctag      2277
```

<210> SEQ ID NO 14
<211> LENGTH: 758
<212> TYPE: PRT
<213> ORGANISM: Taraxacum koksaghyz

<400> SEQUENCE: 14

```
Met Trp Lys Leu Lys Ile Ala Glu Gly Gly Asn Asp Pro Tyr Leu His
1               5                   10                  15

Ser Thr Asn Asn Phe Ile Gly Arg Gln Ile Trp Glu Phe Asp Pro Asn
            20                  25                  30

His Gly Thr Thr Glu Asp Arg Ala Glu Val Glu Gln Ala Arg Leu Asp
        35                  40                  45

Phe Trp Asn His Arg His Gln Val Lys Pro Ser Ser Asp Val Leu Trp
    50                  55                  60

Arg Met Gln Phe Leu Lys Glu Lys Glu Phe Lys Gln Thr Ile Ala Gln
65                  70                  75                  80

Val Lys Ile Glu Asp Ser Glu Glu Ile Ser Tyr Glu Lys Thr Thr Thr
                85                  90                  95

Thr Leu Arg Arg Cys Val Ser Phe Phe Ala Ala Leu Gln Ala Ser Asp
            100                 105                 110

Gly His Trp Pro Ala Glu Asn Ala Gly Pro Leu Tyr Phe Met Gln Pro
        115                 120                 125

Leu Val Ile Cys Leu Tyr Ile Thr Gly His Leu Asn Ile Val Phe Pro
    130                 135                 140

Glu Glu Tyr Arg Lys Glu Ile Leu Arg Tyr Leu Tyr Cys His Gln Asn
145                 150                 155                 160

Glu Asp Gly Gly Trp Gly Phe His Ile Glu Gly His Ser Thr Met Phe
                165                 170                 175
```

```
Gly Thr Thr Leu Ser Tyr Ile Cys Met Arg Leu Leu Gly Glu Gly Pro
            180                 185                 190

Asp Gly Gly Leu Asn Gly Ala Cys Thr Lys Ala Arg Lys Trp Ile Leu
        195                 200                 205

Asp His Gly Ser Val Thr Ala Ile Pro Ser Trp Gly Lys Thr Trp Leu
    210                 215                 220

Ser Ile Leu Gly Val Cys Glu Trp Ala Gly Thr Asn Pro Met Pro Pro
225                 230                 235                 240

Glu Phe Trp Leu Leu Pro Ser Phe Leu Pro Met Cys Pro Ala Lys Met
                245                 250                 255

Trp Cys Tyr Cys Arg Leu Val Tyr Met Pro Met Ser Tyr Leu Tyr Gly
            260                 265                 270

Lys Arg Phe Val Gly Pro Ile Thr Pro Leu Val Leu Gln Leu Arg Asp
        275                 280                 285

Glu Leu Tyr Ala Gln Pro Tyr Asp Glu Ile Asn Trp Lys Ser Ile Arg
    290                 295                 300

His Leu Cys Ala Lys Glu Asp Leu Tyr Tyr Pro His Pro Phe Leu Gln
305                 310                 315                 320

Asp Leu Met Trp Asp Ser Leu Tyr Ile Cys Thr Glu Pro Leu Leu Asn
                325                 330                 335

Arg Trp Pro Leu Asn Lys Leu Arg Gln Lys Ala Leu Asp Thr Thr Met
            340                 345                 350

Lys His Ile His Tyr Glu Asp Glu Asn Ser Arg Tyr Ile Thr Ile Gly
        355                 360                 365

Ser Val Val Lys Pro Leu Cys Met Leu Ala Cys Trp Val Glu Asp Pro
    370                 375                 380

Asn Gly Val Cys Phe Lys Lys His Ile Ala Arg Ile Pro Asp Tyr Ile
385                 390                 395                 400

Trp Val Ala Glu Asp Gly Met Lys Met Gln Ser Phe Gly Ser Gln Lys
                405                 410                 415

Trp Asp Ala Gly Phe Ala Ile Gln Ala Leu Leu Ala Ala Asp Leu Thr
            420                 425                 430

Glu Glu Asn Gly Ser Thr Leu Met Lys Gly His Glu Phe Ile Lys Ala
        435                 440                 445

Ser Gln Val Lys Asp Asn Pro Ser Gly Asp Phe Lys Ser Met His Arg
    450                 455                 460

His Ile Ser Lys Gly Ser Trp Thr Phe Ser Asp Gln Asp His Gly Trp
465                 470                 475                 480

Gln Ile Ser Asp Cys Thr Ala Glu Gly Leu Lys Cys Cys Leu Leu Phe
                485                 490                 495

Leu Thr Met Pro Ala Glu Ile Val Gly Glu His Met Lys Pro Glu Gln
            500                 505                 510

Phe Asn Asp Ala Val Asn Val Ile Leu Ser Leu Gln Ser Lys Asn Gly
        515                 520                 525

Gly Leu Ala Ala Trp Glu Pro Ala Gly Ser Ser Glu Trp Leu Glu Val
    530                 535                 540

Leu Asn Pro Thr Glu Phe Phe Ala Asp Ile Val Ile Glu His Glu Tyr
545                 550                 555                 560

Val Glu Cys Thr Ser Ser Ala Ser Gln Ala Leu Val Leu Phe Lys Lys
                565                 570                 575

Leu Tyr Pro Gly His Arg Arg Lys Glu Ile Glu Ser Phe Leu Thr Gly
            580                 585                 590
```

```
Ala Ser Gly Tyr Leu Glu Lys Ile Gln Met Glu Asp Gly Ser Trp Tyr
        595                 600                 605

Gly Asn Trp Gly Val Cys Phe Thr Tyr Gly Thr Trp Phe Ala Leu Gly
    610                 615                 620

Gly Leu Thr Ala Val Gly Lys Thr Phe Glu Asn Cys Leu Ala Ile Arg
625                 630                 635                 640

Lys Ala Val Lys Phe Leu Leu Glu Thr Gln Leu Glu Asp Gly Gly Trp
                645                 650                 655

Gly Glu Ser Tyr Lys Ser Cys Pro Glu Lys Arg Tyr Val Pro Leu Glu
            660                 665                 670

Glu Gly Arg Ser Asn Leu Val His Thr Ala Trp Gly Met Met Gly Leu
        675                 680                 685

Ile His Ser Gln Gln Met Glu Arg Asp Pro Met Pro Leu His Lys Ala
    690                 695                 700

Ala Lys Leu Leu Ile Asn Ser Gln Leu Glu Asn Gly Asp Phe Pro Gln
705                 710                 715                 720

Gln Lys Ile Ala Gly Val Phe Lys Met Asn Cys Met Leu His Tyr Ala
                725                 730                 735

Leu Tyr Arg Asn Ile Phe Pro Met Trp Ala Leu Ala Asp Tyr Arg Lys
            740                 745                 750

His Val Leu Lys Gly Ile
        755
```

<210> SEQ ID NO 15
<211> LENGTH: 2277
<212> TYPE: DNA
<213> ORGANISM: Taraxacum koksaghyz

<400> SEQUENCE: 15

```
atgtggaagt tgaagatagc acaaggaaat gatccttatc tattttccac aaacaatttt     60

gttggccggc aaatttggga atttgatccc gatgctggaa cacccgcaga gcgacaagaa    120

gtagaagatg ctcgccagta ttttcgcaat aatcgaaggg agggtgttca tccatgtggt    180

gatttgctta tgcgggcaca gttgatcaaa gagagtggaa ttgatgtatc gagcatacca    240

ccaacaagat tggaagaaaa cgaggaagtc aattatgatg cgctaacaac cgcggttaaa    300

aaagcgctcc gattaaaccg tgcaattcaa gcaaaagacg gtcattggcc tgcagaaaat    360

gctggcccta tgttcttcac tcctccactc cttattgcta tgtacattag tggagccata    420

gatacgcatt taacgaaaga acacaagaca gaaatgatac gttacatcta caaccaccaa    480

aatgaagatg gagggtgggg attttatatc gaggggcaca gcacaatgat tggatctgca    540

ctaagctacg tagccctaag gttactggga gaaggaccga atgatgggaa tggtgcagtg    600

acccaagcaa gagagtggat actgcaacat gggggtgcaa cgtcgattcc ctcttggggc    660

aaaacttatc tctctgtact tggggtatat gaatgggagg gatgtaatcc acttccacca    720

gaattttggc tattccctga atctttaccg tatcatccag caaaaatgtg gtgctattgt    780

cggacaactt atatgcccat gtcatacttg tacgggaaaa aataccatgg tccaatcacc    840

gatcttgttc ttcaacttcg aaaagaaatt catccaattc catatcacaa gattgattgg    900

aataaacagc gccacaactg ttgcaaggat gatttgtact accctcattc aacactacaa    960

gatctattgt gggatggtct taactacttt agcgagccac ttcttaagta ttggcctttt   1020

accaaattaa gagaaaaagg tctcaaaaga gctgttgaac taatgcgata tagcgctgaa   1080

gagagcagat atatcaccat tggatgtgtt gaaaagagtt tgcaaatgat gtgttggtgg   1140
```

```
gcggagaacc caaatgggga tgagtttaag catcaccttg ctagggttcc cgattattta   1200

tggttagcag aagatggaat gaagatgcaa agttttggga gtcaaatatg ggattgcaca   1260

ttagcaactc aagcaataat atctacggat atggtcgaag aatacgggga ttcccttaaa   1320

aaagcccatt tttatataca agaatctcaa attaaagaaa acccatccgg agattttagt   1380

aaaatgtgtc gccagtttac taaaggagcg tggactttct ctgaccaaga tcaaggttgg   1440

gttgtctcgg attgcacagc tgaagcactt aagtgtcttc tgttactatc acaaatgcca   1500

gaagaaatct cgggagaaaa ggcggataat gaaagattat atgaggctgt taatgtcctt   1560

ctctacttac aaagtcctat tagtggaggt tttgctattt gggagccacc tgtcccgcaa   1620

ccatatttac agatgttgaa tccttccgaa attttcgccg acatagttgt ggaaaaagag   1680

catgttgagt gtacgtcgtc aattattcaa gccctttttag ccttcaaacg attgcacccc   1740

ggtcacaggg agaaagaaat cgaaatatcg gtgtcaaaag cagttagttt tttggaggaa   1800

aaacaatggc acgatggttc atggtatggt tattggggaa tatgcttcat atatgggacg   1860

ttttttactc taggagggtt aatttcggct ggaaaaacat ataacaatag tgaagcggtt   1920

cgtagagcgg ttaatttttt cctttcgaca caaaatgaag agggtggatg gggtgagagc   1980

attaagtctt gccctagtga agtgtacaca ccgttggatg aaaataggac aaatttggtt   2040

caaacttcgt gggctatgct tgggcttatg ttaggtggac aggccgaaag agatccaaca   2100

ccattgcata aagcagcaaa gatattaatt aattcacaaa tggataacgg agattttcca   2160

caacaggaga ttactggagt atacatgaag aattgcatgc tacattatgc agagtacaga   2220

aacatttcc cactttgggc acttggggaa tatcgcaaaa gagtttgggt caattaa      2277


<210> SEQ ID NO 16
<211> LENGTH: 758
<212> TYPE: PRT
<213> ORGANISM: Taraxacum koksaghyz

<400> SEQUENCE: 16

Met Trp Lys Leu Lys Ile Ala Gln Gly Asn Asp Pro Tyr Leu Phe Ser
1               5                   10                  15

Thr Asn Asn Phe Val Gly Arg Gln Ile Trp Glu Phe Asp Pro Asp Ala
            20                  25                  30

Gly Thr Pro Ala Glu Arg Gln Glu Val Glu Asp Ala Arg Gln Tyr Phe
        35                  40                  45

Arg Asn Asn Arg Arg Glu Gly Val His Pro Cys Gly Asp Leu Leu Met
    50                  55                  60

Arg Ala Gln Leu Ile Lys Glu Ser Gly Ile Asp Val Ser Ser Ile Pro
65                  70                  75                  80

Pro Thr Arg Leu Glu Glu Asn Glu Glu Val Asn Tyr Asp Ala Leu Thr
                85                  90                  95

Thr Ala Val Lys Lys Ala Leu Arg Leu Asn Arg Ala Ile Gln Ala Lys
            100                 105                 110

Asp Gly His Trp Pro Ala Glu Asn Ala Gly Pro Met Phe Phe Thr Pro
        115                 120                 125

Pro Leu Leu Ile Ala Met Tyr Ile Ser Gly Ala Ile Asp Thr His Leu
    130                 135                 140

Thr Lys Glu His Lys Thr Glu Met Ile Arg Tyr Ile Tyr Asn His Gln
145                 150                 155                 160

Asn Glu Asp Gly Gly Trp Gly Phe Tyr Ile Glu Gly His Ser Thr Met
                165                 170                 175
```

```
Ile Gly Ser Ala Leu Ser Tyr Val Ala Leu Arg Leu Leu Gly Glu Gly
            180                 185                 190

Pro Asn Asp Gly Asn Gly Ala Val Thr Gln Ala Arg Glu Trp Ile Leu
        195                 200                 205

Gln His Gly Gly Ala Thr Ser Ile Pro Ser Trp Gly Lys Thr Tyr Leu
    210                 215                 220

Ser Val Leu Gly Val Tyr Glu Trp Glu Gly Cys Asn Pro Leu Pro Pro
225                 230                 235                 240

Glu Phe Trp Leu Phe Pro Glu Ser Leu Pro Tyr His Pro Ala Lys Met
                245                 250                 255

Trp Cys Tyr Cys Arg Thr Thr Tyr Met Pro Met Ser Tyr Leu Tyr Gly
            260                 265                 270

Lys Lys Tyr His Gly Pro Ile Thr Asp Leu Val Leu Gln Leu Arg Lys
        275                 280                 285

Glu Ile His Pro Ile Pro Tyr His Lys Ile Asp Trp Asn Lys Gln Arg
    290                 295                 300

His Asn Cys Cys Lys Asp Asp Leu Tyr Tyr Pro His Ser Thr Leu Gln
305                 310                 315                 320

Asp Leu Leu Trp Asp Gly Leu Asn Tyr Phe Ser Glu Pro Leu Leu Lys
                325                 330                 335

Tyr Trp Pro Phe Thr Lys Leu Arg Glu Lys Gly Leu Lys Arg Ala Val
            340                 345                 350

Glu Leu Met Arg Tyr Ser Ala Glu Glu Ser Arg Tyr Ile Thr Ile Gly
        355                 360                 365

Cys Val Glu Lys Ser Leu Gln Met Met Cys Trp Trp Ala Glu Asn Pro
    370                 375                 380

Asn Gly Asp Glu Phe Lys His His Leu Ala Arg Val Pro Asp Tyr Leu
385                 390                 395                 400

Trp Leu Ala Glu Asp Gly Met Lys Met Gln Ser Phe Gly Ser Gln Ile
                405                 410                 415

Trp Asp Cys Thr Leu Ala Thr Gln Ala Ile Ile Ser Thr Asp Met Val
            420                 425                 430

Glu Glu Tyr Gly Asp Ser Leu Lys Lys Ala His Phe Tyr Ile Gln Glu
        435                 440                 445

Ser Gln Ile Lys Glu Asn Pro Ser Gly Asp Phe Ser Lys Met Cys Arg
    450                 455                 460

Gln Phe Thr Lys Gly Ala Trp Thr Phe Ser Asp Gln Asp Gln Gly Trp
465                 470                 475                 480

Val Val Ser Asp Cys Thr Ala Glu Ala Leu Lys Cys Leu Leu Leu Leu
                485                 490                 495

Ser Gln Met Pro Glu Glu Ile Ser Gly Glu Lys Ala Asp Asn Glu Arg
            500                 505                 510

Leu Tyr Glu Ala Val Asn Val Leu Leu Tyr Leu Gln Ser Pro Ile Ser
        515                 520                 525

Gly Gly Phe Ala Ile Trp Glu Pro Pro Val Pro Gln Pro Tyr Leu Gln
    530                 535                 540

Met Leu Asn Pro Ser Glu Ile Phe Ala Asp Ile Val Val Glu Lys Glu
545                 550                 555                 560

His Val Glu Cys Thr Ser Ser Ile Ile Gln Ala Leu Leu Ala Phe Lys
                565                 570                 575

Arg Leu His Pro Gly His Arg Glu Lys Glu Ile Glu Ile Ser Val Ser
            580                 585                 590

Lys Ala Val Ser Phe Leu Glu Glu Lys Gln Trp His Asp Gly Ser Trp
```

```
        595                 600                 605

Tyr Gly Tyr Trp Gly Ile Cys Phe Ile Tyr Gly Thr Phe Phe Thr Leu
    610                 615                 620

Gly Gly Leu Ile Ser Ala Gly Lys Thr Tyr Asn Asn Ser Glu Ala Val
625                 630                 635                 640

Arg Arg Ala Val Asn Phe Phe Leu Ser Thr Gln Asn Glu Glu Gly Gly
                645                 650                 655

Trp Gly Glu Ser Ile Lys Ser Cys Pro Ser Glu Val Tyr Thr Pro Leu
            660                 665                 670

Asp Glu Asn Arg Thr Asn Leu Val Gln Thr Ser Trp Ala Met Leu Gly
        675                 680                 685

Leu Met Leu Gly Gly Gln Ala Glu Arg Asp Pro Thr Pro Leu His Lys
    690                 695                 700

Ala Ala Lys Ile Leu Ile Asn Ser Gln Met Asp Asn Gly Asp Phe Pro
705                 710                 715                 720

Gln Gln Glu Ile Thr Gly Val Tyr Met Lys Asn Cys Met Leu His Tyr
                725                 730                 735

Ala Glu Tyr Arg Asn Ile Phe Pro Leu Trp Ala Leu Gly Glu Tyr Arg
            740                 745                 750

Lys Arg Val Trp Val Asn
        755
```

<210> SEQ ID NO 17
<211> LENGTH: 2277
<212> TYPE: DNA
<213> ORGANISM: Taraxacum koksaghyz

<400> SEQUENCE: 17

```
atgtggaagc taaagatagc agaagggaat gatccttact tgtttagcac caacaacttt      60

gttggccgcc aaatttggga gttcgatccc gatgcaggaa cacctgaaga acggcaagaa     120

gtagagaatg ctcgccaaaa ttttcttaat cgacaaaagg aaggttttca gacatgcggc     180

gatttactca tgcggataca gttaatcagg gagaatggaa ttgatttact gagcatacca     240

cctgcgaggt tgggagaaaa agaggatgtg gattatgaag cagtgacgac atcaataaga     300

aaagctgttc gatacagttg tgccattcaa gcaaaagatg gtcattgggc tactgaacat     360

ggtggccctt tgttcttcac tcctccccctt attattatct tatacattag tggagccatt     420

gatacacatt taacaaaaga acacaagaag gagatgaaac gttttatcca caaccatcaa     480

aatgaagatg gaggatgggg attccatatc gaaggacata gcaccatgtt tgtaactgtc     540

ttaagttatg tgtccctacg attgctaggg gaagaaaaac acgacacaaa tgttgcattg     600

attcgtgcca gaaaatggat acttgaccat ggtggtgcga ccaatgtacc atcttggggc     660

aaactttatc tctcggttct tggtgtatat gaatgggaag gatgcaaccc aataccacct     720

gaattttgga ttttccctga gttcttacca tttcatccag caaaaatgtg gtgctattgt     780

cgaacggcct atatgccaat gtcatacttg tacgggagaa aattccaagg cccaatcact     840

gatcttgtgt tacaactgag aaaagagatt tatcttacac catacaacga aataaattgg     900

aatgaacatc gccataaatg ttgcaaggaa gacctctatt accctcatac aatagtccaa     960

gatttgttat gggatggtct ttattacttg agtgagccac tcttcaagtt ttggcctttt    1020

accaaactaa gagaaaaagc cctcaaaaga acacttgagt tgactcgcta taatgctgaa    1080

gaaagcaggt acattaccat ggcaagtatt gaaaagggtt ttcaaatgat gtgttggtgg    1140

gcggcgaacc caaacggaga tgaattcaag catcaccttg ctagactacc agattactta    1200
```

```
tggctagcag aagatggaat gaagtcgcaa acttttggta gtcaattatg gtgtagcgca   1260

tttgcaacac aagcaataat cgcaagtaat atgcccgaag aatatgggga ttctctcaaa   1320

aaggctcatt tctttctcaa agaatctcag gttaaacaaa acccaaaggg agattttact   1380

aaaatgtgtc gacagtttag caaaggatcg tggacgttca ccgatcaaga tcatggttgg   1440

cctgtctcag attgtacagg agaagcattg aaatgcctgc ttttattatc ccaaatgccc   1500

gaagaaattt caggagaaaa agtagataat cagcggctat atgatgctgt taacttcctc   1560

cttcacgtac aaagtcctac aacaggaggt tttgctgttt gggaaaaacc gatccctcat   1620

ccatatttac agacgttaaa tccttcagaa atgttcgccg acattgttgt tgaaagagag   1680

catgttgagt gcacaacttc agtgatgcaa gctctcatcg cattccaaca cttccactcc   1740

gggcacaggg aaaaagaaat agaaaacgct attgcaaatg cagtacgtta tctagaggag   1800

atacaacggg aagatggttc atggtatggc tattggggta tatgtttcat atatggcaca   1860

ttcttttcgt taggaggctt agaatcagct ggaaaaacat ataatgattg tgaagcaatt   1920

cgaaaaggag ccaagttttt actttcgaca caaaatgaag aaggtggatg gggagagagc   1980

tataaatctt gccctagtga agtgtacaca ccgctagatg ggaataaaac taatatagtt   2040

caaacttcat gggctatgct tggtctcatg tcatcggggc aggctgaacg agatccaaca   2100

ccgttacata aagcagcaag gatcttgatt aatgcacaaa tggataatgg agattttccg   2160

caacaggaga tgactggagc tgcgatgagg aattgcatgc tacattatcc gttatatagt   2220

aatatcttcc ccttattggc tctttccaaa tatcgccaac aattttggga taaatga      2277
```

<210> SEQ ID NO 18
<211> LENGTH: 758
<212> TYPE: PRT
<213> ORGANISM: Taraxacum koksaghyz

<400> SEQUENCE: 18

```
Met Trp Lys Leu Lys Ile Ala Glu Gly Asn Asp Pro Tyr Leu Phe Ser
1               5                   10                  15

Thr Asn Asn Phe Val Gly Arg Gln Ile Trp Glu Phe Asp Pro Asp Ala
            20                  25                  30

Gly Thr Pro Glu Glu Arg Gln Glu Val Glu Asn Ala Arg Gln Asn Phe
        35                  40                  45

Leu Asn Arg Gln Lys Glu Gly Phe Gln Thr Cys Gly Asp Leu Leu Met
    50                  55                  60

Arg Ile Gln Leu Ile Arg Glu Asn Gly Ile Asp Leu Leu Ser Ile Pro
65                  70                  75                  80

Pro Ala Arg Leu Gly Glu Lys Glu Asp Val Asp Tyr Glu Ala Val Thr
                85                  90                  95

Thr Ser Ile Arg Lys Ala Val Arg Tyr Ser Cys Ala Ile Gln Ala Lys
            100                 105                 110

Asp Gly His Trp Ala Thr Glu His Gly Gly Pro Leu Phe Phe Thr Pro
        115                 120                 125

Pro Leu Ile Ile Ile Leu Tyr Ile Ser Gly Ala Ile Asp Thr His Leu
    130                 135                 140

Thr Lys Glu His Lys Lys Glu Met Lys Arg Phe Ile His Asn His Gln
145                 150                 155                 160

Asn Glu Asp Gly Gly Trp Gly Phe His Ile Glu Gly His Ser Thr Met
                165                 170                 175

Phe Val Thr Val Leu Ser Tyr Val Ser Leu Arg Leu Leu Gly Glu Glu
```

```
            180                 185                 190

Lys His Asp Thr Asn Val Ala Leu Ile Arg Ala Arg Lys Trp Ile Leu
        195                 200                 205

Asp His Gly Gly Ala Thr Asn Val Pro Ser Trp Gly Lys Leu Tyr Leu
    210                 215                 220

Ser Val Leu Gly Val Tyr Glu Trp Glu Gly Cys Asn Pro Ile Pro Pro
225                 230                 235                 240

Glu Phe Trp Ile Phe Pro Glu Phe Leu Pro Phe His Pro Ala Lys Met
                245                 250                 255

Trp Cys Tyr Cys Arg Thr Ala Tyr Met Pro Met Ser Tyr Leu Tyr Gly
            260                 265                 270

Arg Lys Phe Gln Gly Pro Ile Thr Asp Leu Val Leu Gln Leu Arg Lys
        275                 280                 285

Glu Ile Tyr Leu Thr Pro Tyr Asn Glu Ile Asn Trp Asn Glu His Arg
    290                 295                 300

His Lys Cys Cys Lys Glu Asp Leu Tyr Tyr Pro His Thr Ile Val Gln
305                 310                 315                 320

Asp Leu Leu Trp Asp Gly Leu Tyr Tyr Leu Ser Glu Pro Leu Phe Lys
                325                 330                 335

Phe Trp Pro Phe Thr Lys Leu Arg Glu Lys Ala Leu Lys Arg Thr Leu
            340                 345                 350

Glu Leu Thr Arg Tyr Asn Ala Glu Glu Ser Arg Tyr Ile Thr Met Ala
        355                 360                 365

Ser Ile Glu Lys Gly Phe Gln Met Met Cys Trp Trp Ala Ala Asn Pro
    370                 375                 380

Asn Gly Asp Glu Phe Lys His His Leu Ala Arg Leu Pro Asp Tyr Leu
385                 390                 395                 400

Trp Leu Ala Glu Asp Gly Met Lys Ser Gln Thr Phe Gly Ser Gln Leu
                405                 410                 415

Trp Cys Ser Ala Phe Ala Thr Gln Ala Ile Ile Ala Ser Asn Met Pro
            420                 425                 430

Glu Glu Tyr Gly Asp Ser Leu Lys Lys Ala His Phe Phe Leu Lys Glu
        435                 440                 445

Ser Gln Val Lys Gln Asn Pro Lys Gly Asp Phe Thr Lys Met Cys Arg
    450                 455                 460

Gln Phe Ser Lys Gly Ser Trp Thr Phe Thr Asp Gln Asp His Gly Trp
465                 470                 475                 480

Pro Val Ser Asp Cys Thr Gly Glu Ala Leu Lys Cys Leu Leu Leu Leu
                485                 490                 495

Ser Gln Met Pro Glu Glu Ile Ser Gly Glu Lys Val Asp Asn Gln Arg
            500                 505                 510

Leu Tyr Asp Ala Val Asn Phe Leu Leu His Val Gln Ser Pro Thr Thr
        515                 520                 525

Gly Gly Phe Ala Val Trp Glu Lys Pro Ile Pro His Pro Tyr Leu Gln
    530                 535                 540

Thr Leu Asn Pro Ser Glu Met Phe Ala Asp Ile Val Val Glu Arg Glu
545                 550                 555                 560

His Val Glu Cys Thr Thr Ser Val Met Gln Ala Leu Ile Ala Phe Gln
                565                 570                 575

His Phe His Ser Gly His Arg Glu Lys Glu Ile Glu Asn Ala Ile Ala
            580                 585                 590

Asn Ala Val Arg Tyr Leu Glu Glu Ile Gln Arg Glu Asp Gly Ser Trp
        595                 600                 605
```

```
Tyr Gly Tyr Trp Gly Ile Cys Phe Ile Tyr Gly Thr Phe Phe Ser Leu
    610                 615                 620

Gly Gly Leu Glu Ser Ala Gly Lys Thr Tyr Asn Asp Cys Glu Ala Ile
625                 630                 635                 640

Arg Lys Gly Ala Lys Phe Leu Leu Ser Thr Gln Asn Glu Glu Gly Gly
                645                 650                 655

Trp Gly Glu Ser Tyr Lys Ser Cys Pro Ser Glu Val Tyr Thr Pro Leu
            660                 665                 670

Asp Gly Asn Lys Thr Asn Ile Val Gln Thr Ser Trp Ala Met Leu Gly
        675                 680                 685

Leu Met Ser Ser Gly Gln Ala Glu Arg Asp Pro Thr Pro Leu His Lys
    690                 695                 700

Ala Ala Arg Ile Leu Ile Asn Ala Gln Met Asp Asn Gly Asp Phe Pro
705                 710                 715                 720

Gln Gln Glu Met Thr Gly Ala Ala Met Arg Asn Cys Met Leu His Tyr
                725                 730                 735

Pro Leu Tyr Ser Asn Ile Phe Pro Leu Leu Ala Leu Ser Lys Tyr Arg
            740                 745                 750

Gln Gln Phe Trp Asp Lys
        755
```

<210> SEQ ID NO 19
<211> LENGTH: 2277
<212> TYPE: DNA
<213> ORGANISM: Taraxacum koksaghyz

<400> SEQUENCE: 19

```
atgtggaagc tgaaaatagc agaaggtagt gatgatgagt ggctgaccac caccaacaac     60

cacgtcggcc gtcagcactg gcagtttgat ccggatgctg gaaccgaaga ggaacgtgct    120

cagattgaaa agattcgtct caacttcaaa cttaatcgtt ttcaattcaa acaaagtgcc    180

gacttgttaa tgcgtactca actaagaaaa gagaacccaa tcaataaaat accggatgca    240

ataaaattga atgaaacaga agaagtgaca aatgacgcag tgtcaactac actcaaaaga    300

gccattagct tttactccac cattcaagcc catgatgggc actggccagc tgagtctgct    360

ggcccctttgt tcttccttcc tccattggta atagcactat atgtgactgg agcaatgaat    420

gatattctaa cacccgcaca tcagctagaa ataaaacgtt acatatacaa tcatcagaat    480

gaagatggag gttggggatt acatatagag ggtcatagca caatatttgg atcagtactt    540

agttacataa ctttaagatt acttggggaa gaagctgata gtgttgcaga ggacatggct    600

ttggttaagg ggcgtaaatg gatccttgac catggtggtg cagttgggat tccttcgtgg    660

ggaaagtttt ggcttacgat acttggagta tacgaatggg gaggctgtaa tcctatgcca    720

cccgaatttt ggctcatgcc taagtttttc ccaattcatc caggcaaaat gttgtgttat    780

tgtcgcttag tttacatgcc catgtcgtac ttatacggca aagatttgt gggaaaaata    840

accgagttgg ttcgcgacct aaggcaagag ctttatacag acccttatga tgagattaat    900

tggaataaag cacgaaacac gtgtgcaaag gaagatctct actatccaca cccttttgtt    960

caagatatgg tatggggtgt acttcataat gtttttgaac ctgtattaac aagtcgtccg   1020

ctttccacac taagagaaaa ggctttgaaa gtcgcaatgg atcatgttca ctatgaagat   1080

aagagtagta gatatctttg cattggatgt gtggaaaagg tgttatgctt gattgcaacg   1140

tgggtggaag atccaaatgg tgatgcatat aaacgtcatc ttgctagaat tcctgactac   1200
```

```
ttttgggttg ctgaagatgg gatgaaaatg cagagttttg gatgtcaaat gtgggatgcg   1260

gcctttgcta ttcaagctat tttatctagt aatctagccg aagaatacgg cccgactctt   1320

aaaaaagcac acgagtttgt aaaagcatca caggttcgtg ataatccgcc gggagatttc   1380

agtaaaatgt acagacacac ttctaagggt gcatggacat tttccataca agatcatggt   1440

tggcaagtct ctgattgtac ggctgaaggc ttgaaggttg cacttttgta ctcccaaatg   1500

agcccagaac ttgtgggcga aaaacttgaa actgagcatc tctacgatgc tgtcaatgtc   1560

attctttcat tacaaagtga aaacggtggc tttcctgctt gggaaccaca aagggcgtat   1620

gcttggttgg agaaattcaa cccgactgaa ttctttgaag atgtgttgat cgaacgagag   1680

tatgttgaat gcacttcatc tgcaatccaa ggtttgacac tcttcaagaa gttgcaccca   1740

gggcacagaa ccaaggagat cgagcattgt atatcaagag ctataaagta cgtcgaagac   1800

acacaagaaa gtgatggttc atggtatggt tgttggggaa tttgctacac ctatggtaca   1860

tggtttgcgg tagatgcgct agtagcttgt ggtaagaact atcataactc tcccgccctt   1920

caaaaagcat gcaaatttct gttatccaaa caacttccgg atggtggatg gggagaaagt   1980

tatctttcga gctcaaataa ggtgtatacg aatttggagg gaaatcgttc gaatttagtg   2040

catacatcat gggctttaat atcacttatt aaagcgggac aggctgaaat tgatcctaca   2100

ccaatatcta atggcgtacg gcttctcatc aattcacaaa tggaagaagg ggactttcct   2160

caacaggaaa tcacaggagt gttcatgaag aactgtaacc tcaattactc atcatatcga   2220

aatatttttc ccatatgggc acttggtgaa tatcgtcgta ttgttcaaaa tatatga      2277
```

<210> SEQ ID NO 20
<211> LENGTH: 758
<212> TYPE: PRT
<213> ORGANISM: Taraxacum koksaghyz

<400> SEQUENCE: 20

```
Met Trp Lys Leu Lys Ile Ala Glu Gly Ser Asp Asp Glu Trp Leu Thr
1               5                   10                  15

Thr Thr Asn Asn His Val Gly Arg Gln His Trp Gln Phe Asp Pro Asp
            20                  25                  30

Ala Gly Thr Glu Glu Glu Arg Ala Gln Ile Glu Lys Ile Arg Leu Asn
        35                  40                  45

Phe Lys Leu Asn Arg Phe Gln Phe Lys Gln Ser Ala Asp Leu Leu Met
    50                  55                  60

Arg Thr Gln Leu Arg Lys Glu Asn Pro Ile Asn Lys Ile Pro Asp Ala
65                  70                  75                  80

Ile Lys Leu Asn Glu Thr Glu Glu Val Thr Asn Asp Ala Val Ser Thr
                85                  90                  95

Thr Leu Lys Arg Ala Ile Ser Phe Tyr Ser Thr Ile Gln Ala His Asp
            100                 105                 110

Gly His Trp Pro Ala Glu Ser Ala Gly Pro Leu Phe Phe Leu Pro Pro
        115                 120                 125

Leu Val Ile Ala Leu Tyr Val Thr Gly Ala Met Asn Asp Ile Leu Thr
    130                 135                 140

Pro Ala His Gln Leu Glu Ile Lys Arg Tyr Ile Tyr Asn His Gln Asn
145                 150                 155                 160

Glu Asp Gly Gly Trp Gly Leu His Ile Glu Gly His Ser Thr Ile Phe
                165                 170                 175

Gly Ser Val Leu Ser Tyr Ile Thr Leu Arg Leu Leu Gly Glu Glu Ala
            180                 185                 190
```

```
Asp Ser Val Ala Glu Asp Met Ala Leu Val Lys Gly Arg Lys Trp Ile
        195                 200                 205

Leu Asp His Gly Gly Ala Val Gly Ile Pro Ser Trp Gly Lys Phe Trp
    210                 215                 220

Leu Thr Ile Leu Gly Val Tyr Glu Trp Gly Gly Cys Asn Pro Met Pro
225                 230                 235                 240

Pro Glu Phe Trp Leu Met Pro Lys Phe Phe Pro Ile His Pro Gly Lys
                245                 250                 255

Met Leu Cys Tyr Cys Arg Leu Val Tyr Met Pro Met Ser Tyr Leu Tyr
            260                 265                 270

Gly Lys Arg Phe Val Gly Lys Ile Thr Glu Leu Val Arg Asp Leu Arg
        275                 280                 285

Gln Glu Leu Tyr Thr Asp Pro Tyr Asp Glu Ile Asn Trp Asn Lys Ala
    290                 295                 300

Arg Asn Thr Cys Ala Lys Glu Asp Leu Tyr Tyr Pro His Pro Phe Val
305                 310                 315                 320

Gln Asp Met Val Trp Gly Val Leu His Asn Val Phe Glu Pro Val Leu
                325                 330                 335

Thr Ser Arg Pro Leu Ser Thr Leu Arg Glu Lys Ala Leu Lys Val Ala
            340                 345                 350

Met Asp His Val His Tyr Glu Asp Lys Ser Ser Arg Tyr Leu Cys Ile
        355                 360                 365

Gly Cys Val Glu Lys Val Leu Cys Leu Ile Ala Thr Trp Val Glu Asp
    370                 375                 380

Pro Asn Gly Asp Ala Tyr Lys Arg His Leu Ala Arg Ile Pro Asp Tyr
385                 390                 395                 400

Phe Trp Val Ala Glu Asp Gly Met Lys Met Gln Ser Phe Gly Cys Gln
                405                 410                 415

Met Trp Asp Ala Ala Phe Ala Ile Gln Ala Ile Leu Ser Ser Asn Leu
            420                 425                 430

Ala Glu Glu Tyr Gly Pro Thr Leu Lys Lys Ala His Glu Phe Val Lys
        435                 440                 445

Ala Ser Gln Val Arg Asp Asn Pro Pro Gly Asp Phe Ser Lys Met Tyr
    450                 455                 460

Arg His Thr Ser Lys Gly Ala Trp Thr Phe Ser Ile Gln Asp His Gly
465                 470                 475                 480

Trp Gln Val Ser Asp Cys Thr Ala Glu Gly Leu Lys Val Ala Leu Leu
                485                 490                 495

Tyr Ser Gln Met Ser Pro Glu Leu Val Gly Glu Lys Leu Glu Thr Glu
            500                 505                 510

His Leu Tyr Asp Ala Val Asn Val Ile Leu Ser Leu Gln Ser Glu Asn
        515                 520                 525

Gly Gly Phe Pro Ala Trp Glu Pro Gln Arg Ala Tyr Ala Trp Leu Glu
    530                 535                 540

Lys Phe Asn Pro Thr Glu Phe Phe Glu Asp Val Leu Ile Glu Arg Glu
545                 550                 555                 560

Tyr Val Glu Cys Thr Ser Ser Ala Ile Gln Gly Leu Thr Leu Phe Lys
                565                 570                 575

Lys Leu His Pro Gly His Arg Thr Lys Glu Ile Glu His Cys Ile Ser
            580                 585                 590

Arg Ala Ile Lys Tyr Val Glu Asp Thr Gln Glu Ser Asp Gly Ser Trp
        595                 600                 605
```

```
Tyr Gly Cys Trp Gly Ile Cys Tyr Thr Tyr Gly Thr Trp Phe Ala Val
    610                 615                 620

Asp Ala Leu Val Ala Cys Gly Lys Asn Tyr His Asn Ser Pro Ala Leu
625                 630                 635                 640

Gln Lys Ala Cys Lys Phe Leu Leu Ser Lys Gln Leu Pro Asp Gly Gly
                645                 650                 655

Trp Gly Glu Ser Tyr Leu Ser Ser Ser Asn Lys Val Tyr Thr Asn Leu
            660                 665                 670

Glu Gly Asn Arg Ser Asn Leu Val His Thr Ser Trp Ala Leu Ile Ser
        675                 680                 685

Leu Ile Lys Ala Gly Gln Ala Glu Ile Asp Pro Thr Pro Ile Ser Asn
    690                 695                 700

Gly Val Arg Leu Leu Ile Asn Ser Gln Met Glu Glu Gly Asp Phe Pro
705                 710                 715                 720

Gln Gln Glu Ile Thr Gly Val Phe Met Lys Asn Cys Asn Leu Asn Tyr
                725                 730                 735

Ser Ser Tyr Arg Asn Ile Phe Pro Ile Trp Ala Leu Gly Glu Tyr Arg
            740                 745                 750

Arg Ile Val Gln Asn Ile
        755


<210> SEQ ID NO 21
<211> LENGTH: 30
<212> TYPE: DNA
<213> ORGANISM: Artificial
<220> FEATURE:
<223> OTHER INFORMATION: TkOSC1-RNAi-fwd-NcoI

<400> SEQUENCE: 21

aaaccatggg cggaattgat cttataagcg                                        30


<210> SEQ ID NO 22
<211> LENGTH: 29
<212> TYPE: DNA
<213> ORGANISM: Artificial
<220> FEATURE:
<223> OTHER INFORMATION: TkOSC1-RNAi-rev-XhoI

<400> SEQUENCE: 22

aaactcgaga tcccaagctt gaatcgcac                                         29


<210> SEQ ID NO 23
<211> LENGTH: 29
<212> TYPE: DNA
<213> ORGANISM: Artificial
<220> FEATURE:
<223> OTHER INFORMATION: TkOSC-RNAi-fwd-NcoI

<400> SEQUENCE: 23

aaaccatgga acaagaaaat ggttcttgg                                         29


<210> SEQ ID NO 24
<211> LENGTH: 29
<212> TYPE: DNA
<213> ORGANISM: Artificial
<220> FEATURE:
<223> OTHER INFORMATION: TkOSC-RNAi-rev-XhoI

<400> SEQUENCE: 24

aaactcgagt ctccaagcgc ccatagcgg                                         29
```

<210> SEQ ID NO 25
<211> LENGTH: 21
<212> TYPE: DNA
<213> ORGANISM: Artificial
<220> FEATURE:
<223> OTHER INFORMATION: TkEF1alpha-fw-realtime

<400> SEQUENCE: 25
cgagagattc gagaaggaag c 21

<210> SEQ ID NO 26
<211> LENGTH: 21
<212> TYPE: DNA
<213> ORGANISM: Artificial
<220> FEATURE:
<223> OTHER INFORMATION: TkEF1alpha-rv-realtime

<400> SEQUENCE: 26
ctgtgcagta gtacttggtg g 21

<210> SEQ ID NO 27
<211> LENGTH: 22
<212> TYPE: DNA
<213> ORGANISM: Artificial
<220> FEATURE:
<223> OTHER INFORMATION: TkLUP-fw-realtime

<400> SEQUENCE: 27
gctgaccacc accaacaacc ac 22

<210> SEQ ID NO 28
<211> LENGTH: 23
<212> TYPE: DNA
<213> ORGANISM: Artificial
<220> FEATURE:
<223> OTHER INFORMATION: TkLUP-rv-realtime

<400> SEQUENCE: 28
agcacgttcc tcttcggttc cag 23

<210> SEQ ID NO 29
<211> LENGTH: 22
<212> TYPE: DNA
<213> ORGANISM: Artificial
<220> FEATURE:
<223> OTHER INFORMATION: TkOSC1-fw-realtime

<400> SEQUENCE: 29
actcctccct tgataattgc cc 22

<210> SEQ ID NO 30
<211> LENGTH: 26
<212> TYPE: DNA
<213> ORGANISM: Artificial
<220> FEATURE:
<223> OTHER INFORMATION: TkOSC1-rv-realtime

<400> SEQUENCE: 30
ttgtgcttct gcctgatata tagaac 26

<210> SEQ ID NO 31
<211> LENGTH: 20
<212> TYPE: DNA
<213> ORGANISM: Artificial
<220> FEATURE:
<223> OTHER INFORMATION: TkOSC2-fw-realtime

<400> SEQUENCE: 31
ccggtgagaa ggtggaagtt 20

<210> SEQ ID NO 32
<211> LENGTH: 20
<212> TYPE: DNA
<213> ORGANISM: Artificial
<220> FEATURE:
<223> OTHER INFORMATION: TkOSC2-rv-realtime

<400> SEQUENCE: 32
ggaaccggta cctcccaaac 20

<210> SEQ ID NO 33
<211> LENGTH: 21
<212> TYPE: DNA
<213> ORGANISM: Artificial
<220> FEATURE:
<223> OTHER INFORMATION: TkOSC3-fw-realtime

<400> SEQUENCE: 33
tccatccaaa ccacagaaaa g 21

<210> SEQ ID NO 34
<211> LENGTH: 22
<212> TYPE: DNA
<213> ORGANISM: Artificial
<220> FEATURE:
<223> OTHER INFORMATION: TkOSC3-rv-realtime

<400> SEQUENCE: 34
atgaagcata ctccccaata ac 22

<210> SEQ ID NO 35
<211> LENGTH: 22
<212> TYPE: DNA
<213> ORGANISM: Artificial
<220> FEATURE:
<223> OTHER INFORMATION: TkOSC4-fw-realtime

<400> SEQUENCE: 35
ccgacaattc gtaaggccac tg 22

<210> SEQ ID NO 36
<211> LENGTH: 20
<212> TYPE: DNA
<213> ORGANISM: Artificial
<220> FEATURE:
<223> OTHER INFORMATION: TkOSC4-rv-realtime

<400> SEQUENCE: 36
tgtttgcacc acgttcgacc 20

<210> SEQ ID NO 37
<211> LENGTH: 24
<212> TYPE: DNA
<213> ORGANISM: Artificial
<220> FEATURE:
<223> OTHER INFORMATION: TkOSC5-fw-realtime

<400> SEQUENCE: 37
gaaacacaac tagaagatgg cggt 24

<210> SEQ ID NO 38
<211> LENGTH: 22

<212> TYPE: DNA
<213> ORGANISM: Artificial
<220> FEATURE:
<223> OTHER INFORMATION: TkOSC5-rv-realtime

<400> SEQUENCE: 38
catagcccat gaagtgtgca ct 22

<210> SEQ ID NO 39
<211> LENGTH: 21
<212> TYPE: DNA
<213> ORGANISM: Artificial
<220> FEATURE:
<223> OTHER INFORMATION: TkOSC6-fw-realtime

<400> SEQUENCE: 39
ggtcatagca ccatgtttgg g 21

<210> SEQ ID NO 40
<211> LENGTH: 22
<212> TYPE: DNA
<213> ORGANISM: Artificial
<220> FEATURE:
<223> OTHER INFORMATION: TkOSC6-rv-realtime

<400> SEQUENCE: 40
ggtgactgag ccatgatcca gg 22

<210> SEQ ID NO 41
<211> LENGTH: 18
<212> TYPE: DNA
<213> ORGANISM: Artificial
<220> FEATURE:
<223> OTHER INFORMATION: TkOSC7-fw-realtime

<400> SEQUENCE: 41
cgatgctgga acacccgc 18

<210> SEQ ID NO 42
<211> LENGTH: 23
<212> TYPE: DNA
<213> ORGANISM: Artificial
<220> FEATURE:
<223> OTHER INFORMATION: TkOSC7-rv-realtime

<400> SEQUENCE: 42
gttggtggta tgctcgatac atc 23

<210> SEQ ID NO 43
<211> LENGTH: 20
<212> TYPE: DNA
<213> ORGANISM: Artificial
<220> FEATURE:
<223> OTHER INFORMATION: TkOSC8-fw-realtime

<400> SEQUENCE: 43
ctgagcatac cacctgcgag 20

<210> SEQ ID NO 44
<211> LENGTH: 27
<212> TYPE: DNA
<213> ORGANISM: Artificial
<220> FEATURE:
<223> OTHER INFORMATION: TkOSC8-rv-realtime

<400> SEQUENCE: 44
cagcttttct tattgatgtc gtcactg 27

<210> SEQ ID NO 45
<211> LENGTH: 22
<212> TYPE: DNA
<213> ORGANISM: Artificial
<220> FEATURE:
<223> OTHER INFORMATION: TkRP-fw-realtime

<400> SEQUENCE: 45
cgtcgatctc aaggatgttg tc 22

<210> SEQ ID NO 46
<211> LENGTH: 22
<212> TYPE: DNA
<213> ORGANISM: Artificial
<220> FEATURE:
<223> OTHER INFORMATION: TkRP-rv-realtime

<400> SEQUENCE: 46
ggagctttga gaagaaccaa cg 22

<210> SEQ ID NO 47
<211> LENGTH: 445
<212> TYPE: DNA
<213> ORGANISM: Artificial
<220> FEATURE:
<223> OTHER INFORMATION: Sense sequence in TkOSC hpRNAi construct

<400> SEQUENCE: 47
aacaagaaaa tggttcttgg tatggttatt ggggtatatg ttatctttat ggaacctatt 60
tcgtgttaca aggattggta gcttgtggac aaacatatga aaatagtgaa gcagttcgga 120
aagctgtcaa gtttttcctc tcgacacaaa actcagaagg tggttgggga gagaactttg 180
agtcatgccc acaagagaaa tttatacctt tggaagggaa cagaacaaat tttgtgcaaa 240
cttcatgggc catgcttggt cttctatgtg gtggacaggc tgaaagagat ccgacaccat 300
tacacaaggc agcaaaattg ctcataaatg gacaaatgga taatggagac tttcctcaac 360
aggaaataac aggagtgtac atgaagaatt gcatgttaca ttatgcagaa tataggaaca 420
cttttccgct atgggcgctt ggaga 445

<210> SEQ ID NO 48
<211> LENGTH: 125
<212> TYPE: DNA
<213> ORGANISM: Artificial
<220> FEATURE:
<223> OTHER INFORMATION: Sense sequence in TkOSC1 hpRNAi construct

<400> SEQUENCE: 48
gcggaattga tcttataagc gtacctccag tgagacttgg agacgacgaa gatgtgaact 60
atgaagcggt gacaacagcc gtgagaaagg cagttagact gaaccgtgcg attcaagctt 120
gggat 125

<210> SEQ ID NO 49
<211> LENGTH: 5889
<212> TYPE: DNA
<213> ORGANISM: Artificial
<220> FEATURE:
<223> OTHER INFORMATION: TkOSC-RNAi expression vector
<220> FEATURE:
<221> NAME/KEY: misc_feature
<222> LOCATION: (3361)..(3361)
<223> OTHER INFORMATION: n is a, c, g, or t
<220> FEATURE:
<221> NAME/KEY: misc_feature
<222> LOCATION: (3574)..(3574)
<223> OTHER INFORMATION: n is a, c, g, or t

<400> SEQUENCE: 49

```
tggcaggata tattgtggtg taaacaaatt gacgcttaga caacttaata acacattgcg     60
gacgttttta atgtactgaa ttaacgccga attaattcga gctcggatct gataatttat    120
ttgaaaattc ataagaaaag caaacgttac atgaattgat gaaacaatac aaagacagat    180
aaagccacgc acatttagga tattggccga gattactgaa tattgagtaa gatcacggaa    240
tttctgacag gagcatgtct tcaattcagc ccaaatggca gttgaaatac tcaaaccgcc    300
ccatatgcag gagcggatca ttcattgttt gtttggttgc ctttgccaac atgggagtcc    360
aagattctgc agtcaaatct cggtgacggg caggaccgga cggggcggta ccggcaggct    420
gaagtccagc tgccagaaac ccacgtcatg ccagttcccg tgcttgaagc cggccgcccg    480
cagcatgccg cggggggcat atccgagcgc ctcgtgcatg cgcacgctcg ggtcgttggg    540
cagcccgatg acagcgacca cgctcttgaa gccctgtgcc tccagggact tcagcaggtg    600
ggtgtagagc gtggagccca gtcccgtccg ctggtggcgg ggggagacgt acacggtcga    660
ctcggccgtc cagtcgtagg cgttgcgtgc cttccagggg cccgcgtagg cgatgccggc    720
gacctcgccg tccacctcgg cgacgagcca gggatagcgc tcccgcagac ggacgaggtc    780
gtccgtccac tcctgcggtt cctgcggctc ggtacggaag ttgaccgtgc ttgtctcgat    840
gtagtggttg acgatggtgc agaccgccgg catgtccgcc tcggtggcac ggcggatgtc    900
ggccgggcgt cgttctgggc tcatcgattc gatttggtgt atcgagattg gttatgaaat    960
tcagatgcta gtgtaatgta ttggtaattt gggaagatat aataggaagc aaggctattt   1020
atccatttct gaaaaggcga aatggcgtca ccgcgagcgt cacgcgcatt ccgttcttgc   1080
tgtaaagcgt tgtttggtac acttttgact agcgaggctt ggcgtgtcag cgtatctatt   1140
caaaagtcgt taatggctgc ggatcaagaa aaagttggaa tagaaacaga atacccgcga   1200
aattcaggcc cggttgccat gtcctacacg ccgaaataaa cgaccaaatt agtagaaaaa   1260
taaaaactga ctcggatact tacgtcacgt cttgcgcact gatttgaaaa atctcagaat   1320
taagcttccc gggattgttt catgcgcacg gaaacgttaa gagcttcgga ttatcatttt   1380
gataaagaaa ttaataaaag ataacgaaat aaatttaact ttaaaatttt gaaaatttat   1440
caggattctt atgaaagaaa ctgtatcagg attcttagga caaaaactag ctagttctct   1500
tttaaaatgt aaaacttatt ttttatgaaa gtattgaaca tcaaaaacta gtaggctaac   1560
atcatatgtg atttctgcat ggaacatctt atacacatgc agcatctcat tcacatgtaa   1620
ttgaactcgt cacgaaagtc attaaagtca ttaaactaac aatcaagata aactaaaaag   1680
ttatttaaat ttctttaaaa aaaatttgga acgacaacta ttgtaactta atcttaattt   1740
tacacatctc ggttcaaaca tgaaataaat attctaccca aacaataaat ggtaacttaa   1800
tttagtttct tttaatttgt tgattgctta taatctctta gataatataa atacgtcaaa   1860
tcagaagttg tggtatccac aaaaacgtgt tttaatgaat tcactaggtt aaaatcccgt   1920
gtaatacacg ggttaaaaat tttaaataca tataaataat ataattttat gtttgataat   1980
tcttaatatt tataacataa catgaacaat tttagaatat attaagattt aaaataagat   2040
aatagtaatt aatagttacc ataacaataa ttgaaaaata ttgtcaaaaa ttaggaaatt   2100
tcaattttga ttaaatgggc gggaaaataa aattgcgaaa gattatggtg ataacacgtg   2160
```

-continued

```
tcctatacgt attcttttat cagtagtaga ttatatgcaa gaaatgctaa atgacaaaaa   2220
cataaaagag tactatatat cgtagccaag cgatattcaa tatcattcaa ttttgaccta   2280
caattcatat atagacatat ctttgcgagc ccgttcacgt agtttctgga acctcgagta   2340
taagagctca tttttacaac aattaccaac aacaacaaac aacaaacaac attacaatta   2400
catttacaat tatccatgat caccactttg tacaagaaag ctgggtctag atatctcgag   2460
tctccaagcg cccatagcgg aaaagtgttc ctatattctg cataatgtaa catgcaattc   2520
ttcatgtaca ctcctgttat ttcctgttga ggaaagtctc cattatccat ttgtccattt   2580
atgagcaatt ttgctgcctt gtgtaatggt gtcggatctc tttcagcctg tccaccacat   2640
agaagaccaa gcatggccca tgaagtttgc acaaaatttg ttctgttccc ttccaaaggt   2700
ataaatttct cttgtgggca tgactcaaag ttctctcccc aaccaccttc tgagttttgt   2760
gtcgagagga aaaacttgac agctttccga actgcttcac tattttcata tgtttgtcca   2820
caagctacca atccttgtaa cacgaaatag gttccataaa gataacatat accccaataa   2880
ccataccaag aaccattttc ttgttccatg gtggagcctg ctttttttgta caaacttgtg   2940
atcatggggc gcgcccaatc gatgatttaa atgtgtaaga atttcttatg ttacattatt   3000
acattcaacg ttttatctta attggctctt catttgattg aaatttgaca attatttctt   3060
gtttttttt ttgtcacact ctttttgggt tggggtggcc gacgaattgt gggaaggtag   3120
aaagagggga ggacttttgt tatactccat tagtaattac tgtttccgtt tcaatttatg   3180
tgacaatatt tcctttttag tcggttccaa aagaaaatgt cagcattata aacaatttaa   3240
ttttgaaatt acaattttgc cattaataaa atgatttaca accacaaaag tatctatgag   3300
cctgtttggg tgggcttata agcagcttat tttaagtggc ttataagtca aaaagtgaca   3360
ntttttgaga agttagaaaa tcctaacttc tcaaaaagta gcttttaagc cacttatgac   3420
ttataagtcc aaaaatttt aagttaccaa acatatatta atgggtttat aagcttataa   3480
gccactttta agctcaccca aacgggttct atgtctcact ttagactaca aattttaaaa   3540
gtcttcattt atttcttaat ctccgtggcg agtnaaacta taacacataa agtgaaacgg   3600
agggaataag atggagtcat aaactaatcc aaatctatac tctctccgtt aatttgtttt   3660
ttagtttgat ttggtacatt aataaaacag atttttcgaa ggttataaac acagacagat   3720
gtttcccagc gagctagcaa aattccaaga tttctgtcga aaattcgtgt gtttctagct   3780
agtacttgat gttatcttta accttttagt aattttttgt ccttttcttt ctatttttca   3840
tcttacaatg aattatgagc aagttcctta agtagcatca cacgtgagat gttttttatg   3900
atattgacta aatccaatct ttaccattcc ttaactagta aaatacaaca catgttaatt   3960
gatacattgc ttaacactga ggttagaaaa ttttagaaat tagttgtcca aatgctttga   4020
aattagaaat ctttaatccc ttattttttt ttaaaatgtt ttttctcact ccaaagaaag   4080
agaaactgac atgaaagctc aaaagatcat gaatcttact aactttgtgg aactaaatgt   4140
acatcagaat gtttctgaca tgtgaaaatg aaagctctta attttcttct tttatttatt   4200
gagggttttt gcatgctatg cattcaattt gagtacttta aagcacctat aaacacttac   4260
ttacacttgc cttggagttt atgttttagt gttttcttca catctttttt ggtcaatttg   4320
caggtattgg atcctaggtg agtctagtca aacaagtttg tacaaaaaag caggctccac   4380
catggaacaa gaaaatggtt cttggtatgg ttattggggt atatgttatc tttatggaac   4440
ctatttcgtg ttacaaggat tggtagcttg tggacaaaca tatgaaaata gtgaagcagt   4500
tcggaaagct gtcaagtttt tcctctcgac acaaaactca gaaggtggtt ggggagagaa   4560
```

ctttgagtca tgcccacaag agaaatttat acctttggaa gggaacagaa caaattttgt 4620
gcaaacttca tgggccatgc ttggtcttct atgtggtgga caggctgaaa gagatccgac 4680
accattacac aaggcagcaa aattgctcat aaatggacaa atggataatg gagactttcc 4740
tcaacaggaa ataacaggag tgtacatgaa gaattgcatg ttacattatg cagaatatag 4800
gaacactttt ccgctatggg cgcttggaga ctcgagatat ctagacccag ctttcttgta 4860
caaagtggtt cgactagaga gttaattaag acccgggact agtccctaga gtcctgtctt 4920
taatgagata tgcgagacgc ctatgatcgc atgatatttg ctttcaattc tgttgtgcac 4980
gttgtaaaaa acctgagcat gtgtagctca gatccttacc gccggtttcg gttcattcta 5040
atgaatatat cacccgttac tatcgtattt ttatgaataa tattctccgt tcaatttact 5100
gattgtaccc tactacttat atgtacaata ttaaaatgaa aacaatatat tgtgctgaat 5160
aggtttatag cgacatctat gatagagcgc cacaataaca aacaattgcg ttttattatt 5220
acaaatccaa ttttaaaaaa agcggcagaa ccggtcaaac ctaaaagact gattacataa 5280
atcttattca aatttcaaaa gtgccccagg ggctagtatc tacgacacac cgagcggcga 5340
actaataacg ctcactgaag ggaactccgg ttccccgccg gcgcgcatgg gtgagattcc 5400
ttgaagttga gtattggccg tccgctctac cgaaagttac gggcaccatt caacccggtc 5460
cagcacggcg gccgggtaac cgacttgctg ccccgagaat tatgcagcat ttttttggtg 5520
tatgtgggcc ccaaatgaag tgcaggtcaa accttgacag tgacgacaaa tcgttgggcg 5580
ggtccagggc gaattttgcg acaacatgtc gaggctcagc aggacctgca ggcatgcaag 5640
cttggcactg gccgtcgttt tacaacgtcg tgactgggaa aaccctggcg ttacccaact 5700
taatcgcctt gcagcacatc ccccttttcgc cagctggcgt aatagcgaag aggcccgcac 5760
cgatcgccct tcccaacagt tgcgcagcct gaatggcgaa tgctagagca gcttgagctt 5820
ggatcagatt gtcgtttccc gccttcagtt taaactatca gtgtttgaca ggatatattg 5880
gcgggtaaa 5889

<210> SEQ ID NO 50
<211> LENGTH: 5250
<212> TYPE: DNA
<213> ORGANISM: Artificial sequence
<220> FEATURE:
<223> OTHER INFORMATION: TkOSC1-RNAi expression vector
<220> FEATURE:
<221> NAME/KEY: misc_feature
<222> LOCATION: (3041)..(3041)
<223> OTHER INFORMATION: n is a, c, g, or t
<220> FEATURE:
<221> NAME/KEY: misc_feature
<222> LOCATION: (3254)..(3254)
<223> OTHER INFORMATION: n is a, c, g, or t

<400> SEQUENCE: 50
tggcaggata tattgtggtg taaacaaatt gacgcttaga caacttaata acacattgcg 60
gacgttttta atgtactgaa ttaacgccga attaattcga gctcggatct gataatttat 120
ttgaaaattc ataagaaaag caaacgttac atgaattgat gaaacaatac aaagacagat 180
aaagccacgc acatttagga tattggccga gattactgaa tattgagtaa gatcacggaa 240
tttctgacag gagcatgtct tcaattcagc ccaaatggca gttgaaatac tcaaaccgcc 300
ccatatgcag gagcggatca ttcattgttt gtttggttgc ctttgccaac atgggagtcc 360
aagattctgc agtcaaatct cggtgacggg caggaccgga cggggcggta ccggcaggct 420

-continued

```
gaagtccagc tgccagaaac ccacgtcatg ccagttcccg tgcttgaagc cggccgcccg    480
cagcatgccg cggggggcat atccgagcgc ctcgtgcatg cgcacgctcg ggtcgttggg    540
cagcccgatg acagcgacca cgctcttgaa gccctgtgcc tccagggact tcagcaggtg    600
ggtgtagagc gtggagccca gtcccgtccg ctggtggcgg ggggagacgt acacggtcga    660
ctcggccgtc cagtcgtagg cgttgcgtgc cttccagggg cccgcgtagg cgatgccggc    720
gacctcgccg tccacctcgg cgacgagcca gggatagcgc tcccgcagac ggacgaggtc    780
gtccgtccac tcctgcggtt cctgcggctc ggtacggaag ttgaccgtgc ttgtctcgat    840
gtagtggttg acgatggtgc agaccgccgg catgtccgcc tcggtggcac ggcggatgtc    900
ggccgggcgt cgttctgggc tcatcgattc gatttggtgt atcgagattg gttatgaaat    960
tcagatgcta gtgtaatgta ttggtaattt gggaagatat aataggaagc aaggctattt   1020
atccatttct gaaaaggcga aatggcgtca ccgcgagcgt cacgcgcatt ccgttcttgc   1080
tgtaaagcgt tgtttggtac acttttgact agcgaggctt ggcgtgtcag cgtatctatt   1140
caaaagtcgt taatggctgc ggatcaagaa aaagttggaa tagaaacaga atacccgcga   1200
aattcaggcc cggttgccat gtcctacacg ccgaaataaa cgaccaaatt agtagaaaaa   1260
taaaaactga ctcggatact tacgtcacgt cttgcgcact gatttgaaaa atctcagaat   1320
taagcttccc gggattgttt catgcgcacg gaaacgttaa gagcttcgga ttatcatttt   1380
gataaagaaa ttaataaaag ataacgaaat aaatttaact ttaaaatttt gaaaatttat   1440
caggattctt atgaaagaaa ctgtatcagg attcttagga caaaaactag ctagttctct   1500
tttaaaatgt aaaacttatt ttttatgaaa gtattgaaca tcaaaaacta gtaggctaac   1560
atcatatgtg atttctgcat ggaacatctt atacacatgc agcatctcat tcacatgtaa   1620
ttgaactcgt cacgaaagtc attaaagtca ttaaactaac aatcaagata aactaaaaag   1680
ttatttaaat ttctttaaaa aaaatttgga acgacaacta ttgtaactta atcttaattt   1740
tacacatctc ggttcaaaca tgaaataaat attctaccca aacaataaat ggtaacttaa   1800
tttagtttct tttaatttgt tgattgctta taatctctta gataatataa atacgtcaaa   1860
tcagaagttg tggtatccac aaaaacgtgt tttaatgaat tcactaggtt aaaatcccgt   1920
gtaatacacg ggttaaaaat tttaaataca tataaataat ataattttat gtttgataat   1980
tcttaatatt tataacataa catgaacaat tttagaatat attaagattt aaaataagat   2040
aatagtaatt aatagttacc ataacaataa ttgaaaaata ttgtcaaaaa ttaggaaatt   2100
tcaattttga ttaaatgggc gggaaaataa aattgcgaaa gattatggtg ataacacgtg   2160
tcctatacgt attcttttat cagtagtaga ttatatgcaa gaaatgctaa atgacaaaaa   2220
cataaaagag tactatatat cgtagccaag cgatattcaa tatcattcaa ttttgaccta   2280
caattcatat atagacatat ctttgcgagc ccgttcacgt agtttctgga acctcgagta   2340
taagagctca tttttacaac aattaccaac aacaacaaac aacaaacaac attacaatta   2400
catttacaat tatccatgat caccactttg tacaagaaag ctgggtctag atatctcgag   2460
atcccaagct tgaatcgcac ggttcagtct aactgccttt ctcacggctg ttgtcaccgc   2520
ttcatagttc acatcttcgt cgtctccaag tctcactgga ggtacgctta taagatcaat   2580
tccgcccatg gtggagcctg ctttttttgta caaacttgtg atcatggggc gcgcccaatc   2640
gatgatttaa atgtgtaaga atttcttatg ttacattatt acattcaacg ttttatctta   2700
attggctctt catttgattg aaatttgaca attatttctt gtttttttttt ttgtcacact   2760
ctttttgggt tggggtggcc gacgaattgt gggaaggtag aaagagggga ggacttttgt   2820
```

```
tatactccat tagtaattac tgtttccgtt tcaatttatg tgacaatatt tcctttttag   2880
tcggttccaa aagaaaatgt cagcattata aacaatttaa ttttgaaatt acaattttgc   2940
cattaataaa atgatttaca accacaaaag tatctatgag cctgtttggg tgggcttata   3000
agcagcttat tttaagtggc ttataagtca aaaagtgaca ntttttgaga agttagaaaa   3060
tcctaacttc tcaaaaagta gcttttaagc cacttatgac ttataagtcc aaaaattttt   3120
aagttaccaa acatatatta atgggtttat aagcttataa gccactttta agctcaccca   3180
aacgggttct atgtctcact ttagactaca aattttaaaa gtcttcattt atttcttaat   3240
ctccgtggcg agtnaaacta taacacataa agtgaaacgg agggaataag atggagtcat   3300
aaactaatcc aaatctatac tctctccgtt aatttgtttt ttagtttgat ttggtacatt   3360
aataaaacag atttttcgaa ggttataaac acagacagat gtttcccagc gagctagcaa   3420
aattccaaga tttctgtcga aaattcgtgt gtttctagct agtacttgat gttatcttta   3480
acctttagt aattttttgt cctttcttt ctatttttca tcttacaatg aattatgagc   3540
aagttcctta agtagcatca cacgtgagat gttttttatg atattgacta aatccaatct   3600
ttaccattcc ttaactagta aaatacaaca catgttaatt gatacattgc ttaacactga   3660
ggttagaaaa ttttagaaat tagttgtcca aatgctttga aattagaaat ctttaatccc   3720
ttattttttt ttaaaatgtt ttttctcact ccaaagaaag agaaactgac atgaaagctc   3780
aaaagatcat gaatcttact aactttgtgg aactaaatgt acatcagaat gtttctgaca   3840
tgtgaaaatg aaagctctta attttcttct tttatttatt gagggttttt gcatgctatg   3900
cattcaattt gagtacttta aagcacctat aaacacttac ttacacttgc cttggagttt   3960
atgttttagt gttttcttca catctttttt ggtcaatttg caggtattgg atcctaggtg   4020
agtctagtca aacaagtttg tacaaaaaag caggctccac catgggcgga attgatctta   4080
taagcgtacc tccagtgaga cttggagacg acgaagatgt gaactatgaa gcggtgacaa   4140
cagccgtgag aaaggcagtt agactgaacc gtgcgattca agcttgggat ctcgagatat   4200
ctagacccag ctttcttgta caaagtggtt cgactagaga gttaattaag acccgggact   4260
agtccctaga gtcctgtctt taatgagata tgcgagacgc ctatgatcgc atgatatttg   4320
ctttcaattc tgttgtgcac gttgtaaaaa acctgagcat gtgtagctca gatccttacc   4380
gccggtttcg gttcattcta atgaatatat cacccgttac tatcgtattt ttatgaataa   4440
tattctccgt tcaatttact gattgtaccc tactacttat atgtacaata ttaaaatgaa   4500
aacaatatat tgtgctgaat aggtttatag cgacatctat gatagagcgc cacaataaca   4560
aacaattgcg ttttattatt acaaatccaa ttttaaaaaa agcggcagaa ccggtcaaac   4620
ctaaaagact gattacataa atcttattca aatttcaaaa gtgccccagg ggctagtatc   4680
tacgacacac cgagcggcga actaataacg ctcactgaag ggaactccgg ttccccgccg   4740
gcgcgcatgg gtgagattcc ttgaagttga gtattggccg tccgctctac cgaaagttac   4800
gggcaccatt caacccggtc cagcacggcg gccgggtaac cgacttgctg ccccgagaat   4860
tatgcagcat ttttttggtg tatgtgggcc ccaaatgaag tgcaggtcaa accttgacag   4920
tgacgacaaa tcgttgggcg ggtccagggc gaattttgcg acaacatgtc gaggctcagc   4980
aggacctgca ggcatgcaag cttggcactg gccgtcgttt tacaacgtcg tgactgggaa   5040
aaccctggcg ttacccaact taatcgcctt gcagcacatc ccccttcgc cagctggcgt   5100
aatagcgaag aggcccgcac cgatcgccct tcccaacagt tgcgcagcct gaatggcgaa   5160
```

-continued

```
tgctagagca gcttgagctt ggatcagatt gtcgtttccc gccttcagtt taaactatca    5220

gtgtttgaca ggatatattg gcgggtaaac                                     5250
```